(12) United States Patent
Coombs et al.

(10) Patent No.: US 8,377,901 B2
(45) Date of Patent: Feb. 19, 2013

(54) TARGET HOST FACTORS FOR TREATING VIRAL INFECTION

(75) Inventors: Kevin M. Coombs, Winnipeg (CA); John Wilkins, Winnipeg (CA); Anh T. Tran, Winnipeg (CA)

(73) Assignee: The University of Manitoba, Manitoba (CA)

( * ) Notice: Subject to any disclaimer, the term of this patent is extended or adjusted under 35 U.S.C. 154(b) by 0 days.

(21) Appl. No.: 12/831,964

(22) Filed: Jul. 7, 2010

(65) Prior Publication Data

US 2012/0009202 A1 Jan. 12, 2012

(51) Int. Cl.
*C12N 15/11* (2006.01)
*C07H 21/04* (2006.01)
*C12Q 1/68* (2006.01)
*C12N 5/00* (2006.01)
*C12N 5/02* (2006.01)

(52) U.S. Cl. ........ 514/44 A; 536/24.5; 435/6.1; 435/375
(58) Field of Classification Search .................. None
See application file for complete search history.

(56) References Cited

U.S. PATENT DOCUMENTS

| | | | | |
|---|---|---|---|---|
| 5,856,445 A | * | 1/1999 | Korsmeyer | .................. 530/350 |
| 6,573,079 B1 | * | 6/2003 | Palese et al. | ............... 435/235.1 |
| 2007/0015172 A1 | * | 1/2007 | Zhang et al. | ..................... 435/6 |
| 2007/0099182 A1 | * | 5/2007 | Hildebrand et al. | .............. 435/5 |

OTHER PUBLICATIONS

Hong et al., Induction of apoptotic death in cells via Bad gene expression by infectious pancreatic necrosis virus infection, 2002, Cell Death and Differentiation, vol. 9, pp. 113-124.*

* cited by examiner

*Primary Examiner* — Dana Shin

(57) ABSTRACT

A method of reducing virus-mediated cytotoxicity comprising contacting virus-infected cells with an effective amount of at least one inhibitor of ABI2, ARRDC3, BAD, BRCA1, C17orf85, C1orf71, C6orf162, CCNJL, CFL1, GON4L, HCG 1986447, HIST1H2AB, HPS4, LHX8, RPS25, RPL23, RPL32, LOC730139, LRRC39, MALT1, MX1, MERTK, MX2, NRG1, OR52A1, PLEKHH1, PTPN13, PTPRJ, RLN1, RNF19A, SH3BP4, SLC7A14, ST8SIA3, STX3, TMC6, TMTC4, TNFSF12-TNFSF13, TNFSF13, TTN, UBXN7, USP47, WNK2, YPEL2, ZNF251 and/or SCG2.

8 Claims, 21 Drawing Sheets

FIGURE 1A

SEQ ID NO:10; BAD transcript variant 1

```
>gi|197116381|ref|NM_004322.3| Homo sapiens BCL2-associated agonist of cell
death (BAD), transcript variant 1, mRNA
AACTAGGGCCCGGAGCCCGGGGTGCTGGAGGGAGGCGGCAGGCCCGGGTCAGGGGCCTCGAGATCGGGCT
TGGGGTGAGACCTGTGCGCCGTCACCACGGGCGGGGCGGGGCCTGGGTCCACCGGGGTTCTGAGGGGAGA
CTGAGGTCCTGAGCCGACAGCCTCAGCTCCCTGCCAGGCCAGACCCGGCAGACAGATGAGGGCCCAGGAG
GCCTGGCGGGCCTGGGGGCGCTACGGTGGGAGAGGAAGCCAGGGGTACCTGCCTCTGCCTTCCAGGGCCA
CCGTTGGCCCCAGCTGTGCCTTGACTACGTAACATCTTGTCCTCACAGCCCAGAGCATGTTCCAGATCCC
AGAGTTTGAGCCGAGTGAGCAGGAAGACTCCAGCTCTGCAGAGAGGGCCTGGGCCCCAGCCCCGCAGGG
GACGGGCCCTCAGGCTCCGGCAAGCATCATCGCCAGGCCCCAGGCCTCCTGTGGGACGCCAGTCACCAGC
AGGAGCAGCCAACCAGCAGCAGCCATCATGGAGGCGCTGGGGCTGTGGAGATCCGGAGTCGCCACAGCTC
CTACCCCGCGGGGACGGAGGACGACGAAGGGATGGGGGAGGAGCCCAGCCCCTTTCGGGGCCGCTCGCGC
TCGGCGCCCCCAACCTCTGGGCAGCACAGCGCTATGGCCGCGAGCTCCGGAGGATGAGTGACGAGTTTG
TGGACTCCTTTAAGAAGGGACTTCCTCGCCCGAAGAGCGCGGGCACAGCAACGCAGATGCGGCAAAGCTC
CAGCTGGACGCGAGTCTTCCAGTCCTGGTGGGATCGGAACTTGGGCAGGGGAAGCTCCGCCCCTCCCAG
TGACCTTCGCTCCACATCCCGAAACTCCACCCGTTCCCACTGCCCTGGGCAGCCATCTTGAATATGGGCG
GAAGTACTTCCCTCAGGCCTATGCAAAAAGAGGATCCGTGCTGTCTCCTTTGGAGGGAGGGCTGACCCAG
ATTCCCTTCCGGTGCGTGTGAAGCCACGGAAGGCTTGGTCCCATCGGAAGTTTTGGGTTTTCCGCCCACA
GCCGCCGGAAGTGGCTCCGTGGCCCCGCCCTCAGGCTCCGGGCTTTCCCCCAGGCGCCTGCGCTAAGTCG
CGAGCCAGGTTTAACCGTTGCGTCACCGGGACCCGAGCCCCGCGATGCCCTGGGGGCCGTGCTCACTAC
CAAATGTTAATAAAGCCCGCGTCTGTGCCGCCGAAAAAAAAAAAAAAAAA
```

FIGURE 1B

SEQ ID NO:103; BAD transcript variant 2

```
>gi|197116382|ref|NM_032989.2| Homo sapiens BCL2-associated agonist of cell
death (BAD), transcript variant 2, mRNA
AACTAGGGCCCGGAGCCCGGGGTGCTGGAGGGAGGCGGCAGGCCCGGGTCAGGGGCCTCGAGATCGGGCT
TGGGCCCAGAGCATGTTCCAGATCCCAGAGTTTGAGCCGAGTGAGCAGGAAGACTCCAGCTCTGCAGAGA
GGGGCCTGGGCCCCAGCCCCGCAGGGGACGGGCCCTCAGGCTCCGGCAAGCATCATCGCCAGGCCCCAGG
CCTCCTGTGGGACGCCAGTCACCAGCAGGAGCAGCCAACCAGCAGCAGCCATCATGGAGGCGCTGGGGCT
GTGGAGATCCGGAGTCGCCACAGCTCCTACCCCGCGGGGACGGAGGACGACGAAGGGATGGGGGAGGAGC
CCAGCCCCTTTCGGGGCCGCTCGCGCTCGGCGCCCCCAACCTCTGGGCAGCACAGCGCTATGGCCGCGA
GCTCCGGAGGATGAGTGACGAGTTTGTGGACTCCTTTAAGAAGGGACTTCCTCGCCCGAAGAGCGCGGGC
ACAGCAACGCAGATGCGGCAAAGCTCCAGCTGGACGCGAGTCTTCCAGTCCTGGTGGGATCGGAACTTGG
GCAGGGGAAGCTCCGCCCCTCCCAGTGACCTTCGCTCCACATCCCGAAACTCCACCCGTTCCCACTGCC
CTGGGCAGCCATCTTGAATATGGGCGGAAGTACTTCCCTCAGGCCTATGCAAAAAGAGGATCCGTGCTGT
CTCCTTTGGAGGGAGGGCTGACCCAGATTCCCTTCCGGTGCGTGTGAAGCCACGGAAGGCTTGGTCCCAT
CGGAAGTTTTGGGTTTTCCGCCCACAGCCGCCGGAAGTGGCTCCGTGGCCCCGCCCTCAGGCTCCGGGCT
TTCCCCCAGGCGCCTGCGCTAAGTCGCGAGCCAGGTTTAACCGTTGCGTCACCGGGACCCGAGCCCCGC
GATGCCCTGGGGGCCGTGCTCACTACCAAATGTTAATAAAGCCCGCGTCTGTGCCGCCGAAAAAAAAAA
AAAAAA
```

FIGURE 1C

SEQ ID NO: 24; *MX2* transcript

```
>gi|11342663|ref|NM_002463.1| Homo sapiens myxovirus (influenza virus)
resistance 2 (mouse) (MX2), mRNA
AAGAGATGATTTCTCCATCCTGAACGTGCAGCGAGCTTGTCAGGAAGATCGGAGGTGCCAAGTAGCAGAG
AAAGCATCCCCCAGCTCTGACAGGGAGACAGCACATGTCTAAGGCCCACAAGCCTTGGCCCTACCGGAGG
AGAAGTCAATTTTCTTCTCGAAAATACCTGAAAAAAGAAATGAATTCCTTCCAGCAACAGCCACCGCCAT
TCGGCACAGTGCCACCACAAATGATGTTTCCTCCAAACTGGCAGGGGGCAGAGAAGGACGCTGCTTTCCT
CGCCAAGGACTTCAACTTTCTCACTTTGAACAATCAGCCACCACCAGGAAACAGGAGCCAACCAAGGGCA
ATGGGGCCCGAGAACAACCTGTACAGCCAGTACGAGCAGAAGGTGCGCCCCTGCATTGACCTCATCGACT
CCCTGCGGGCTCTGGGTGTGGAGCAGGACCTGGCCCTGCCAGCCATCGCCGTCATCGGGGACCAGAGCTC
GGGCAAGAGCTCTGTGCTGGAGGCACTGTCAGGAGTCGCGCTTCCCAGAGGCAGCGGAATCGTAACCAGG
TGTCCGCTGGTGCTGAAACTGAAAAGCAGCCCTGTGAGGCATGGGCCGGAAGGATCAGCTACCGGAACA
CCGAGCTAGAGCTTCAGGACCCTGGCCAGGTGGAGAAAGAGATACACAAAGCCCAGAACGTCATGGCCGG
GAATGGCCGGGGCATCAGCCATGAGCTCATCAGCCTGGAGATCACCTCCCCTGAGGTTCCAGACCTGACC
ATCATTGACCTTCCCGGCATCACCAGGGTGGCTGTGGACAACCAGCCCCGAGACATCGGACTGCAGATCA
AGGCTCTCATCAAGAAGTACATCCAGAGGCAGCAGACGATCAACTTGGTGGTGGTTCCCTGTAACGTGGA
CATTGCCACCACGGAGGCGCTGAGCATGGCCCATGAGGTGGACCCGGAAGGGGACAGGACCATCGGTATC
CTGACCAAACCAGATCTAATGGACAGGGGCACTGAGAAAAGCGTCATGAATGTGGTGCGGAACCTCACGT
ACCCCCTCAAGAAGGGCTACATGATTGTGAAGTGCCGGGGCCAGCAGGAGATCACAAACAGGCTGAGCTT
GGCAGAGGCAACCAAGAAAGAAATTACATTCTTTCAAACACATCCATATTTCAGAGTTCTCCTGGAGGAG
GGGTCAGCCACGGTTCCCCGACTGGCAGAAAGACTTACCACTGAACTCATCATGCATATCCAAAAATCGC
TCCCGTTGTTAGAAGGACAAATAAGGGAGAGCCACCAGAAGGCGACCGAGGAGCTGCGGCGTTGCGGGGC
TGACATCCCCAGCCAGGAGGCCGACAAGATGTTCTTTCTAATTGAGAAAATCAAGATGTTTAATCAGGAC
ATCGAAAAGTTAGTAGAAGGAGAAGAAGTTGTAAGGGAGAATGAGACCCGTTTATACAACAAAATCAGAG
AGGATTTTAAAAACTGGGTAGGCATACTTGCAACTAATACCCAAAAAGTTAAAAATATTATCCACGAAGA
AGTTGAAAAATATGAAAAGCAGTATCGAGGCAAGGAGCTTCTGGGATTTGTCAACTACAAGACATTTGAG
ATCATCGTGCATCAGTACATCCAGCAGCTGGTGGAGCCCGCCCTTAGCATGCTCCAGAAAGCCATGGAAA
TTATCCAGCAAGCTTTCATTAACGTGGCCAAAAAACATTTTGGCGAATTTTTCAACCTTAACCAAACTGT
TCAGAGCACGATTGAAGACATAAAAGTGAAACACACAGCAAAGGCAGAAAACATGATCCAACTTCAGTTC
AGAATGGAGCAGATGGTTTTTTGTCAAGATCAGATTTACAGTGTTGTTCTGAAGAAAGTCCGAGAACAGA
TTTTTAACCCTCTGGGGACGCCTTCACAGAATATGAAGTTGAACTCTCATTTTCCCAGTAATCAGTCTTC
GGTTTCCTCCTTTACTGAAATAGGCATCCACCTGAATGCCTACTTCTTGGAAACCAGCAAACGTCTCGCC
AACCAGATCCCATTTATAATTCAGTATTTTATGCTCCGAGAGAATGGTGACTCCTTGCAGAAAGCCATGA
TGCAGATACTACAGGAAAAAATCGCTATTCCTGGCTGCTTCAAGAGCAGAGTGAGACCGCTACCAAGAG
AAGAATCCTTAAGGAGAGAATTTACCGGCTCACTCAGGCGCGACACGCACTCTGTCAATTCTCCAGCAAA
GAGATCCACTGAAGGCGGCGATGCCTGTGGTTGTTTTCTTGTGCGTACTCATTCATTCTAAGGGGAGTC
GGTGCAGGATGCCGCTTCTGCTTTGGGGCCAAACTCTTCTGTCACTATCAGTGTCCATCTCTACTGTACT
CCCTCAGCATCAGAGCATGCATCAGGGGTCCACACAGGCTCAGCTCTCTCCACCACCCAGCTCTTCCCTG
ACCTTCACGAAGGGATGGCTCTCCAGTCCTTGGGTCCCGTAGCACACAGTTACAGTGTCCTAAGATACTG
CTATCATTCTTCGCTAATTTGTATTTGTATTCCCTTCCCCCTACAAGATTATGAGACCCCAGAGGGGGAA
GGTCTGGGTCAAATTCTTCTTTGTATGTCCAGTCTCCTGCACAGCACCTGCAGCATTGTAACTGCTTAA
TAAATGACATCTCACTGAACGAATGAGTGCTGTGTAAGTGATGGAGATACCTGAGGCTATTGCTCAAGCC
CAGGCCTTGGACATTTAGTGACTGTTAGCCGGTCCCTTTCAGATCCAGTGGCCATGCCCCCTGCTTCCCA
TGGTTCACTGTCATTGTGTTTCCCAGCCTCTCCACTCCCCGCCAGAAAGGAGCCTGAGTGATTCTCTTT
TCTTCTTGTTTCCCTGATTATGATGAGCTTCCATTGTTCTGTTAAGTCTTGAAGAGGAATTTAATAAAGC
AAAGAAACTTTTTAAAAACGT
```

FIGURE 1D

SEQ ID NO:30; *USP47* transcript

\>gi|71774196|ref|NM_017944.3| Homo sapiens ubiquitin specific peptidase 47
(USP47), mRNA
AGAGGGGAAAAGAACGTCAGGAGAGTGAACGGGAGCAAATAAAACGCTGTCCATTCTGACTGGAAGGGCC
AGAGCCGTGTCTAAGGGCGGGGGCCGGGAGGTGGCCCGCGGTGGTGTCTCTACCAGGACGAGGCCTGGGG
TATCTGAAGAGGGGATGACGTCCAGGCGCTTTGCTAAAGGGAAGCCAGAAGGGTATGAGTTGCTAGGGTC
AGAGATGGGGCTTTCGGCTCGAGTCTTTCCCTGCAGGGCAGAGAGTCCGAAGAGCCCGAGAAGGCAGGGA
GGACAGTGGGCCTGGTCCTTCCCCGGCCGGCAGAGGGAGTCCCGAGATGGAACGTCCAGCTCTCCTCTAA
CGAAAAGCGTTTGCATGGCTGTCTCGCCAATTCTGTACCTCCCGGGGCTGAGGAAGAGCCGAGGTGACTA
GAAGCTAGCGACAAGTGCCGGCCACCTCCGACGCCAGGCGCCGGGCTTGGAGCCCGACGGGCCGAATTCT
CGCGAGAGCGGCCGCCGCCATTTTTCCATTGATTGCAGCGGGCTGGGGGAGGGGCCGACGACGAAGGCGG
CTGTGGTAGCGGCGGCGGCGGCGGCGGAGCCCTGGGTCGGTGTCTGCGCGCTGGTGTCTGAGGCCCAGGC
TGAGGCCTCCGCTATTGCTGGAGCGCAGGCGGCGGAGAGGATGACTGCCGCTGCCATTCTCTCTTGAGCT
AGCGAGCCGCCGCCACCCTCCACCCTCCCCCGGCAGGGCGGAGAGGAGCGGCCGGAGTCAGCGATGGTGC
CCGGCGAGGAGAACCAACTGGTCCCGAAAGAGGCACCACTGGATCATACCAGTGACAAGTCACTTCTCGA
CGCTAATTTTGAGCCAGGAAAGAAGAACTTTCTGCATTTGACAGATAAAGATGGTGAACAACCTCAAATA
CTGCTGGAGGATTCCAGTGCTGGGGAAGACAGTGTTCATGACAGGTTTATAGGTCCGCTTCCAAGAGAAG
GTTCTGGGGGTTCTACCAGTGATTATGTCAGCCAAAGCTACTCCTACTCATCTATTTGAATAAATCAGA
AACTGGATATGTGGGACTAGTAAACCAAGCAATGACTTGCTATTGAATAGCCTTTTGCAAACACTTTTT
ATGACTCCTGAATTTAGGAATGCATTATATAAGTGGGAATTTGAAGAATCTGAAGAAGATCCAGTGACAA
GTATTCCATACCAACTTCAAAGGCTTTTTGTTTGTTACAAACCAGCAAAAAGAGAGCAATTGAAACCAC
AGATGTTACAAGGAGCTTTGGATGGGATAGTAGTGAGGCTTGGCAGCAGCATGATGTACAAGAACTATGC
AGAGTCATGTTTGATGCTTTGGAACAGAAATGGAAGCAAACAGAACAGGCTGATCTTATAAATGAGCTAT
ATCAAGGCAAGCTGAAGGACTACGTGAGATGTCTGGAATGTGGTTATGAGGGCTGGCGAATCGACACATA
TCTTGATATTCCATTGGTCATCCGACCTTATGGGTCCAGCCAAGCATTTGCTAGTGTGGAAGAAGCATTG
CATGCATTTATTCAGCCAGAGATTCTGGATGGCCCAAATCAGTATTTTGTGAACGTTGTAAGAAGAAGT
GTGATGCACGGAAGGGCCTTCGGTTTTTGCATTTTCCTTATCTGCTGACCTTACAGCTGAAAAGATTCGA
TTTTGATTATACAACCATGCATAGGATTAAACTGAATGATCGAATGACATTTCCGAGGAACTAGATATG
AGTACTTTTATTGATGTTGAAGATGAGAAATCTCCTCAGACTGAAAGTTGCACTGACAGTGGAGCAGAAA
ATGAAGGTAGTTGTCACAGTGATCAGATGAGCAACGATTTCTCCAATGATGATGGTGTTGATGAAGGAAT
CTGTCTTGAAACCAATAGTGGAACTGAAAAGATCTCAAAATCTGGACTTGAAAAGAATTCCTTGATCTAT
GAACTTTTCTCTGTTATGGTTCATTCTGGGAGCGCTGCTGGTGGTCATTATTATGCATGTATAAAGTCAT
TCAGTGATGAGCAGTGGTACAGCTTCAATGATCAACATGTCAGCAGGATAACACAAGAGGACATTAAGAA
AACACATGGTGGATCTTCAGGAAGCAGAGGATATTATTCTAGTGCTTTCGCAAGTTCCACAAATGCATAT
ATGCTGATCTATAGACTGAAGGATCCAGCCAGAAATGCAAAATTTCTAGAAGTGGATGAATACCCAGAAC
ATATTAAAAACTTGGTGCAAGAGAGAGAGTTGGAAGAACAAGAAAAGAGACAACGAGAAATTGAGCG
CAATACATGCAAGATAAAATTATTCTGTTTGCATCCTACAAAACAAGTAATGATGGAAAATAAATTGGAG
GTTCATAAGGATAAGACATTAAAGGAAGCAGTAGAAATGGCTTATAAGATGATGGATTTAGAAGAGGTAA
TACCCCTGGATTGCTGTCGCCTTGTTAAATATGATGAGTTTCATGATTATCTAGAACGGTCATATGAAGG
AGAAGAAGATACACCAATGGGGCTTCTACTAGGTGGCGTCAAGTCAACATATATGTTTGATCTGCTGTTG
GAGACGAGAAAGCCTGATCAGGTTTTCCAATCTTATAAACCTGGAGAAGTGATGGTGAAAGTTCATGTTG
TTGATCTAAAGGCAGAATCTGTAGCTGCTCCTATAACTGTTCGTGCTTACTTAAATCAGACAGTTACAGA
ATTCAAACAACTGATTTCAAAGGCCATCCATTTACCTGCTGAAACAATGAGAATAGTGCTGGAACGCTGC
TACAATGATTTGCGTCTTCTCAGTGTCTCCAGTAAAACCCTGAAAGCTGAAGGATTTTTTAGAAGTAACA
AGGTGTTTGTTGAAAGCTCCGAGACTTTGGATTACCAGATGGCCTTGCAGACTCTCATTTATGGAAACT
CCTGGATCGGCATGCAAATACAATCAGATTATTGTTTTGCTACCTGAACAATCCCCAGTATCTTATTCC
AAAAGGACAGCATACCAGAAAGCTGGAGGCGATTCTGGTAATGTGGATGATGACTGTGAAAGAGTCAAAG
GACCTGTAGGAAGCCTAAAGTCTGTGGAAGCTATTCTAGAAGAAAGCACTGAAAAACTCAAAAGCTTGTC
ACTGCAGCAACAGCAGGATGGAGATAATGGGACAGCAGCAAAAGTACTGAGACAAGTGACTTTGAAAAC
ATCGAATCACCTCTCAATGAGAGGGACTCTTCAGCATCAGTGGATAATAGAGAACTTGAACAGCATATTC
AGACTTCTGATCCAGAAAATTTTCAGTCTGAAGAACGATCAGACTCAGATGTGAATAATGACAGGAGTAC
AAGTTCAGTGGACAGTGATATTCTTAGCTCCAGTCATAGCAGTGATACTTTGTGCAATGCAGACAATGCT
CAGATCCCTTTGGCTAATGGACTTGACTCTCACAGTATCACAAGTAGTAGAAGAACGAAAGCAAATGAAG FIGURE 1D (Continued)

```
GGAAAAAAGAAACATGGGATACAGCAGAAGAAGACTCTGGAACTGATAGTGAATATGATGAGAGTGGCAA
GAGTAGGGGAGAAATGCAGTACATGTATTTCAAAGCTGAACCTTATGCTGCAGATGAAGGTTCTGGGGAA
GGACATAAATGGTTGATGGTGCATGTTGATAAAAGAATTACTCTGGCAGCTTTCAAACAACATTTAGAGC
CCTTTGTTGGAGTTTTGTCCTCTCACTTCAAGGTCTTTCGAGTGTATGCCAGCAATCAAGAGTTTGAGAG
CGTCCGGCTGAATGAGACACTTTCATCATTTTCTGATGACAATAAGATTACAATTAGACTGGGGAGAGCA
CTTAAAAAAGGAGAATACAGAGTTAAAGTATACCAGCTTTTGGTCAATGAACAAGAGCCATGCAAGTTTC
TGCTAGATGCTGTGTTTGCTAAAGGAATGACTGTACGGCAATCAAAAGAGGAATTAATTCCTCAGCTCAG
GGAGCAATGTGGTTTAGAGCTCAGTATTGACAGGTTTCGTCTAAGGAAAAAAACATGGAAGAATCCTGGC
ACTGTCTTTTTGGATTATCATATTTATGAAGAAGATATTAATATTTCCAGCAACTGGGAGGTTTTCCTTG
AAGTTCTTGATGGGGTAGAGAAGATGAAGTCCATGTCACAGCTTGCAGTTTTGTCAAGACGGTGGAAGCC
TTCAGAGATGAAGTTGGATCCCTTCCAGGAGGTTGTATTGGAAAGCAGTAGTGTGGACGAATTGCGAGAG
AAGCTTAGTGAAATCAGTGGGATTCCTTTGGATGATATTGAATTTGCTAAGGGTAGAGGAACATTTCCCT
GTGATATTTCTGTCCTTGATATTCATCAGGATTTAGACTGGAATCCTAAAGTTTCTACCCTGAATGTCTG
GCCTCTTTATATCTGTGATGATGGTGCGGTCATATTTTATAGGGATAAAACAGAAGAATTAATGGAATTG
ACAGATGAGCAAAGAAATGAACTGATGAAAAAGAAAGCAGTCGACTCCAGAAGACTGGACATCGTGTAA
CATACTCACCTCGTAAAGAGAAAGCACTAAAAATATATCTGGATGGAGCACCAAATAAAGATCTGACTCA
AGACTGACTCTGATAGTGTAGCATTTTCCCTGGGGGAGTTTTGGTTTTAATTAGATGGTTCACTACCACT
GGGTAGTGCCATTTTGGCCGGACATGGTTGGGGTAACCCAGTGACACCAGCACTGATTGGACTGCCCTAC
ACCAATCAGAAGCTCAGTGCCCAATGGGCCACTGTTTTGACTCGGAATCATGTTGTGCACTATAGTCAAA
TGTACTGTAAAGTGAAAAGGGATGTGCAAAAAAATAAAAAAAAAACAACAAAAAAAGCTAACCTTCTATTA
GAAAAGGGGACAGGGGAATGAGTAAACTTCTTTTATTGCGGACAAATGTGCACATAGCCGCTAGTAAAAC
TAGCCTCAAACAGGATGCTCATAGCTTAATAATAAAAGCTGTGCAAAGGCCATGAATGAATGAATTTTCT
GTTTATTTCACTGATGCACACATTACCTCATTGACAATTCAGAAGTAAATCCAACGTGTGTTGACTCTTG
GAAAGCAGCAAAAACAGGAGCTGAAGAAAAGAAATTCTTGGAACCAGCCGTAACCCAGTAAGGAATTGTG
AAGTTGTGTTTTTATTTTGTTTCATTTTTTGCAGAGTATTAAGAACATTATTCTGGAACATCAGAACGTT
TCCCTTAGACCGATCCCAGCAGGTGGCAGCTCAGATTGCTGCAGTGTTGTAATTATAACTGATTGTACTT
AAGTTATGGATGTAGAGAATATGTTTCATTCATTTATTCAGCATGTAAATAAAATTGATCCTGTTGAGTT
ATCATAATTGCAGTTCAACTATCTGCCATGATTATTCTTTTCACGTATCATTCATTCTGTACATTTGTGT
ACATTGAGAAGTATAGCAATCTATGTAAATGTAATCCTCAGTGAGGTTCCTCAGTGCTAGGTCCCATAGG
ATTGTCGTTGCCCTTGTTAATGAGGTTTCTCTGTTCAGCGGCTTCAATTTTTTCTCTTGTACATCTAG
TTTTGAAGATTTACTTCAAGTTTGAATCTTCTAGAATGCTTGTAAGTCCAGTTTTAATTTTAGAGTCAA
TTTGTAGTTACATGTAGTTTAACTTTTGGGAAACGTCTTAACATTGTTCTGAATAAACTTGCTAATGAGG
TCAGGTCATGGTACAGACTGATGCAGTCAACATGATTTCATTGCAGAGTTTATTAGTATCAGCAAGTTTT
TGCTTTGCTAAATAAAAGTACTCAATGAACACAATTCTACATAAATTTTGACATACCATCTAATTTATAA
AAATCAATAAAAAAGGTTTTGGTAAAACTTTTTCATGCCAGATGCTGTTTACAACAATGAACATGCCAAT
AAAACATTTGTTCATTCTGTTGTGTTATTTTAGTCATTAAACTTCTGTGGATGAAGAATCTGGGTTAAGA
ATAGATTTGTCATCTTTAAATATGACATTTTGTAATGTGTATTGGATATCTCATTTCTATGATAAAGGTA
TATTTACAGTAAAGTTCTCATAAGAGAAATGAAAAGCTGTGTTAATATCTAACTTTGGGGAACCCTGTCA
GTATTTCAGATCCGATTTTTACCCTTTTTTTCTTATAAGAAAGATAAAATTAGAAAATACTGTTAGCAAA
TGTGGCTCTGCCATTTGAATATAATCACCGAGAATTCCATGTCTTAAAAGTCTCCTGGAATCCACAATGA
AAAAAAAATCTTTTCTAAGGTATTTTTCTGGCTAATTTTTATTTGAAGAAAGCTATAGCATTTAGCGAA
ATTTGACTGAAGTAATGTTCTGAGTTTGCATTAGTGGGATTGGTGATGTTCTCAGAAGAAAATTGGAAAC
ACTTGTGATGAATTGTCTTTCAGATCACTTAGATTTTCTGATGTAAGAGGACAGCTGTTGGTTCTGATA
CAGGCCTGCTTACTTGGGATGTAGGGTTAGTAAATGGGGTTTCTGCTTTAAAGGACTGACTTGCTATCAC
ACAAAAGAGGCAGACTTGTAAACACAATGGGCTTTGGAGTTTGGTCTGATTGGGTTTGGTTTAGTATTCC
TATGAGCGTAAATGGTAAAATCTTCTGATACCCACTCTTTAGACTGTGCCTTCTGCTCTGTTCTTTGTT
TTATGTTTAACTGCTGTTTCTAATTGCAGGTGTATTACAGATACAAATAAGAGTAAAGAAAATATATTC
ATTATAGAAAAGAAAAATTAAAAGCTTCTTGCTTTTCAGTGCCTGATAGAGTGAAAACACAAAGTTGCA
CTTTAATAATTTCAATAAAAGCTAATCTGTGTCAGCCTCCCTCTGCTTCAGAGAGTCAGGTGAGCATCCA
TAACCTAACAGGCAGAGCCCTAGCGATGTGGATCAAGTTTCCTGAGCCCGGGGCGGTGGAGCCTCATGA
TCTCTTATCTTTTGAGGCTGAGGCAGGTCACATGCAACAAATTGTGACCCTGCTCCCACAAGTCATGCA
AAGGTTTTGAAGAGCTTTTACCGTGGGGCAGATGAACTTGTGTCAACCATGCACACCCTGTGAGAACCAA
GTACCTGTGTTTCTAAGGCGGGCACTCAAGGTGAGGGGTGCATTCTGGCCAAAGAAACAAAAGCTGTGGT
TTCAGGACCATGCCGTGTGTAGCTGATCTGTACGGGACGTGTATGTAAGGAAGAGCAATCATGATAGATA
AGAACAGTGTGTGAAGCAGCCTTCACACTAGAGTGTTTGGTCATCTCTTATAATGTAAGGGAAGGTACTT
TAAAATTCTGGGAAGATGCGATGAACTCATGTCCCAGTCAGAAAATAATCCAATGAAATAAGCATTGGTT
GCCAGGCCACAGTTAGGAATTGTATTGTGATACATCTAGAGGCCAAGAGAGCAGGAGAGAGCTACCAACT
```

FIGURE 1D (Continued)

```
TACACTGTGGTTTAAGCTAAATGACCGCACAGCATCATAGCATTGCAGTGTTGTTACTAAATCTGGAAGT
GACCTGTGAATGTATGGAATACAATAAAGTCTTTTATTCTGGTTCATTTGCTAGTACTTCCTTTTTGATT
GGATACTGTAGTTCTTCCTCTGGATTTTATTTTGTTCAGCGTCAAGGCCCTAATTTTGCAAATGTAGTCT
AAACCACATTACGTGGACTAGAGGATACTCTGAATTAGCAAGTTTTTTGTTTGCTGAATAAAACTATTCC
ATCTTAA
```

FIGURE 1E

SEQ ID NO:46; HCG 1986447 transcript

```
>gi|239741609|ref|XR_041499.2| PREDICTED: Homo sapiens
hCG1986447 (LOC729324), miscRNA
GTCGCACACCACCACCTTCCTGCCCTGGCTGTCCATCGTCCGCCCAGGGAAGAGCCGCTGCAGCCGCACAACCTACA
GCCACCGCCGCCCGGCCGTTTTCTCTTCTTCCTCTTGCGTCTTCCCGGCCCCTCCTTCGGCCCAACTTTTTTCCCCC
GACCGGAAGCCGCCGCCGGGCTCCGCCCGTCATTTAGCTGAATGCCTGCACGAAAAGGGTGGGACGGGCAGGCAGCG
CGACTGGCAGCGGTGAGCTCCAATAAAAGATGGAGGAGCGTCGAGGCCCCTCCCGCAGCTCCGCTTCCGGCTCGGCT
GTCACGGTCGCTGCCCACCCGGGTTCTTCGCTGCTTCTAGTTCCGGGCGCTTTGCCGGGCGTTAATGGCGGCCAACA
TCGCCGGTGCTGCGGCTTTCTCCCTAAAGTGTCACAGGAGCTAAGGGCGCTGCTTAACGAACTGCAGAAGACGCAGG
CAGGTGAAGGACACCGGTTCTGCTGCGGCAGTGGAATGTGGCGGAGAAGCTGGCGGGTAGGGCGGGGAGCAAGCCTG
GAGGTCCTGGCGGACCCCACCATTCGACAGGGCTTGGTGTGTTATTGCTTCTAGGCCTTTTCAGCGGACAGAACTGG
GATGGATACACACATGCTTATTTGAAATCATGCGTTTGTTCCATACTCCAATGTCAGCCCACCCCTTCTTTGCCCAA
GTTGCTCTATGGTCAAGTGAGCGAGAGCAGGTGCCTGCATTCCAGCCTCGTGGCTCACCGCCTCCTTCCAGTAGTC
CCATGTTGCTTCACACCTCTTAAGTACATGTACTTCTGTGAACCCAGAGCCTTGGCTTTGAAATCAGACAACCCCAG
TTTCAAACGTGGCGCTGCCACTCACGAGTTTTGTGATTTTGGCATACCCCTGTCTGCATGGGGATAATAACTTCTAT
CTCCATAGGTGTGGTGAGGATAAAAGTCTATGCATGGAGGAAATGTTCATTCAGTGGTAGCTATTTCTAATTCTGTT
CTTCTGGACCTATGATTCTATCTACGATGCCTCATTTTTTTTCCTTTTTAATCAATTGGCAAACTTGTGCTCTGAGA
CCCAGCTTGTTACATCTCTGATGACAGCTGATATCCTCAGGATATTCCGTACTTCCTTTCTCCCTATTACTTTACTA
TGAATATATGAATAACATTGTGCTTATTGCATGCAACAAATATTTATTAGATGAATGACATTAAAATTCACCTTTAA
AATGCCATCCTTTATGAGAGGTGAGAAATAGAACTTTTCCTTCGACATGGCTGTACATGTTCAACAACTAGAATAAA
ACAGTCATCATGAACCCTCAATCCAGTATTCTTTTTATAATATAGCTGCCTGTCAGTTTTCACTGTTCTTTTATTAG
ACCAGTGATTTTCAAACCTTTTTAAAGGCATACAGTGCTTTATTCAAATCTAATCTTATATGGAACCCTCAACACAT
AAATATTAAGATAAAAATAAAGCTGCCATTGTTGCAATTAGAAGTTTGAGAGGTTAGAATAGGTAGGAAGTCTCGGA
GGAACATTTCTTCGTTTTACCTGCTTTAACAGTCAGAGAAGTACCTCAGCCAGCAGAAAAATTTATTTGTTCATAAA
TTCCTTGAGTATAGAGTCCGTATCTTATTTTTGTGGCCTCCAATGCTAGTGCTGTGCAGTTTTCTTGAAAGTGCATT
TTATTGGTCTCAGCAAATTGAACTCAAGCATTTCTGTGTTCTTTTACTTTTCCTCTTTGTGGAATTAAGGGGATTGC
TAATTTGTATTTTTAAAGAAAGAACATTATTCCGGGCGCGGTGGCTCACGCCTGTAATCCCAGCACTTGGGGAGGCC
AAGGAGGGCAAATCACCTGAGATCAGGAGTTCAAGACAAGGCTGACCAACATGGCAAAACCCCGTCTCTACTAAAAA
TACAAAAATTAGCTGGGCGTGTTGGCACGCGCCTGTAATCCCAGCCACTCAGGAAGCTGAGGCAGGAGAATCGCTTG
AACCCGGGAAGCAGAGGTTGCAGTGACAGAGATCGTGCCACTGCACTCCAGCCTGGTGAGAGCAAGACTCTGTCTCA
AAAAAAAAAAAAAAAATTGGCAAGTTTGGCCCTAAAATTTATATGAAATGAAAAGGAACCAGAATAAAAGGATTTC
GAAACAGAAAAAGATGGAGAACTTCCACTACCTGAATTCAAAACTTATTATAAAGCTACAGTAATGAAGACTGTAAT
ACTGGCATAGAGGCAGATATATCGATCAATGGAATCAAATAGTCCACAAATAAACCTTTACATTATGGTCAGTTGAT
TTTCAACAATGGTGCTAAAACAATCCATGGGGAAAGGGTAATCTTTCAATGAATGATGTGGGAGGGAAAAAAAAGA
ACTTTGATTCTTACCTCACATCACACATAAAAATTGATTTAAGTGGATCATAGACCTAAATATAAAAGCTAAAACTA
TAAATTTCAGAAGAAAAAGAGGAAAATCTTTTGATATTAAGTTAAGCAAAGTTTGCTTAGATATGACGCTAAAATCG
TGATCTATAAAAGAAAAAATTGATAGTTGACATAATAGAAATTTAAAGCTTTTAGTTCATGTATTGAAAC
```

FIGURE 1F

SEQ ID NO:66; LOC730139 transcript

\>gi|113414765|ref|XM_001134281.1| PREDICTED: Homo sapiens hypothetical
protein LOC730139 (LOC730139), mRNA
TGAGGGGTGGAGGGCAGAGGAGAAACTGCGTCAGGGATGTGTCCGCCACCTTCATCCTCCAGACGGGACT
TGGGAGCGGCTGCAGGAAACCCTGAGAGATTCCTCTTTAGGGAAGTCATCCAGCCCTGGGGTCCCCTTAT
GCCGGGAGCAGTGAGGACAGAAGAATGACCATCTATCTTGCTGAAAGCTCTGTGAGGGAGGAACGGAAGA
ACGGAGGGAGCTACGACCTTGACCATCCCCTGAGTGTCCATGGCCTCTGTGCTCCGGATGATGCCGGGGC
TGCCAGGGACCACAGAGCCACCCACTGGGAGGCTGGGGGTTGGCCTGGCTCAGGGGCGTTCGTCAGCCAT
AGACACCCACAGCATGTGGTGGGCAGGGCTGGGAGGTGACACAGGAACTGAAAAACCTGAGAAGCTCCAG
CCACTCCGCAGGGTAAGTGCCACCTGGGGTAAAATGATTAGCTGGTTCCAGCCCCTCCGCAGGGTAAGTG
GCACCTGGGGTAAAATGACTGCCTGGAGCTGGCAGCTGCTTTCTCTGCTCTCCCCAGGGCCCTGCAGGGA
AGCGTGGAAAGGCGGCACAGGGCTGGACCCAGAGGAGCTCTCAGATGCTGGACTGGACTGTTTCAGGGGT
CATCTAGCCCATTCCCCGCCTCCAGGCGAGGATTTGCTTGAGCCTGGAAAGATGAAGGATCCTCCCAGTG
CCGTCAAGCCCCGGATTCCACCTCCCTGTAGGTGGACTGCCAGCGCAGGCCCTGACAACGCAGAGAAAGA
CACAGGACCCAGCTGGGCCAGTGACAGCAGGAGCTCCTGGTGCCACAGGTGAGGGTGGGGACGCCTGGAG
CACCATGGGGGTCCTGGTTTAGTCTACAGCAGGGTCTTAAAATAGGATGTAAGTGTTACATCTTGACACA
GTGTACACATGCTGACACATATTAAAACAAATTTTACACAGCA

FIGURE 1G

SEQ ID NO:99 TNFSF12-TNFSF13 transcript

\>gi|47519573|ref|NM_172089.2| Homo sapiens TNFSF12-TNFSF13 readthrough
(TNFSF12-TNFSF13), mRNA
ATCCCTCGGGTCCCGGGATGGGGGGGCGGTGAGGCAGGCACAGCCCCCGCCCCCATGGCCGCCCGTCGG
AGCCAGAGGCGGAGGGGGCGCCGGGGGGAGCCGGGCACCGCCCTGCTGGTCCCGCTCGCGCTGGGCCTGG
GCCTGGCGCTGGCCTGCCTCGGCCTCCTGCTGGCCGTGGTCAGTTTGGGGAGCCGGGCATCGCTGTCCGC
CCAGGAGCCTGCCCAGGAGGAGCTGGTGGCAGAGGAGGACCAGGACCCGTCGGAACTGAATCCCCAGACA
GAAGAAAGCCAGGATCCTGCGCCTTTCCTGAACCGACTAGTTCGGCCTCGCAGAAGTGCACCTAAAGGCC
GGAAAACACGGGCTCGAAGAGCGATCGCAGCCCATTATGAAGTTCATCCACGACCTGGACAGGACGGAGC
GCAGGCAGGTGTGGACGGGACAGTGAGTGGCTGGAGGAAGCCAGAATCAACAGCTCCAGCCCTCTGCGC
TACAACCGCCAGATCGGGGAGTTTATAGTCACCCGGGCTGGGCTCTACTACCTGTACTGTCAGAGTTCCG
ATGCCCTGGAAGCCTGGGAGAATGGGGAGAGATCCCGGAAAAGGAGAGCAGTGCTCACCCAAAAACAGAA
GAAGCAGCACTCTGTCCTGCACCTGGTTCCCATTAACGCCACCTCCAAGGATGACTCCGATGTGACAGAG
GTGATGTGGCAACCAGCTCTTAGGCGTGGGAGAGGCCTACAGGCCCAAGGATATGGTGTCCGAATCCAGG
ATGCTGGAGTTTATCTGCTGTATAGCCAGGTCCTGTTTCAAGACGTGACTTTCACCATGGGTCAGGTGGT
GTCTCGAGAAGGCCAAGGAAGGCAGGAGACTCTATTCCGATGTATAAGAAGTATGCCCTCCCACCCGGAC
CGGGCCTACAACAGCTGCTATAGCGCAGGTGTCTTCCATTTACACCAAGGGGATATTCTGAGTGTCATAA
TTCCCCGGGCAAGGGCGAAACTTAACCTCTCTCCACATGGAACCTTCCTGGGGTTTGTGAAACTGTGATT
GTGTTATAAAAAGTGGCTCCCAGCTTGGAAGACCAGGGTGGGTACATACTGGAGACAGCCAAGAGCTGAG
TATATAAAGGAGAGGGAATGTGCAGGAACAGAGGCGTCTTCCTGGGTTTGGCTCCCCGTTCCTCACTTTT
CCCTTTTCATTCCCACCCCCTAGACTTTGATTTTACGGATATCTTGCTTCTGTTCCCCATGGAGCTCCGA
ATTCTTGCGTGTGTGTAGATGAGGGGCGGGGACGGGCGCCAGGCATTGTCCAGACCTGGTCGGGGCCCA
CTGGAAGCATCCAGAACAGCACCACCATCTAGCGGCCGCTCGAGGGAAGCACCCGCCGGTTGGCCGAAGT
CCACGAAGCCGCCCTCTGCTAGGGAAAACCCCTGGTTCTCCATGCCACACCTCTCTCCAGGTGCCCTCTG
CCTCTTCACCCCACAAGAAGCCTTATCCTACGTCCTTCTCTCCATCTATCGGACCCCAGTTTCCATCACT
ATCTCCAGAGATGTAGCTATTATGCGCCCGTCTACAGGGGTGCCCGACGATGACGGTGCCTTCGCAGTC
AAATTACTCTTCGGGTCCCAAGGTTTGGCTTTCACGCGCTCCATTGCCCGGCGTGGCAGGCCATTCCAA
GCCCTTCCGGGCTGGAACTGGTGTCGGAGGAGCCTCGGGTGTATCGTACGCCCTGGTGTTGGTGTTGCCT
CACTCCTCTGAGCTCTTCTTTCTGATCAAGCCCTGCTTAAAGTTAAATAAAATAGAATGAATGATACCCC
GGCAAAAAAAAAAAAAAAAAA

FIGURE 1H

SEQ ID NO:100; *TNFSF13* transcript variant alpha

```
>gi|211938416|ref|NM_003808.3| Homo sapiens tumor necrosis factor (ligand)
superfamily, member 13 (TNFSF13), transcript variant alpha, mRNA
CCGGAACCCTGTGTGCTGGGGAGGAATCCCGCAGTGGCCGGGGGCTTGAGGCCGCTGCTTTGTCTCTTC
GTCCAGAGCCTTATGTAAGAGCTTTTCTCGGGAAACAGGAAGTCCTGCTTGCCAATTTCAGCACAGGGAG
TAGTGCAGGCCTTATTCCAACACACCCGGCCCAGCCTTAACCCCAGAACTCAGCCAGTTTCTTGCTTCCG
TGCCCCTGGTTCTCCTCCCCATCGAGCCCACCCCTCCTTTCCCACCTTCAGTCACCCCTAGTGAACTGCC
CCAGCGATCTCTGCTGTGCTTGACCCCGAGGGTCTTCCACCCTCGCCCTGACCCTGGACACTGCCCAGCT
TGGCCCCCCATCCTGCTCCTGGCACAATGCCCTCTAGCCAGCCAACCTTCCCTCCCCCAACCCTGGGGCC
GCCCCAGGGTTCCTGCGCACTGCCTGTTCCTCCTGGGTGTCACTGGCAGCCCTGTCCTTCCTAGAGGGAC
TGGAACCTAATTCTCCTGAGGCTGAGGGAGGGTGGAGGGTCTCAAGGCAACGCTGGCCCCACGACGGAGT
GCCAGGAGCACTAACAGTACCCTTAGCTTGCTTTCCTCCTCCCTCCTTTTTATTTTCAAGTTCCTTTTTA
TTTCTCCTTGCGTAACAACCTTCTTCCCTTCTGCACCACTGCCCGTACCCTTACCCGCCCCGCCACCTCC
TTGCTACCCCACTCTTGAAACCACAGCTGTTGGCAGGGTCCCCAGCTCATGCCAGCCTCATCTCCTTTCT
TGCTAGCCCCCAAAGGGCCTCCAGGCAACATGGGGGGCCCAGTCAGAGAGCCGGCACTCTCAGTTGCCCT
CTGGTTGAGTTGGGGGGCAGCTCTGGGGCCGTGGCTTGTGCCATGGCTCTGCTGACCCAACAAACAGAG
CTGCAGAGCCTCAGGAGAGAGGTGAGCCGGCTGCAGGGACAGGAGGCCCCTCCCAGAATGGGGAAGGGT
ATCCCTGGCAGAGTCTCCCGGAGCAGAGTTCCGATGCCCTGGAAGCCTGGGAGAATGGGGAGAGATCCCG
GAAAAGGAGAGCAGTGCTCACCCAAAAACAGAAGAAGCAGCACTCTGTCCTGCACCTGGTTCCCATTAAC
GCCACCTCCAAGGATGACTCCGATGTGACAGAGGTGATGTGGCAACCAGCTCTTAGGCGTGGGAGAGGCC
TACAGGCCCAAGGATATGGTGTCCGAATCCAGGATGCTGGAGTTTATCTGCTGTATAGCCAGGTCCTGTT
TCAAGACGTGACTTTCACCATGGGTCAGGTGGTGTCTCGAGAAGGCCAAGGAAGGCAGGAGACTCTATTC
CGATGTATAAGAAGTATGCCCTCCCACCCGGACCGGGCCTACAACAGCTGCTATAGCGCAGGTGTCTTCC
ATTTACACCAAGGGGATATTCTGAGTGTCATAATTCCCGGGCAAGGGCGAAACTTAACCTCTCTCCACA
TGGAACCTTCCTGGGGTTTGTGAAACTGTGATTGTGTTATAAAAAGTGGCTCCCAGCTTGGAAGACCAGG
GTGGGTACATACTGGAGACAGCCAAGAGCTGAGTATATAAAGGAGAGGGAATGTGCAGGAACAGAGGCGT
CTTCCTGGGTTTGGCTCCCCGTTCCTCACTTTTCCCTTTTCATTCCCACCCCCTAGACTTTGATTTTACG
GATATCTTGCTTCTGTTCCCCATGGAGCTCCGAATTCTTGCGTGTGTGTAGATGAGGGGCGGGGGACGGG
CGCCAGGCATTGTCCAGACCTGGTCGGGGCCCACTGGAAGCATCCAGAACAGCACCACCATCTAGCGGCC
GCTCGAGGGAAGCACCCGCCGGTTGGCCGAAGTCCACGAAGCCGCCCTCTGCTAGGGAAAACCCCTGGTT
CTCCATGCCACACCTCTCTCCAGGTGCCCTCTGCCTCTTCACCCCACAAGAAGCCTTATCCTACGTCCTT
CTCTCCATCTATCGGACCCCAGTTTCCATCACTATCTCCAGAGATGTAGCTATTATGCGCCCGTCTACAG
GGGGTGCCCGACGATGACGGTGCCTTCGCAGTCAAATTACTCTTCGGGTCCCAAGGTTTGGCTTTCACGC
GCTCCATTGCCCCGGCGTGGCAGGCCATTCCAAGCCCTTCCGGGCTGGAACTGGTGTCGGAGGAGCCTCG
GGTGTATCGTACGCCCTGGTGTTGGTGTTGCCTCACTCCTCTGAGCTCTTCTTTCTGATCAAGCCCTGCT
TAAAGTTAAATAAAATAGAATGAATGATACCCCGGCAAAAAAAAAAAAAAAAA
```

FIGURE 1I

SEQ ID NO:101; *TNFSF13* transcript variant beta

```
>gi|211938417|ref|NM_172087.2| Homo sapiens tumor necrosis factor (ligand)
superfamily, member 13 (TNFSF13), transcript variant beta, mRNA
CCGGAACCCTGTGTGCTGGGGAGGAATCCCGCAGTGGCCGGGGGCTTGAGGCCGCTGCTTTGTCTCTTC
GTCCAGAGCCTTATGTAAGAGCTTTTCTCGGGAAACAGGAAGTCCTGCTTGCCAATTTCAGCACAGGGAG
TAGTGCAGGCCTTATTCCAACACACCCGGCCCAGCCTTAACCCCAGAACTCAGCCAGTTTCTTGCTTCCG
TGCCCCTGGTTCTCCTCCCCATCGAGCCCACCCCTCCTTTCCCACCTTCAGTCACCCCTAGTGAACTGCC
CCAGCGATCTCTGCTGTGCTTGACCCCGAGGGTCTTCCACCCTCGCCCTGACCCTGGACACTGCCCAGCT
TGGCCCCCCATCCTGCTCCTGGCACAATGCCCTCTAGCCAGCCAACCTTCCCTCCCCCAACCCTGGGGCC
GCCCCAGGGTTCCTGCGCACTGCCTGTTCCTCCTGGGTGTCACTGGCAGCCCTGTCCTTCCTAGAGGGAC
TGGAACCTAATTCTCCTGAGGCTGAGGGAGGGTGGAGGGTCTCAAGGCAACGCTGGCCCCACGACGGAGT
GCCAGGAGCACTAACAGTACCCTTAGCTTGCTTTCCTCCTCCCTCCTTTTTATTTTCAAGTTCCTTTTTA
TTTCTCCTTGCGTAACAACCTTCTTCCCTTCTGCACCACTGCCCGTACCCTTACCCGCCCCGCCACCTCC
```

FIGURE 1I (Continued)

```
TTGCTACCCCACTCTTGAAACCACAGCTGTTGGCAGGGTCCCCAGCTCATGCCAGCCTCATCTCCTTTCT
TGCTAGCCCCCAAAGGGCCTCCAGGCAACATGGGGGGCCCAGTCAGAGAGCCGGCACTCTCAGTTGCCCT
CTGGTTGAGTTGGGGGGCAGCTCTGGGGGCCGTGGCTTGTGCCATGGCTCTGCTGACCCAACAAACAGAG
CTGCAGAGCCTCAGGAGAGAGGTGAGCCGGCTGCAGGGGACAGGAGGCCCCTCCCAGAATGGGGAAGGGT
ATCCCTGGCAGAGTCTCCCGGAGCAGAGTTCCGATGCCCTGGAAGCCTGGGAGAATGGGGAGAGATCCCG
GAAAAGGAGAGCAGTGCTCACCCAAAAACAGAAGAATGACTCCGATGTGACAGAGGTGATGTGGCAACCA
GCTCTTAGGCGTGGGAGAGGCCTACAGGCCCAAGGATATGGTGTCCGAATCCAGGATGCTGGAGTTTATC
TGCTGTATAGCCAGGTCCTGTTTCAAGACGTGACTTTCACCATGGGTCAGGTGGTGTCTCGAGAAGGCCA
AGGAAGGCAGGAGACTCTATTCCGATGTATAAGAAGTATGCCCTCCCACCCGGACCGGGCCTACAACAGC
TGCTATAGCGCAGGTGTCTTCCATTTACACCAAGGGGATATTCTGAGTGTCATAATTCCCCGGGCAAGGG
CGAAACTTAACCTCTCTCCACATGGAACCTTCCTGGGGTTTGTGAAACTGTGATTGTGTTATAAAAAGTG
GCTCCCAGCTTGGAAGACCAGGGTGGGTACATACTGGAGACAGCCAAGAGCTGAGTATATAAAGGAGAGG
GAATGTGCAGGAACAGAGGCGTCTTCCTGGGTTTGGCTCCCCGTTCCTCACTTTTCCCTTTTCATTCCCA
CCCCCTAGACTTTGATTTTACGGATATCTTGCTTCTGTTCCCCATGGAGCTCCGAATTCTTGCGTGTGTG
TAGATGAGGGCGGGGACGGGCGCCAGGCATTGTCCAGACCTGGTCGGGGCCCACTGGAAGCATCCAGA
ACAGCACCACCATCTAGCGGCCGCTCGAGGGAAGCACCCGCCGGTTGGCCGAAGTCCACGAAGCCGCCCT
CTGCTAGGGAAAACCCCTGGTTCTCCATGCCACACCTCTCTCCAGGTGCCCTCTGCCTCTTCACCCCACA
AGAAGCCTTATCCTACGTCCTTCTCTCCATCTATCGGACCCCAGTTTCCATCACTATCTCCAGAGATGTA
GCTATTATGCGCCCGTCTACAGGGGGTGCCCGACGATGACGGTGCCTTCGCAGTCAAATTACTCTTCGGG
TCCCAAGGTTTGGCTTTCACGCGCTCCATTGCCCCGGCGTGGCAGGCCATTCCAAGCCCTTCCGGGCTGG
AACTGGTGTCGGAGGAGCCTCGGGTGTATCGTACGCCCTGGTGTTGGTGTTGCCTCACTCCTCTGAGCTC
TTCTTTCTGATCAAGCCCTGCTTAAAGTTAAATAAAATAGAATGAATGATACCCCGGCAAAAAAAAAAAA
AAAAA
```

FIGURE 1J

SEQ ID NO:102; *TNFSF13* transcript variant gamma

```
>gi|211938415|ref|NM_172088.2| Homo sapiens tumor necrosis factor (ligand)
superfamily, member 13 (TNFSF13), transcript variant gamma, mRNA
CCGGAACCCTGTGTGCTGGGGAGGAATCCCGCAGTGGCCGGGGGGCTTGAGGCCGCTGCTTTGTCTCTTC
GTCCAGAGCCTTATGTAAGAGCTTTTCTCGGGAAACAGGAAGTCCTGCTTGCCAATTTCAGCACAGGGAG
TAGTGCAGGCCTTATTCCAACACACCCGGCCCAGCCTTAACCCCAGAACTCAGCCAGTTTCTTGCTTCCG
TGCCCCTGGTTCTCCTCCCCATCGAGCCCACCCCTCCTTTCCCACCTTCAGTCACCCCTAGTGAACTGCC
CCAGCGATCTCTGCTGTGCTTGACCCCGAGGGTCTTCCACCCTCGCCCTGACCCTGGACACTGCCCAGCT
TGGCCCCCCATCCTGCTCCTGGCACAATGCCCTCTAGCCAGCCAACCTTCCCTCCCCCAACCCTGGGGCC
GCCCCAGGGTTCCTGCGCACTGCCTGTTCCTCCTGGGTGTCACTGGCAGCCCTGTCCTTCCTAGAGGGAC
TGGAACCTAATTCTCCTGAGGCTGAGGGAGGGTGGAGGGTCTCAAGGCAACGCTGGCCCCACGACGGAGT
GCCAGGAGCACTAACAGTACCCTTAGCTTGCTTTCCTCCTCCCTCCTTTTTATTTTCAAGTTCCTTTTTA
TTTCTCCTTGCGTAACAACCTTCTTCCCTTCTGCACCACTGCCCGTACCCTTACCCGCCCCGCCACCTCC
TTGCTACCCCACTCTTGAAACCACAGCTGTTGGCAGGGTCCCCAGCTCATGCCAGCCTCATCTCCTTTCT
TGCTAGCCCCCAAAGGGCCTCCAGGCAACATGGGGGCCCAGTCAGAGAGCCGGCACTCTCAGTTGCCCT
CTGGTTGAGTTGGGGGGCAGCTCTGGGGGCCGTGGCTTGTGCCATGGCTCTGCTGACCCAACAAACAGAG
CTGCAGAGCCTCAGGAGAGAGGTGAGCCGGCTGCAGGGACAGGAGGCCCCTCCCAGAATGGGGAAGGGT
ATCCCTGGCAGAGTCTCCCGGAGCAGAGTTCCGATGCCCTGGAAGCCTGGGAGAATGGGGAGAGATCCCG
GAAAAGGAGAGCAGTGCTCACCCAAAAACAGAAGAAGCAGCACTCTGTCCTGCACCTGGTTCCCATTAAC
GCCACCTCCAAGGATGACTCCGATGTGACAGAGGTGATGTGGCAACCAGCTCTTAGGCGTGGGAGAGGCC
TACAGGCCCAAGGATATGGTGTCCGAATCCAGGATGCTGGAGTTTATCTGCTGTATAGCCAGGTCCTGTT
TCAAGACGTGACTTTCACCATGGGTCAGGTGGTGTCTCGAGAAGGCCAAGGAAGGCAGGAGACTCTATTC
CGATGTATAAGAAGTATGCCCTCCCACCCGGACCGGGCCTACAACAGCTGCTATAGCGCAGGTGTCTTCC
ATTTACACCAAGGGGATATTCTGAGTGTCATAATTCCCCGGGCAAGGGCGAAACTTAACCTCTCTCCACA
TGGAACCTTCCTGGGACTTTGATTTTACGGATATCTTGCTTCTGTTCCCCATGGAGCTCCGAATTCTTGC
GTGTGTGTAGATGAGGGGCGGGGACGGGCGCCAGGCATTGTCCAGACCTGGTCGGGGCCCACTGGAAGC
ATCCAGAACAGCACCACCATCTAGCGGCCGCTCGAGGGAAGCACCCGCCGGTTGGCCGAAGTCCACGAAG
CCGCCCTCTGCTAGGGAAAACCCCTGGTTCTCCATGCCACACCTCTCTCCAGGTGCCCTCTGCCTCTTCA
CCCCACAAGAAGCCTTATCCTACGTCCTTCTCTCCATCTATCGGACCCCAGTTTCCATCACTATCTCCAG
AGATGTAGCTATTATGCGCCCGTCTACAGGGGGTGCCCGACGATGACGGTGCCTTCGCAGTCAAATTACT
CTTCGGGTCCCAAGGTTTGGCTTTCACGCGCTCCATTGCCCCGGCGTGGCAGGCCATTCCAAGCCCTTCC
GGGCTGGAACTGGTGTCGGAGGAGCCTCGGGTGTATCGTACGCCCTGGTGTTGGTGTTGCCTCACTCCTC
TGAGCTCTTCTTTCTGATCAAGCCCTGCTTAAAGTTAAATAAAATAGAATGAATGATACCCCGGCAAAAA
AAAAAAAAAAA
```

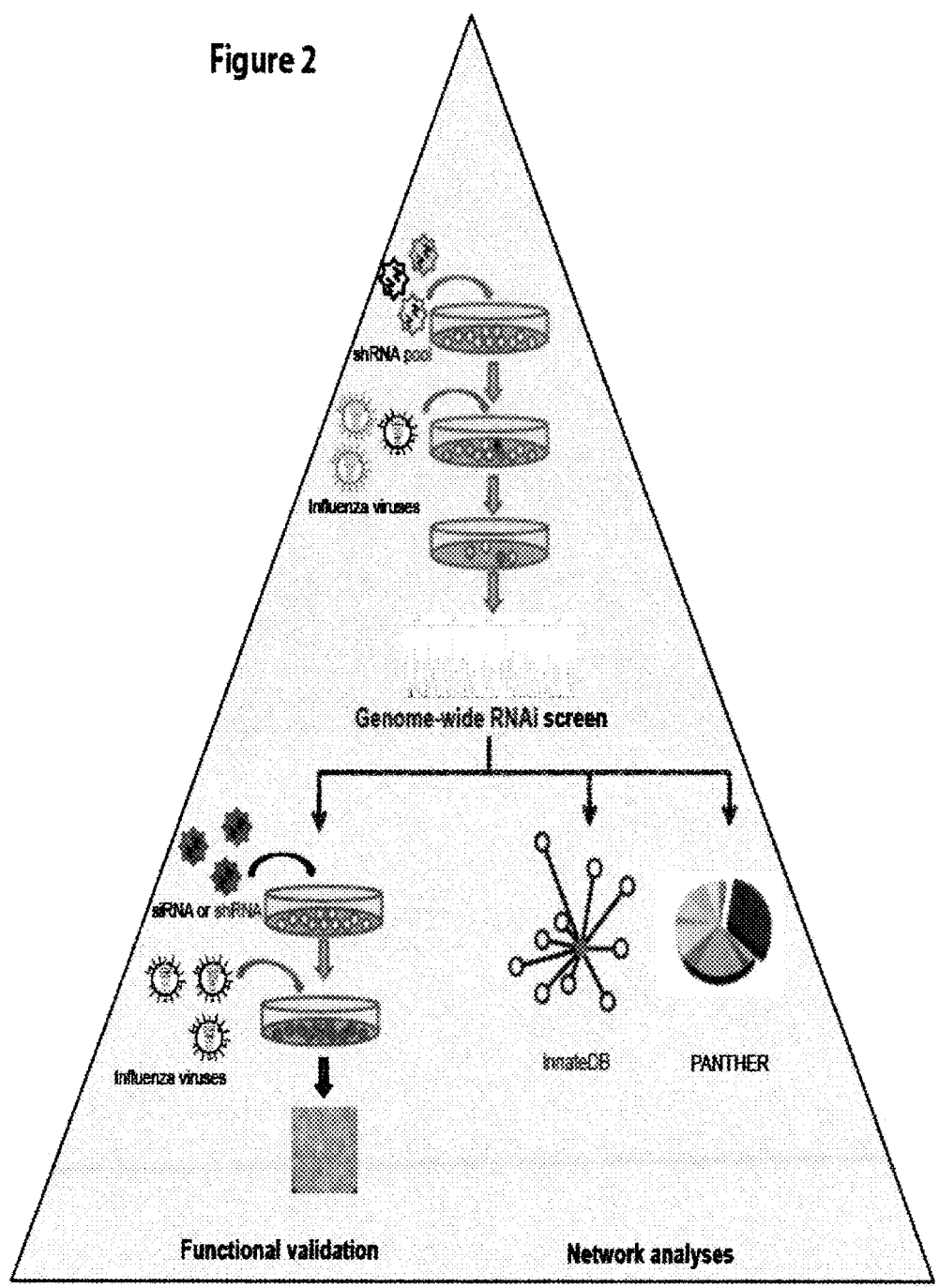

FIGURE 9a
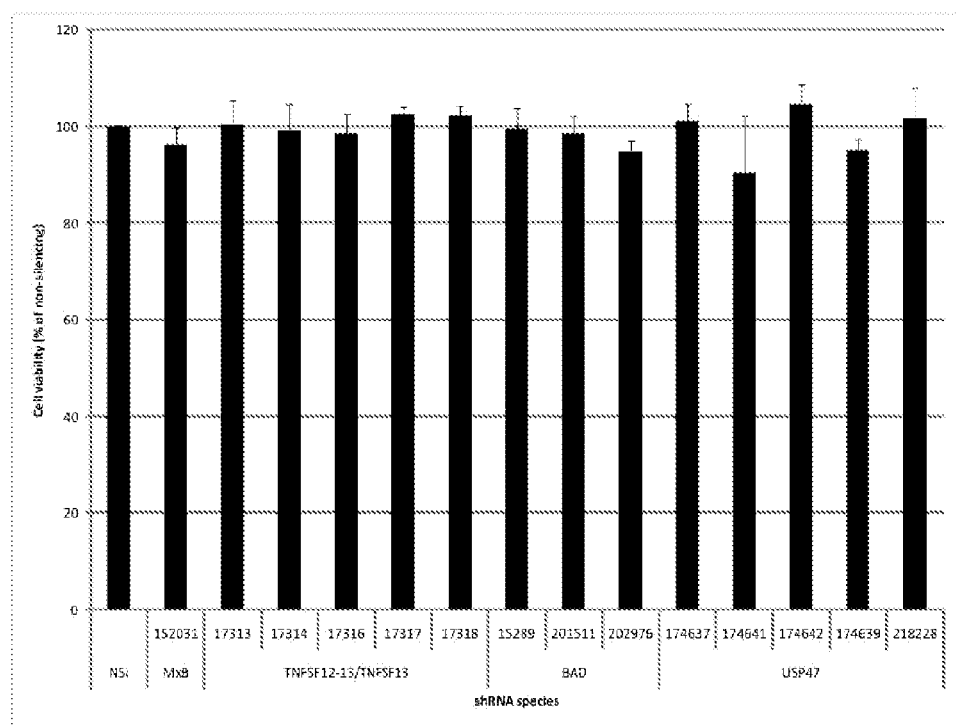
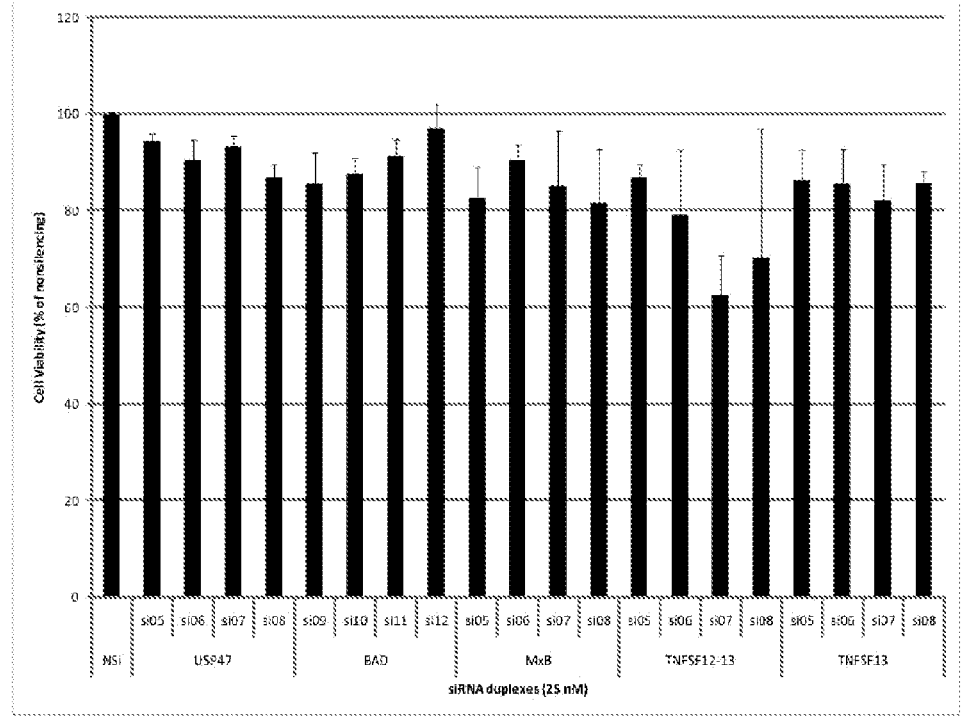
FIGURE 9b

FIGURE 10a
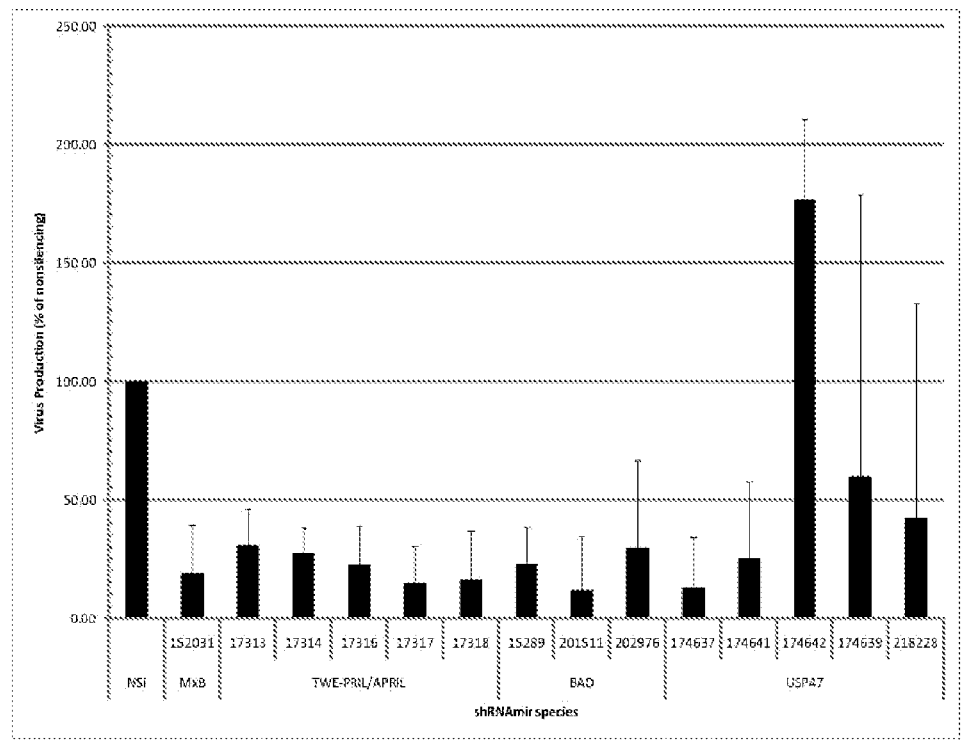
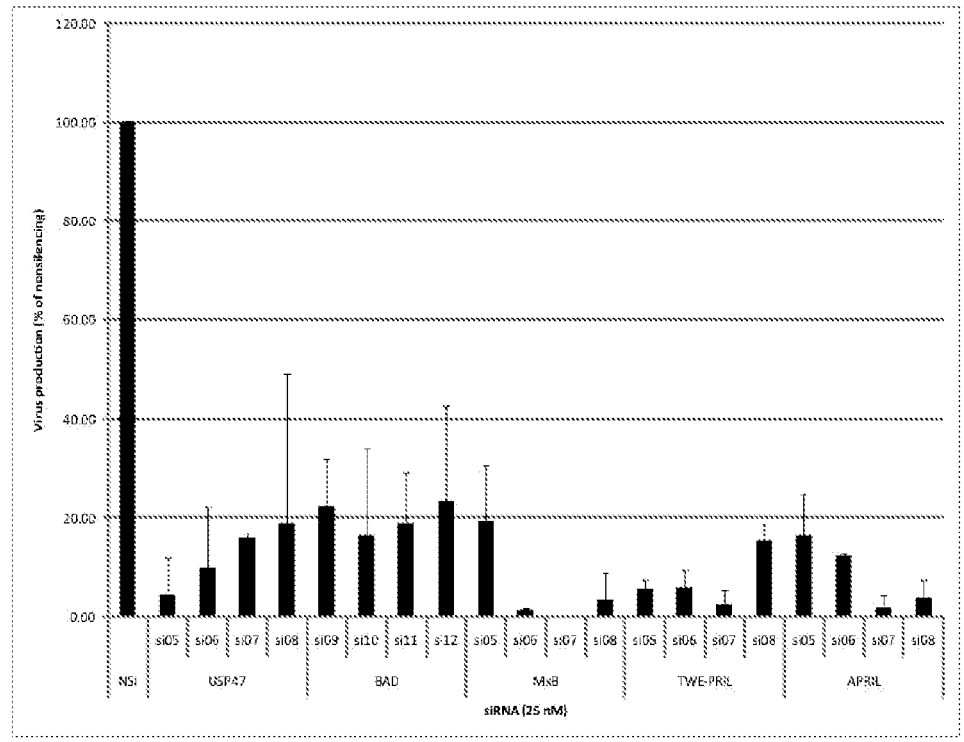
FIGURE 10b

TARGET HOST FACTORS FOR TREATING VIRAL INFECTION

TECHNICAL FIELD

The present disclosure relates to methods and compositions for treating viral infection by manipulating expression of a target sequence. The methods and compositions may, for example, be useful in treating virus infection and/or reducing virus replication and/or virus-mediated cytotoxicity.

BACKGROUND

Infections from influenza viruses pose potentially catastrophic global economic and health threats. Most current therapeutic strategies are directed at viral entry prevention, such as vaccination. These strategies face challenges because viruses display considerable antigenic malleability which enable then to circumvent innate and/or acquired immunity.

Influenza viruses pose a significant threat to the world population as causative agents in seasonal epidemics that claim many lives annually. Furthermore pandemic outbreaks of influenza can have a significant health and economic impact. The emergence of highly-pathogenic avian influenza virus H5N1 and the pandemic outbreak of swine-origin H1N1 influenza virus (SOIV) strongly signals the need for further investigation of this complex virus and its pathogenicity.

Consequently, developing strategies for preventing and treating viral infection is desirable. New and effective compositions are needed to prevent and treat influenza virus infection.

SUMMARY

The present invention relates to methods and compositions for treating viral infection by manipulating expression of a target sequence. The methods and compositions may be useful in treating virus infection and/or reducing virus replication and/or virus-mediated cytotoxicity.

According to the present disclosure there is provided a method of reducing virus replication comprising contacting virus-infected cells with an effective amount of at least one inhibitor of ABI2, ARRDC3, BAD, BRCA1, C17orf85, C1orf71, C6orf162, CCNJL, CFL1, GON4L, HCG 1986447, HIST1H2AB, HPS4, LHX8, RPS25, RPL23, RPL32, LOC730139, LRRC39, MALT1, MX1, MERTK, MX2, NRG1, OR52A1, PLEKHH1, PTPN13, PTPRJ, RLN1, RNF19A, SH3BP4, SLC7A14, ST8SIA3, STX3, TMC6, TMTC4, TNFSF12-INFSF13, TNFSF13, TTN, UBXN7, USP47, WNK2, YPEL2, ZNF251 and/or SCG2.

The present disclosure also provides a method of reducing virus-mediated cytotoxicity comprising contacting virus-infected cells with an effective amount of at least one inhibitor of ABI2, ARRDC3, BAD, BRCA1, C17orf85, C1orf71, C6orf162, CCNJL, CFL1, GON4L, HCG 1986447, HIST1H2AB, HPS4, RPS25, RPL23, RPL32, LOC730139, LRRC39, MALT1, MX1, MERTK, MX2, NRG1, OR52A1, PLEKHH1, PTPN13, PTPRJ, RLN1, RNF19A, SH3BP4, SLC7A14, ST8SIA3, STX3, TMC6, TMTC4, TNFSF12-TNFSF13, TNFSF13, TTN, UBXN7, USP47, WNK2, YPEL2, ZNF251 and/or SCG2.

The present disclosure further provides a method for treating a viral infection in a subject comprising administering to the subject a composition comprising at least one inhibitor of ABI2, ARRDC3, BAD, BRCA1, C17orf85, C1orf71, C6orf162, CCNJL, CFL1, GON4L, HCG 1986447, HIST1H2AB, HPS4, LHX8, RPS25, RPL23, RPL32, LOC730139, LRRC39, MALT1, MX1, MERTK, MX2, NRG1, OR52A1, PLEKHH1, PTPN13, PTPRJ, RLN1, RNF19A, SH3BP4, SLC7A14, ST8SIA3, STX3, TMC6, TMTC4, TNFSF12-TNFSF13, TNFSF13, TTN, UBXN7, USP47, WNK2, YPEL2, ZNF251 and/or SCG2, wherein the composition reduces expression or activity of the ABI2, ARRDC3, BAD, BRCA1, C17orf85, C1orf71, C6orf162, CCNJL, CFL1, GON4L, HCG 1986447, HIST1H2AB, HPS4, LHX8, RPS25, RPL23, RPL32, LOC730139, LRRC39, MALT1, MX1, MERTK, MX2, NRG1, OR52A1, PLEKHH1, PTPN13, PTPRJ, RLN1, RNF19A, SH3BP4, SLC7A14, ST8SIA3, STX3, TMC6, TMTC4, TNFSF12-TNFSF13, TNFSF13, TTN, UBXN7, USP47, WNK2, YPEL2, ZNF251 and/or SCG2 when administered to the subject.

In the methods as described above the inhibitor may be selected from siRNA, RNAi, shRNA, antisense RNA, antisense DNA, decoy molecule, decoy DNA, double stranded DNA, single-stranded DNA, complexed DNA, encapsulated DNA, viral DNA, plasmid DNA, naked RNA, encapsulated RNA, viral RNA, double stranded RNA, molecules capable of generating RNA interference, synthetic ligands, peptide ligands, antagonists, agonists, antibodies, small chemical molecules and combinations thereof.

Furthermore in the methods as described above the siRNA may have a sequence selected from the group of SEQ ID NO: 6, SEQ ID NO: 7, SEQ ID NO: 8, SEQ ID NO: 9, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 26, SEQ ID NO: 27, SEQ ID NO: 28, SEQ ID 29, SEQ ID NO: 36, SEQ ID 37, SEQ ID NO: 38, SEQ ID 39 and combinations thereof and the shRNA may have a sequence selected from the group of SEQ ID NO: 1 to SEQ ID NO: 5, SEQ ID NO: 11 to SEQ ID NO: 15, SEQ ID NO: 25, SEQ ID NO: 31 to SEQ ID NO: 35, SEQ ID NO: 40 to SEQ ID NO: 45, SEQ ID NO: 47 to SEQ ID NO: 65, SEQ ID NO: 67 to SEQ ID NO: 98, and combinations thereof.

Furthermore the ABI2, ARRDC3, BAD, BRCA1, C17orf85, C1orf71, C6orf162, CCNJL, CFL1, GON4L, HCG 1986447, HIST1H2AB, HPS4, LHX8, RPS25, RPL23, RPL32, LOC730139, LRRC39, MALT1, MX1, MERTK, MX2, NRG1, OR52A1, PLEKHH1, PTPN13, PTPRJ, RLN1, RNF19A, SH3BP4, SLC7A14, ST8SIA3, STX3, TMC6, TMTC4, TNFSF12-TNFSF13, TNFSF13, TTN, UBXN7, USP47, WNK2, YPEL2, ZNF251 and/or SCG2 inhibitor may act on a polypeptide, DNA, or RNA.

In the methods as described above the cells may be contacted by the inhibitor in vivo and the subject may be a mammal. More specifically the mammal may be a human. Furthermore the virus in the methods described may be an influenza virus.

The present disclosure further provides a method of screening for an agent useful for reducing virus to production and/or reducing virus-mediated cytotoxicity in a cell comprising:

i) contacting a cell expressing ABI2, ARRDC3, BAD, BRCA1, C17orf85, C1orf71, C6orf162, CCNJL, CFL1, GON4L, HCG 1986447, HIST1H2AB, HPS4, LHX8, RPS25, RPL23, RPL32, LOC730139, LRRC39, MALT1, MX1, MERTK, MX2, NRG1, OR52A1, PLEKHH1, PTPN13, PTPRJ, RLN1, RNF19A, SH3BP4, SLC7A14, ST8SIA3, STX3, TMC6, TMTC4, TNFSF12-TNFSF13, TNFSF13, TTN, UBXN7, USP47, WNK2, YPEL2, ZNF251 and/or SCG2 with a test compound;

ii) comparing the amount of ABI2, ARRDC3, BAD, BRCA1, C17orf85, C1orf71, C6orf162, CCNJL, CFL1, GON4L, HCG 1986447, HIST1H2AB, HPS4, LHX8, RPS25, RPL23, RPL32, LOC730139, LRRC39, MALT1, MX1, MERTK, MX2, NRG1, OR52A1, PLEKHH1, PTPN13, PTPRJ, RLN1, RNF19A, SH3BP4, SLC7A14, ST8SIA3, STX3, TMC6, TMTC4, TNFSF12-TNFSF13, TNFSF13, TTN, UBXN7, USP47, WNK2, YPEL2, ZNF251 and/or SCG2 in the cell in the presence and absence of the test compound; and iii) selecting any test compound decreasing the amount of ABI2, ARRDC3, BAD, BRCA1, C17orf85, C1orf71, C6orf162, CCNJL, CFL1, GON4L, HCG 1986447, HIST1H2AB, HPS4, LHX8, RPS25, RPL23, RPL32, LOC730139, LRRC39, MALT1, MX1, MERTK, MX2, NRG1, OR52A1, PLEKHH1, PTPN13, PTPRJ, RLN1, RNF19A, SH3BP4, SLC7A14, ST8SIA3, STX3, TMC6, TMTC4, TNFSF12-TNFSF13, TNFSF13, TTN, UBXN7, USP47, WNK2, YPEL2, ZNF251 and/or SCG2 as useful for reducing virus production and/or reducing virus-mediated cytotoxicity.

In addition a siRNA for treating virus infection is provided. The siRNA may comprise a sequence represented by SEQ ID NO: 6, SEQ ID NO: 7, SEQ ID NO: 8, SEQ ID NO: 9, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 26, SEQ ID NO: 27, SEQ ID NO: 28, SEQ ID 29, SEQ ID NO: 36, SEQ ID 37, SEQ ID NO: 38, SEQ ID 39. A shRNA for treating virus infection is also provided. The shRNA may comprise a sequence represented by SEQ ID NO: 1 to SEQ ID NO: 5, SEQ ID NO: 11 to SEQ ID NO: 15, SEQ ID NO: 25, SEQ ID NO: 31 to SEQ ID NO: 35, SEQ ID NO: 40 to SEQ ID NO: 45, SEQ ID NO: 47 to SEQ ID NO: 65, SEQ ID NO: 67 to SEQ ID NO: 98.

The present disclosure also provides a pharmaceutical formulation for treating a virus infection comprising at least one inhibitor of ABI2, ARRDC3, BAD, BRCA1, C17orf85, C1orf71, C6orf162, CCNJL, CFL1, GON4L, HCG 1986447, HIST1H2AB, HPS4, LHX8, RPS25, RPL23, RPL32, LOC730139, LRRC39, MALT1, MX1, MERTK, MX2, NRG1, OR52A1, PLEKHH1, PTPN13, PTPRJ, RLN1, RNF19A, SH3BP4, SLC7A14, ST8SIA3, STX3, TMC6, TMTC4, TNFSF12-TNFSF13, TNFSF13, TTN, UBXN7, USP47, WNK2, YPEL2, ZNF251 and/or SCG2. At least one inhibitor may be a nucleic acid and the nucleic acid may be selected from siRNA, RNAi, shRNA, or combinations thereof or from nucleic acid molecules capable of encoding siRNA, RNAi, shRNA, or combinations thereof.

The siRNA in the pharmaceutical formulation may have a sequence selected from the group of SEQ ID NO: 6, SEQ ID NO: 7, SEQ ID NO: 8, SEQ ID NO: 9, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 26, SEQ ID NO: 27, SEQ ID NO: 28, SEQ ID 29, SEQ ID NO: 36, SEQ ID 37, SEQ ID NO: 38, SEQ ID 39 and combinations thereof and the shRNA may have a sequence selected from the group SEQ ID NO: 1 to SEQ ID NO: 5, SEQ ID NO: 11 to SEQ ID NO: 15, SEQ ID NO: 25, SEQ ID NO: 31 to SEQ ID NO: 35, SEQ ID NO: 40 to SEQ ID NO: 45, SEQ ID NO: 47 to SEQ ID NO: 65, SEQ ID NO: 67 to SEQ ID NO: 98 and combinations thereof.

This summary does not necessarily describe all features of the invention. Other aspects, features and advantages of the present invention will become apparent to those of ordinary skill in the art upon review of the following description of some specific embodiments of the invention.

BRIEF DESCRIPTION OF THE DRAWINGS

These and other features of the invention will become more apparent from the following description in which reference is made to the appended drawings wherein:

FIG. 1: (A) shows the sequence of SEQ ID NO: 10. (B) shows the sequence of SEQ ID NO: 103. (C) shows the sequence of SEQ ID NO: 24. (D) shows the sequence of SEQ ID NO: 30. (E) shows the sequence of SEQ ID NO: 46. (F) shows the sequence of SEQ ID NO: 66. (G) shows the sequence of SEQ ID NO: 99. (H) shows the sequence of SEQ ID NO: 100. (I) shows the sequence of SEQ ID NO: 101. (J) shows the sequence of SEQ ID NO: 102.

FIG. 2: shows a schematic diagram of methods. Details are given in Methods Summary (Example 4).

FIG. 9 shows a graph with viability of A549 cells after (a) shRNA or (b) siRNA treatment determined by WST-1 assay. NSi=non-silencing. Error bars represent standard deviation from 2 biological replicates.

FIG. 10 shows a graph with influenza virus replication in shRNA-knockdown A549 cells infected with NY55 at MOI 1. NSi=non-silencing. Error bars represent standard deviation from 2-3 biological replicates.

DETAILED DESCRIPTION

Figure 3:
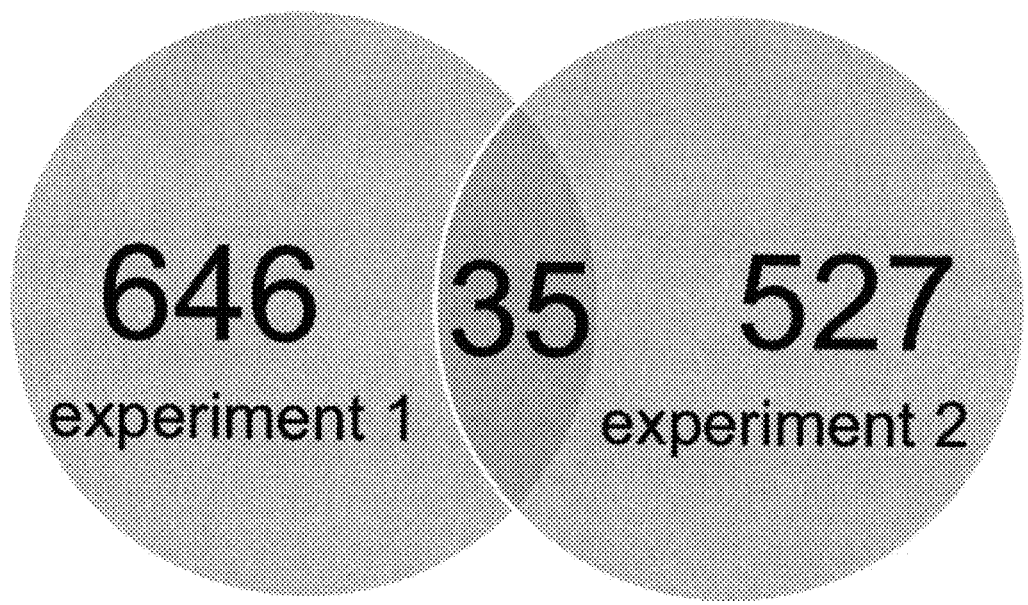
FIG. 3: shows a Venn diagram of the genes (target host factors) identified in the genome-wide RNAi screen. Unique number of genes identified in the first and second biological replicates of the high-throughput screens. 35 unique genes were identified in both experiments.
Figure 4:
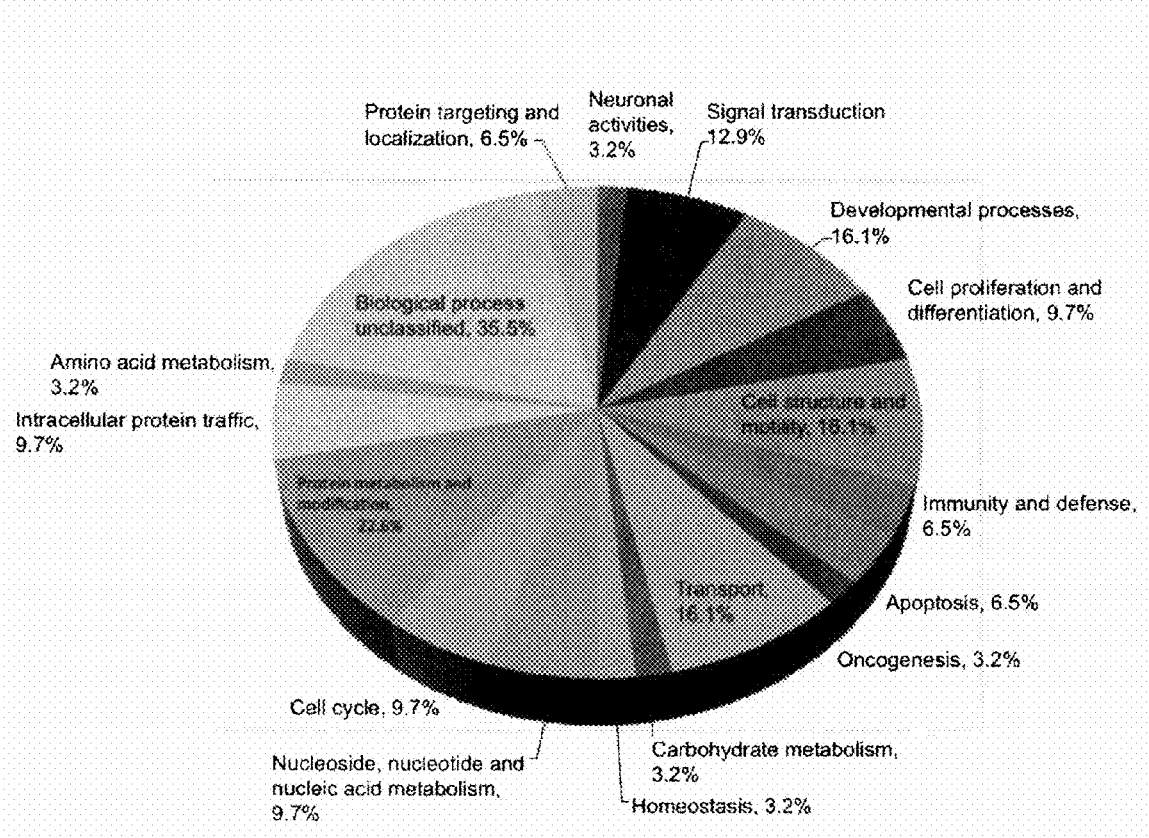
FIG. 4 shows PANTHER biological process categorization of the 35 unique genes.
Figure 5:
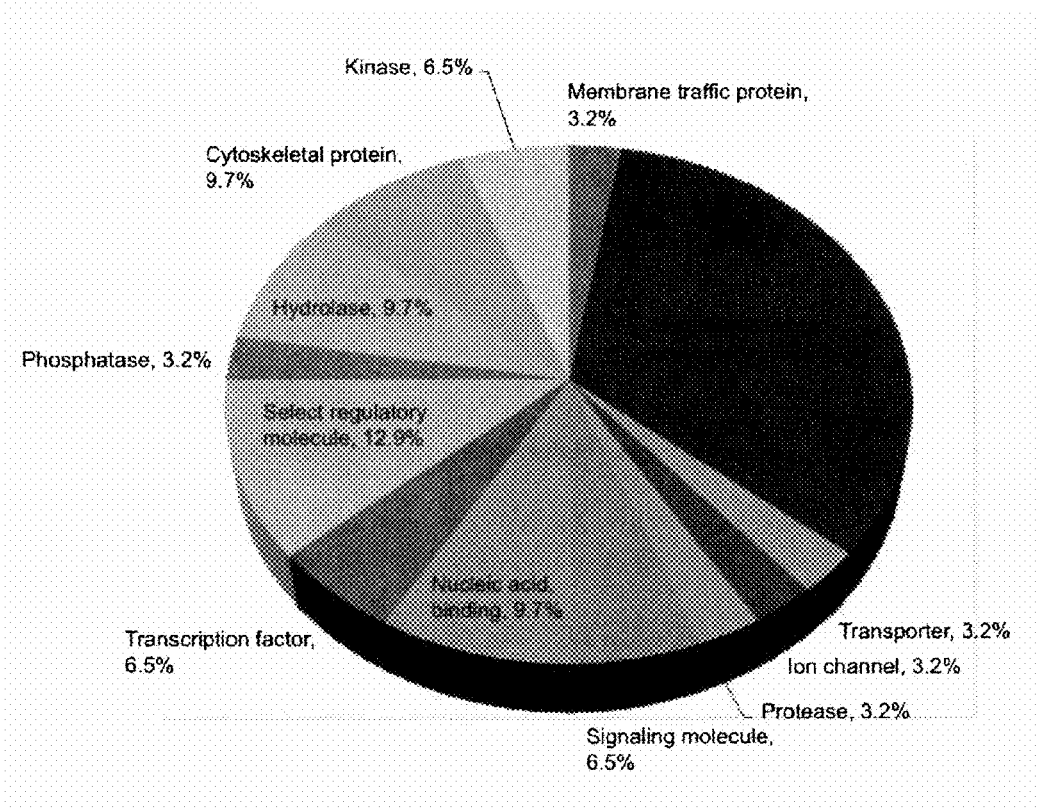
FIG. 5 shows PANTHER molecular functions categorization of the 35 unique genes.
Figure 6:
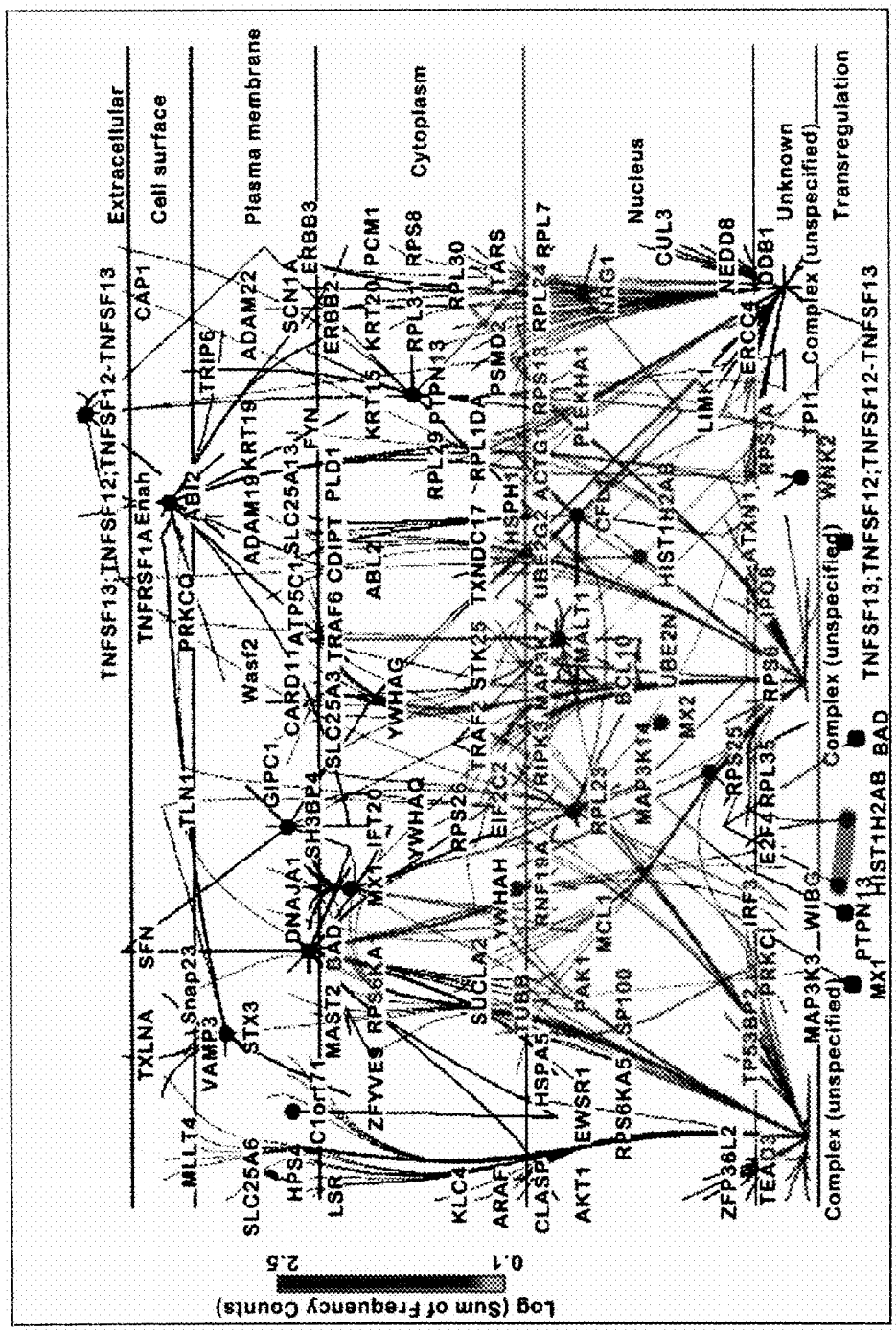
FIG. 6 shows biomolecular interaction network of the identified gene candidates.

In the description that follows, a number of terms are used, the following definitions are provided to facilitate understanding of various aspects of the disclosure. Use of examples in the specification, including examples of terms, is for illustrative purposes only and is not intended to limit the scope and meaning of the embodiments of the invention herein. Numeric ranges are inclusive of the numbers defining the range. In the specification, the word "comprising" is used as an open-ended term, substantially equivalent to the phrase "including, but not limited to," and the word "comprises" has a corresponding meaning.

The present disclosure provides, in part, target host factors. By target host factors is meant a host polypeptide, DNA or RNA that—when inhibited, decreased or otherwise interfered with—reduces virus replication and/or virus-mediated cytotoxicity in a host cell infected with the virus. Modulation of the expression level of host factor, or of host factor product activity, prevents and/or ameliorates disease progression. For example, virus replication and/or virus-mediated cytotoxicity and/or apoptosis may be affected. Thus, compounds that modulate the expression of a target host factor or the activity of a target host factor may be used in the diagnosis, treatment, and/or prevention of a viral infection. In particular, target host factors in the present disclosure include endogenous genes and gene products and their variants, as described herein.

Viral infections may include for example infections by respiratory viruses, including but not limited to, various types of influenza, such as influenza A, influenza B and numerous other strains of influenza, including seasonal, avian (e.g., H5N1 strains), and swine (e.g., H1N1 strains).

The present disclosure provides compositions that inhibit target host factors, for example nucleic acids, such as polynucleotides. More specifically, it provides siRNAs, such as shRNAs, that inhibit target host factors and are therefore useful in treating virus infection and/or reducing virus replication and/or virus-mediated cytotoxicity.

The novel target host factors are, for example, ABI2, ARRDC3, BAD, BRCA1, C17orf85, C1orf71, C6orf162, CCNJL, CFL1, GON4L, HCG 1986447, HIST1H2AB, HPS4, LHX8, RPS25, RPL23, RPL32, LOC730139, LRRC39, MALT1, MX1, MERTK, MX2, NRG1, OR52A1, PLEKHH1, PTPN13, PTPRJ, RLN1, RNF19A, SH3BP4, SLC7A14, ST8SIA3, STX3, TMC6, TMTC4, TNFSF12-TNFSF13, TNFSF13, TTN, UBXN7, USP47, WNK2, YPEL2, ZNF251 and SCG2 (see Table 1). The novel target host factor may be BAD, TNFSF12-TNFSF13, TNFSF13, MX2 or USP47. The target host factors may be used as targets for therapy. The target host factors can also can be used to identify compounds useful in the diagnosis, prevention, and/or therapy of virus infection, for example influenza virus infection.

By "reduce," "reduction", or "reducing" is meant to destroy, prevent, control, decrease, slow, or otherwise interfere with the production, replication, and/or virus-mediated cytotoxicity of a virus by at least about 10% to about 100%, at least about 30% to about 100%, at least about 50% to about 100%, or any value therebetween for example about 10%, 15%, 20%, 25%, 30%, 35%, 40%, 45%, 50%, 55%, 60%, 65%, 70%, 75%, 80%, 85%, 90%, 95%, 99%, or 100% when compared to the production or replication of a virus in the absence of the inhibitor.

"Inhibitors" refers to molecules that inhibit and/or block an identified function. Any molecule or compound having potential to inhibit and/or block an identified function can be a "test molecule" or "test compound", as described herein. For example, referring to anti-viral function or anti-apoptotic activity by acting on the ABI2, ARRDC3, BAD, BRCA1, C17orf85, C1orf71, C6orf162, CCNJL, CFL1, GON4L, HCG 1986447, HIST1H2AB, HPS4, LHX8, RPS25, RPL23, RPL32, LOC730139, LRRC39, MALT1, MX1, MERTK, MX2, NRG1, OR52A1, PLEKHH1, PTPN13, PTPRJ, RLN1, RNF19A, SH3BP4, SLC7A14, ST8SIA3, STX3, TMC6, TMTC4, TNFSF12-TNFSF13, TNFSF13, TTN, UBXN7, USP47, WNK2, YPEL2, ZNF251 or SCG2 polypeptide, DNA or RNA such molecules or compounds may be identified using in vitro and in vivo assays of ABI2, ARRDC3, BAD, BRCA1, C17orf85, C1orf71, C6orf162, CCNJL, CFL1, GON4L, HCG 1986447, HIST1H2AB, HPS4, LHX8, RPS25, RPL23, RPL32, LOC730139 USP47, LRRC39, MALT1, MX1, MERTK, MX2, NRG1, OR52A1, PLEKHH1, PTPN13, PTPRJ, RLN1, RNF19A, SH3BP4, SLC7A14, ST8SIA3, STX3, TMC6, TMTC4, TNFSF12-TNFSF13, TNFSF13, TTN, UBXN7, USP47, WNK2, YPEL2, ZNF251 or SCG2, respectively. Inhibitors are molecules or compounds that partially or totally block ABI2, ARRDC3, BAD, BRCA1, C17orf85, C1orf71, C6orf162, CCNJL, CFL1, GON4L, HCG 1986447, HIST1H2AB, HPS4, LHX8, RPS25, RPL23, RPL32, LOC730139 USP47, LRRC39, MALT1, MX1, MERTK, MX2, NRG1, OR52A 1, PLEKHH1, PTPN13, PTPRJ, RLN1, RNF19A, SH3BP4, SLC7A14, ST8SIA3, STX3, TMC6, TMTC4, TNFSF12-TNFSF13, TNFSF13, TTN, UBXN7, USP47, WNK2, YPEL2, ZNF251 and/or SCG2 activity, decrease, prevent, or delay their activation, or desensitize the cellular response. This may be accomplished by binding to ABI2, ARRDC3, BAD, BRCA1, C17orf85, C1orf71, C6orf162, CCNJL, CFL1, GON4L, HCG 1986447, HIST1H2AB, HPS4, LHX8, RPS25, RPL23, RPL32, LOC730139 USP47, LRRC39, MALT1, MX1, MERTK, MX2, NRG1, OR52A1, PLEKHH1, PTPN13, PTPRJ, RLN1, RNF19A, SH3BP4, SLC7A14, ST8SIA3, STX3, TMC6, TMTC4, TNFSF12-TNFSF13, TNFSF13, TTN, UBXN7, USP47, WNK2, YPEL2, ZNF251 and/or SCG2 factors directly or via other intermediate molecules. An antagonist or an antibody that blocks ABI2, ARRDC3, BAD, BRCA1, C17orf85, C1orf71, C6orf162, CCNJL, CFL1, GON4L, HCG 1986447, HIST1H2AB, HPS4, LHX8, RPS25, RPL23, RPL32, LOC730139, LRRC39, MALT1, MX1, MERTK, MX2, NRG1, OR52A1, PLEKHH1, PTPN13, PTPRJ, RLN1, RNF19A, SH3BP4, SLC7A14, ST8SIA3, STX3, TMC6, TMTC4, TNFSF12-TNFSF13, TNFSF13, TTN, UBXN7, USP47, WNK2, YPEL2, ZNF251 and/or SCG2 activity, including inhibition of pro-viral function or pro-apoptotic activity of ABI2, ARRDC3, BAD, BRCA1, C17orf85, C1orf71, C6orf162, CCNJL, CFL1, GON4L, HCG 1986447, HIST1H2AB, HPS4, LHX8, RPS25, RPL23, RPL32, LOC730139 USP47, LRRC39, MALT1, MX1, MERTK, MX2, NRG1, OR52A1, PLEKHH1, PTPN13, PTPRJ, RLN1, RNF19A, SH3BP4, SLC7A14, ST8SIA3, STX3, TMC6, TMTC4, TNFSF12-TNFSF13, TNFSF13, TTN, UBXN7, USP47, WNK2, YPEL2, ZNF251 and/or SCG2, is considered to be such an inhibitor.

TABLE 1

Target host factors

| Target host factor (Gene Name) | Gene ID | Examples of RefSeq Numbers (mRNA) | Examples of inhibitors of target host factor |
|---|---|---|---|
| ABI2 | 10152 | NM_005759 | SEQ ID NO 51 |
| ARRDC3 | 57561 | NM_020801 | SEQ ID NO 52 |
| BAD | 572 | NM_004322 NM_032989 | SEQ ID NOs 1 to 9 |
| BRCA1 | 672 | NM_007294 NM_007297 NM_007298 NM_007299 NM_007300 | SEQ ID NOs 53 to 55 |

TABLE 1-continued

Target host factors

| Target host factor (Gene Name) | Gene ID | Examples of RefSeq Numbers (mRNA) | Examples of inhibitors of target host factor |
|---|---|---|---|
| C17orf85 | 55421 | NM_001114118 NM_018553 | SEQ ID NO 56 |
| C1orf71 (CNST) | 163882 | NM_001139459 NM_152609 | SEQ ID NO 57 |
| C6orf162 | 57150 | NM_001042493 NM_020425 | SEQ ID NO 58 |
| CCNJL | 79616 | NM_024565 | SEQ ID NO 59 |
| CFL1 | 1072 | NM_005507 | SEQ ID NO 50 |
| GON4L | 54856 | NM_001037533 NM_032292 | SEQ ID NO 60 |
| HCG 1986447 | 729324 | XR_041499.2 | SEQ ID NO 47 |
| HIST1H2AB | 8335 | NM_003513 | SEQ ID NO 61 |
| HPS4 | 89781 | NM_022081 NM_152841 | SEQ ID NO 62 |
| LHX8 | 431707 | NM_001001933 | SEQ ID NO 63 |
| RPS25 | 6230 | NM_001028 | SEQ ID NO 44 |
| RPL23 | 9349 | NM_000978 | SEQ ID NO 64 |
| RPL32 | 6161 | NM_000994 NM_001007073 | SEQ ID NO 65 |
| LOC730139 | 730139 | XM_001134281.1 | SEQ ID NO 67 to 68 |
| LRRC39 | 127495 | NM_144620 | SEQ ID NO 69 to 70 |
| MALT1 | 10892 | NM_006785 NM_173844 | SEQ ID NO 43 |
| MX1 | 4599 | NM_002462 NM_001144925 | SEQ ID NO 41 to 42 |
| MERTK | 10461 | NM_006343 | SEQ ID NO 93 to 95 |
| MX2 | 4600 | NM_002463 | SEQ ID NOs 25-29 |
| NRG1 | 3084 | NM_001159995 NM_001159996 NM_001159999 NM_001160001 NM_001160002 NM_001160004 NM_001160005 NM_001160007 NM_001160008 NM_004495 NM_013956 NM_013957 NM_013958 NM_013959 NM_013960 NM_013962 NM_013964 | SEQ ID NO 71 |
| OR52A1 | 23538 | NM_012375 | SEQ ID NO 72 to 73 |
| PLEKHH1 | 57475 | NM_020715 | SEQ ID NO 74 |
| PTPN13 | 5783 | NM_006264 NM_080683 NM_080684 NM_080685 | SEQ ID NO 75 |
| PTPRJ | 5795 | NM_001098503 NM_002843 | SEQ ID NO 76 to 77 |
| RLN1 | 6013 | NM_006911 | SEQ ID NO 78 |
| RNF19A | 25897 | NM_015435 NM_183419 | SEQ ID NO 79 |
| SH3BP4 | 23677 | NM_014521 | SEQ ID NO 45 |
| SLC7A14 | 57709 | NM_020949 | SEQ ID NO 80 |
| ST8SIA3 | 51046 | NM_015879 | SEQ ID NO 81 to 82 |
| STX3 | 6809 | NM_004177 | SEQ ID NO 83 |
| TMC6 | 11322 | NM_001127198 NM_007267 | SEQ ID NO 49 |
| TMTC4 | 84899 | NM_001079669 NM_032813 | SEQ ID NO 84 to 85 |
| TNFSF12-TNFSF13, | 407977 | NM_172089 | SEQ ID NOs 11 to 19 |
| TNFSF13 | 8741 | NM_003808 NM_172087 NM_172088 | SEQ ID NOs 11 to 23 |
| TTN | 7273 | NM_003319 NM_133378 NM_133379 NM_133432 NM_133437 | SEQ ID NO 86 to 87 |
| UBXN7 | 26043 | NM_015562 | SEQ ID NO 88 |
| USP47 | 55031 | NM_017944.3 | SEQ ID NOs 31 to 40 |
| WNK2 | 65268 | NM_006648 | SEQ ID NO 48 |
| YPEL2 | 388403 | NM_001005404 | SEQ ID NO 89 to 90 |
| ZNF251 | 90987 | NM_138367 | SEQ ID NO 91 to 92 |
| SCG2 | 7857 | NM_003469 | SEQ ID NO 96 to 98 |

Inhibitors may be for example siRNA, RNAi, shRNA, antisense RNA, antisense DNA, decoy molecules, decoy DNA, double stranded DNA, single-stranded DNA, complexed DNA, encapsulated DNA, viral DNA, plasmid DNA, naked RNA, encapsulated RNA, viral RNA, double stranded RNA, molecules capable of generating RNA interference, or combinations thereof. The group of inhibitors also includes genetically modified versions of ABI2, ARRDC3, BAD, BRCA1, C17orf85, C1orf71, C6orf162, CCNJL, CFL1, GON4L, HCG 1986447, HIST1H2AB, HPS4, LHX8, RPS25, RPL23, RPL32, LOC730139, LRRC39, MALT1, MX1, MERTK, MX2, NRG1, OR52A1, PLEKHH1, PTPN13, PTPRJ, RLN1, RNF19A, SH3BP4, SLC7A14, ST8SIA3, STX3, TMC6, TMTC4, TNFSF12-TNFSF13, TNFSF13, TTN, UBXN7, USP47, WNK2, YPEL2, ZNF251 and SCG2, for example, versions with altered activity. The group thus is inclusive of the naturally occurring protein with altered activity, as well as synthetic ligands, peptide ligands, antagonists, agonists, antibodies, small chemical molecules and the like.

Screening for Inhibitors of Target Host Factors

A "test substance" or "test compound" is a compound or mixture of compounds, whose ability to modulate ABI2, ARRDC3, BAD, BRCA1, C17orf85, C1orf71, C6orf162, CCNJL, CFL1, GON4L, HCG 1986447, HIST1H2AB, HPS4, LHX8, RPS25, RPL23, RPL32, LOC730139, LRRC39, MALT1, MX1, MERTK, MX2, NRG1, OR52A1, PLEKHH1, PTPN13, PTPRJ, RLN1, RNF19A, SH3BP4, SLC7A14, ST8SIA3, STX3, TMC6, TMTC4, TNFSF12-TNFSF13, TNFSF13, TTN, UBXN7, USP47, WNK2, YPEL2, ZNF251 and/or SCG2 activity may be defined by various assays. A "test substance" is also referred to as a "candidate drug" or "candidate compound" in the present description.

Test substances may be screened from large libraries of synthetic or natural compounds. Numerous means are currently used for random and directed synthesis of saccharide, peptide, and nucleic acid based compounds. Synthetic compound libraries are commercially available from Maybridge Chemical Co. (Trevillet, Cornwall, UK), Comgenex (Princeton, N.J.), Brandon Associates (Merrimack, N.H.), and Microsource (New Milford, Conn.). A rare chemical library is available from Aldrich (Milwaukee, Wis.). Alternatively, libraries of natural compounds in the form of bacterial, fungal, plant and animal extracts are available from, e.g., Pan Laboratories (Bothell, Wash.) or MycoSearch (NC), or are readily producible. Additionally, natural and synthetically produced libraries and compounds are readily modified through conventional chemical, physical, and biochemical means (Blondelle et al., TIBTech, 1996; 14:60).

A modulatory effect may be determined by an in vitro method using a recombinant ABI2, ARRDC3, BAD, BRCA1, C17orf85, C1orf71, C6orf162, CCNJL, CFL1, GON4L, HCG 1986447, HIST1H2AB, HPS4, LHX8, RPS25, RPL23, RPL32, LOC730139, LRRC39, MALT1, MX1, MERTK, MX2, NRG1, OR52A1, PLEKHH1, PTPN13, PTPRJ, RLN1, RNF19A, SH3BP4, SLC7A14, ST8SIA3, STX3, TMC6, TMTC4, TNFSF12-TNFSF13, TNFSF13, TTN, UBXN7, USP47, WNK2, YPEL2, ZNF251 or SCG2 reporter gene promoter activity system. Reporter genes encode detectable proteins, including, but not limited to, chloramphenicol transferase (CAT), beta-galactosidase (beta-gal), luciferase, green fluorescent protein (GFP) and derivatives thereof, yellow fluorescent protein and derivatives thereof, alkaline phosphatase, other enzymes that can be adapted to produce a detectable product, and other gene products that can be detected, e.g., immunologically (by immunoassay).

A screen involves detecting a change in the expression of the reporter gene by the host cell when contacted with a test substance. If there is no change in expression of the reporter gene, the test to substance may not be an effective modulator. If reporter gene expression is modified, in particular reduced or eliminated, the test substance has modulated, e.g., inhibited, ABI2, ARRDC3, BAD, BRCA1, C17orf85, C1orf71, C6orf162, CCNJL, CFL1, GON4L, HCG 1986447, HIST1H2AB, HPS4, LHX8, RPS25, RPL23, RPL32, LOC730139, LRRC39, MALT1, MX1, MERTK, MX2, NRG1, OR52A1, PLEKHH1, PTPN13, PTPRJ, RLN1, RNF19A, SH3BP4, SLC7A14, ST8SIA3, STX3, TMC6, TMTC4, TNFSF12-TNFSF13, TNFSF13, TTN, UBXN7, USP47, WNK2, YPEL2, ZNF251 or SCG2-mediated gene expression, and is thus a candidate for development as a ABI2, ARRDC3, BAD, BRCA1, C17orf85, C1orf71, C6orf162, CCNJL, CFL1, GON4L, HCG 1986447, HIST1H2AB, HPS4, LHX8, RPS25, RPL23, RPL32, LOC730139, LRRC39, MALT1, MX1, MERTK, MX2, NRG1, OR52A1, PLEKHH1, PTPN13, PTPRJ, RLN1, RNF19A, SH3BP4, SLC7A14, ST8SIA3, STX3, TMC6, TMTC4, TNFSF12-TNFSF13, TNFSF13, TTN, UBXN7, USP47, WNK2, YPEL2, ZNF251 or SCG2 modulator, for use as inhibitor of virus replication and virus-mediated cytotoxicity. The reporter gene assay system described herein may be used in a high-throughput primary screen for antagonists, or it may be used as a secondary functional screen for candidate compounds identified by a different primary screen, e.g., a binding assay screen that identifies compounds that modulate ABI2, ARRDC3, BAD, BRCA1, C17orf85, C1orf71, C6orf162, CCNJL, CFL1, GON4L, HCG 1986447, HIST1H2AB, HPS4, LHX8, RPS25, RPL23, RPL32, LOC730139, LRRC39, MALT1, MX1, MERTK, MX2, NRG1, OR52A1, PLEKHH1, PTPN13, PTPRJ, RLN1, RNF19A, SH3BP4, SLC7A14, ST8SIA3, STX3, TMC6, TMTC4, TNFSF12-TNFSF13, TNFSF13, TTN, UBXN7, USP47, WNK2, YPEL2, ZNF251 or SCG2 transcription activity.

Potential drugs may be identified by screening in high-throughput assays, including without limitation cell-based or cell-free assays. It will be appreciated by those skilled in the art that different types of assays can be used to detect different types of agents. Several methods of automated assays have been developed in recent years so as to permit screening of tens of thousands of compounds in a short period of time. Such high-throughput screening methods are particularly useful when screening for candidates for further testing.

Examples of target host factor modulators include the polynucleotides such as siRNAs. "siRNA" refers to small interfering RNAs, which includes short hairpin RNA ("shRNA") (Paddison et al., Genes & Dev. 16: 948-958, 2002), that are capable of causing interference (as described herein for RNAi) and can cause post-transcriptional silencing of specific genes in cells, for example, mammalian cells (including human cells) and in the body, for example, mammalian bodies (including humans). The phenomenon of RNA interference (RNAi) is described and discussed in Bass, Nature, 411:428-29, 2001; Elbashir et al., Nature, 411:494-98, 2001; and Fire et al., Nature, 391:806-11, 1998, wherein methods of making interfering RNA also are discussed. Exemplary siRNAs could have up to 29 bps, 25 bps, 22 bps, 21 bps, 20 bps, 15 bps, 10 bps, 5 bps or any integer thereabout or therebetween.

Expression of selected genes can be suppressed in human cells by transfecting with exogenous, short RNA duplexes (siRNA) where one strand corresponds to a target region of the mRNA of interest (Elbashir et al., Nature, 2001; 411:494-498). Upon entry into the cell, siRNA causes the degradation of single-stranded (ssRNAs) RNAs of with identical or near identical sequences, including endogenous mRNAs. siRNA is more potent than standard anti-sense technology since it acts through a catalytic mechanism. Effective strategies to deliver siRNAs to target cells, for example, include physical or chemical transfection. An alternative strategy uses the endogenous expression of siRNAs by various Pol III promoter expression cassettes that allow transcription of functional siRNAs or their precursors (Scherr et al., Curr. Med. Chem., 2003; 10(3):245-56). Recently, the RNA-polymerase III dependent promoter (H1-RNA promoter) was inserted in the lentiviral genome to drive the expression of a small hairpin RNA (shRNA) against enhanced green fluorescent protein (Abbas-Turki et al., Hum. Gene Ther., 2002; 13(18): 2197-201). siRNA can also be delivered in a viral vector derived, e.g., from a lentivirus (Tiscornia et al., Proc. Natl. Acad. Sci. U.S.A., 2003; 100:1844-8).

Target Host Factors and siRNAs

BAD

According to an aspect of the present disclosure, it has been determined that BAD may be a suitable target when looking at inhibition of virus replication or virus-mediated cytotoxicity for example influenza virus.

The present disclosure provides polynucleotides that inhibit expression of a polypeptide encoded by a BAD coding region. As used herein a BAD coding region refers to the genomic nucleotide sequence disclosed under GeneID: 572. Examples of target mRNA encoding a BAD polypeptide are the sequences available at Genbank accession numbers NM_004322 (SEQ ID NO:10) or NM_032989 (SEQ ID NO: 103).

Polynucleotides of the present disclosure that will act to inhibit expression of a BAD polypeptide, include polynucleotides with a sense strand that is substantially identical or identical to a region of SEQ ID NO:10 or SEQ ID NO:103. Examples of such polynucleotides that will act to inhibit expression of a polypeptide encoded by a BAD coding region include SEQ ID NO:1, SEQ ID NO:2, SEQ ID NO:3, SEQ ID NO:4. SEQ ID NO:5, SEQ ID NO:6, SEQ ID NO:7, SEQ ID NO:8, and SEQ ID NO:9.

TABLE 2

Inhibitors of BAD

| BAD | shRNA species | SEQ ID NO | SEQUENCE |
|---|---|---|---|
| | V2HS_15289 | 1 | CTCACTACCAAATGTTAAT |
| | V2HS_243025 | 2 | CAGTGACCTTCGCTCCACA |
| | V2HS_201511 | 3 | GAGTTTGTGGACTCCTTTA |
| | V2HS_202976 | 4 | GTGCTCACTACCAAATGTT |

TABLE 2-continued Inhibitors of BAD

| V2HS_262043 | 5 | GACTTGGACTTGGATGTAA |
|---|---|---|
| siRNA species | SEQ ID NO | SEQUENCE |
| J-003870-09 | 6 | GAUCGGAACUUGGGCAGGG |
| J-003870-10 | 7 | CAGAGUUUGAGCCGAGUGA |
| J-003870-11 | 8 | GAGCUCCGGAGGAUGAGUG |
| J-003870-12 | 9 | UUGUGGACUCCUUUAAGAA |

TNFSF12-13 (TWE-PRIL)

The present disclosure provides polynucleotides that inhibit expression of a fusion polypeptide encoded by a TNFSF12-13 coding region. As used herein a TNFSF12-13 coding region refers to the genomic nucleotide sequence disclosed under GeneID: 407977. An example of a target mRNA encoding a TNFSF12-13 fusion polypeptide is the sequence available at Genbank accession number NM__172089 (SEQ ID NO: 99).

Polynucleotides of the present disclosure that will act to inhibit expression of a TNFSF12-13 fusion polypeptide, include polynucleotides with a sense strand that is substantially identical or identical to a region of SEQ ID NO: 99. Examples of such polynucleotides that will act to inhibit expression of a polypeptide encoded by a TNFSF12-13 coding region include SEQ ID NO: 11, SEQ ID NO: 12. SEQ ID to NO: 13, SEQ ID NO: 14, SEQ ID NO: 15, SEQ ID NO: 16, SEQ ID NO: 17, SEQ ID NO: 18 and SEQ ID NO: 19.

TABLE 3

Inhibitors of TNFSF12-TNFSF13

| TNFSF12-TNFSF13 (TWE-PRIL) | shRNA species | SEQ ID NO | SEQUENCE |
|---|---|---|---|
| | V2HS_17313 | 11 | GCCGCCCTCTGCTAGGGAA |
| | V2HS_17314 | 12 | GATATTCTGAGTGTCATAA |
| | V2HS_17316 | 13 | GGTGCCTTCGCAGTCAAAT |
| | V2HS_17317 | 14 | GAGACTCTATTCCGATGTA |
| | V2HS_17318 | 15 | CTCCAGAGATGTAGCTATT |
| | siRNA species | SEQ ID NO | SEQUENCE |
| | J-032530-05 | 16 | GGGCAAGGGCGAAACUUAA |
| | J-032530-06 | 17 | GCAGGUGUCUUCCAUUUAC |
| | J-032530-07 | 18 | UGACAGAGGUGAUGUGGCA |
| | J-032530-08 | 19 | GGAGUUUAUCUGCUGUAUA |

TNFSF13 (APRIL)

In another aspect, the present disclosure includes polynucleotides that inhibit expression of a polypeptide encoded by a TNFSF13 coding region. As used herein a TNFSF13 coding region refers to the genomic nucleotide sequence disclosed for example under GeneID: 8741. Several splice variants of the TNFSF13 coding region are expressed and encode polypeptides including a TNFSF13 alpha polypeptide, a TNFSF13 beta polypeptide, and a TNFSF13 gamma polypeptide.

An example of a target mRNA encoding a TNFSF13 alpha polypeptide is the sequence available at Genbank accession number NM__003808 (SEQ ID NO: 100). An example of a target mRNA encoding a TNFSF13 beta polypeptide is the sequence available at Genbank accession number NM__172087 (SEQ ID NO:101). An example of a target mRNA encoding a TNFSF13 gamma polypeptide is the sequence available at Genbank accession number NM__172088 (SEQ ID NO: 102).

A preferred target mRNA includes a sequence that is present in all three splice variants. Polynucleotides of the present disclosure that will act to inhibit expression of a TNFSF13 alpha polypeptide, a TNFSF13 beta polypeptide, and a TNFSF13 gamma polypeptide include polynucleotides with a sense strand that is substantially identical or identical to a region of SEQ ID NO: 100.

Examples of such polynucleotides that will act to inhibit expression of a polypeptide encoded by a TNFSF13 coding region include SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22 and SEQ ID NO: 23.

TABLE 4

Inhibitors of TNFSF13 (APRIL)

| TNFSF13 (APRIL) | shRNA species | SEQ ID NO | SEQUENCE |
|---|---|---|---|
| | V2HS_17313 | 11 | GCCGCCCTCTGCTAGGGAA |
| | V2HS_17314 | 12 | GATATTCTGAGTGTCATAA |
| | V2HS_17316 | 13 | GGTGCCTTCGCAGTCAAAT |
| | V2HS_17317 | 14 | GAGACTCTATTCCGATGTA |
| | V2HS_17318 | 15 | CTCCAGAGATGTAGCTATT |
| | siRNA species | SEQ ID NO | SEQUENCE |
| | J-032530-05 | 16 | GGGCAAGGGCGAAACUUAA |
| | J-032530-06 | 17 | GCAGGUGUCUUCCAUUUAC |
| | J-032530-07 | 18 | UGACAGAGGUGAUGUGGCA |
| | J-032530-08 | 19 | GGAGUUUAUCUGCUGUAUA |
| | J-011523-05 | 20 | GGGCAAGGGCGAAACUUAA |
| | J-011523-06 | 21 | GCAGGUGUCUUCCAUUUAC |
| | J-011523-07 | 22 | UGACAGAGGUGAUGUGGCA |
| | J-011523-08 | 23 | GGAGUUUAUCUGCUGUAUA |

MX2

In another aspect, the present disclosure includes polynucleotides that inhibit expression of a polypeptide encoded by a MX2 coding region. As used herein a MX2 coding region refers to the genomic nucleotide sequence disclosed under GeneID: 4600. An example of a target mRNA encoding a MX2 polypeptide is the sequence available at Genbank accession number NM__002463 (SEQ ID NO: 24).

Polynucleotides of the present disclosure that will act to inhibit expression of a MX2 polypeptide, include polynucleotides with a sense strand that is substantially identical or identical to a region of SEQ ID NO: 24. Examples of such polynucleotides that will act to inhibit expression of a polypeptide encoded by a MX2 coding region include SEQ ID NO: 25, SEQ ID NO: 26, SEQ ID NO: 27. SEQ ID NO: 28 and SEQ ID NO: 29.

TABLE 5

Inhibitors of MX2

| MX2 shRNA species | SEQ ID NO | SEQUENCE |
|---|---|---|
| V2HS_152031 | 25 | GACAAGATGTTCTTTCTAA |
| siRNA species | SEQ ID NO | SEQUENCE |
| J-011736-05 | 26 | GAGCACGAUUGAAGACAUA |
| J-011736-06 | 27 | GGAGAAUGAGACCCGUUUA |
| J-011736-07 | 28 | GAAUUUACCGGCUCACUCA |
| J-011736-08 | 29 | GGGACGCCUUCACAGAAUA |

USP47

The present disclosure includes polynucleotides that inhibit expression of a polypeptide encoded by a USP47 coding region. As used herein a USP47 coding region refers to the genomic nucleotide sequence disclosed under GeneID: 55031. An example of a target mRNA encoding a USP47 polypeptide is the sequence available at Genbank accession number NM_017944.3 (SEQ ID NO: 30).

Polynucleotides of the present disclosure that will act to inhibit expression of a USP47 polypeptide, include polynucleotides with a sense strand that is substantially identical or identical to a region of SEQ ID NO:30. Examples of such polynucleotides that will act to inhibit expression of a polypeptide encoded by a USP47 coding region include SEQ ID NO: 31, SEQ ID NO: 32, SEQ ID NO: 33. SEQ ID NO: 34, SEQ ID NO: 35, SEQ ID NO: 36, SEQ ID NO: 37, SEQ ID NO: 38, SEQ ID NO: 39 and SEQ ID NO: 40.

TABLE 6

Inhibitor of USP 47

| USP47 shRNA species | SEQ ID NO | SEQUENCE |
|---|---|---|
| V2HS_174637 | 31 | GAATCTGTCTTGAAACCAA |
| V2HS_174639 | 32 | CGCAATACATGCAAGATAA |
| V2HS_174641 | 33 | GGATTCCTTTGGATGATAT |
| V2HS_174642 | 34 | GATTTAGACTGGAATCCTA |
| V2HS_218228 | 35 | CAATGACTTGCTATTTGAA |
| V2HS_174640 | 40 | CTTATAAGATGATGGATTT |
| shRNA species | SEQ ID NO | SEQUENCE |
| J-006093-05 | 36 | GCAACGAUUUCUCCAAUGA |
| J-006093-06 | 37 | CAACAUGUCAGCAGGAUAA |
| J-006093-07 | 38 | GCUGUCGCCUUGUUAAAUA |
| J-006093-08 | 39 | CGCAAUACAUGCAAGAUAA |

MX1

In another aspect, the present disclosure includes polynucleotides that inhibit expression of a polypeptide encoded by a MX1 coding region. As used herein a MX1 coding region refers to the genomic nucleotide sequence disclosed under GeneID: 4599. An example of a target mRNA encoding a MX1 polypeptide is the sequence available at Genbank accession numbers NM_002462 and NM_001144925.

Polynucleotides of the present disclosure that will act to inhibit expression of a MX1 polypeptide, include polynucleotides with a sense strand that is substantially identical or identical to a region of NM_002462 or NM_001144925. Examples of such polynucleotides that will act to inhibit expression of a polypeptide encoded by a MX1 coding region include SEQ ID NO: 41, SEQ ID NO: 42.

MALT1

In another aspect, the present disclosure includes polynucleotides that inhibit expression of a polypeptide encoded by a MALT1 coding region. As used herein a MALT1 coding region refers to the genomic nucleotide sequence disclosed under GeneID: 10892. An example of a target mRNA encoding a MALT1 polypeptide is the sequence available at Genbank accession numbers NM_006785 or NM_173844.

Polynucleotides of the present disclosure that will act to inhibit expression of a MALT1 polypeptide, include polynucleotides with a sense strand that is substantially identical or identical to a region of NM_006785 or NM_173844. Examples of such polynucleotides that will act to inhibit expression of a polypeptide encoded by a MALT1 coding region include SEQ ID NO: 43.

RPS25

In another aspect, the present disclosure includes polynucleotides that inhibit expression of a polypeptide encoded by a RPS25 coding region. As used herein a RPS25 coding region refers to the genomic nucleotide sequence disclosed under GeneID: 6230. An example of a target mRNA encoding a RPS25 polypeptide is the sequence available at Genbank accession number NM_001028.

Polynucleotides of the present disclosure that will act to inhibit expression of a RPS25 polypeptide, include polynucleotides with a sense strand that is substantially identical or identical to a region of NM_001028. Examples of such polynucleotides that will act to inhibit expression of a polypeptide encoded by a RPS25 coding region include SEQ ID NO: 44.

SH3BP4

In another aspect, the present disclosure includes polynucleotides that inhibit expression of a polypeptide encoded by a SH3BP4 coding region. As used herein a SH3BP4 coding region refers to the genomic nucleotide sequence disclosed under GeneID: 23677. An example of a target mRNA encoding a SH3BP4 polypeptide is the sequence available at Genbank accession number NM_014521.

Polynucleotides of the present disclosure that will act to inhibit expression of a SH3BP4 polypeptide, include polynucleotides with a sense strand that is substantially identical or identical to a region of NM_014521. Examples of such polynucleotides that will act to inhibit expression of a polypeptide encoded by a SH3BP4 coding region include SEQ ID NO: 45.

HCG 1986447

In another aspect, the present disclosure includes polynucleotides that inhibit expression of a polypeptide encoded by a HCG 1986447 coding region. As used herein a HCG 1986447 coding region refers to the genomic nucleotide sequence disclosed under GeneID: 729324. An example of a target mRNA encoding a HCG 1986447 polypeptide is the sequence available at SEQ ID NO: 46.

Polynucleotides of the present disclosure that will act to inhibit expression of a HCG 1986447 polypeptide, include polynucleotides with a sense strand that is substantially identical or identical to a region of SEQ ID NO: 46. Examples of such polynucleotides that will act to inhibit expression of a polypeptide encoded by a HCG 1986447 coding region include SEQ ID NO: 47.

WNK2

In another aspect, the present disclosure includes polynucleotides that inhibit expression of a polypeptide encoded by a WNK2 coding region. As used herein a WNK2 coding region refers to the genomic nucleotide sequence disclosed under GeneID: 65268. An example of a target mRNA encoding a WNK2 polypeptide is the sequence available at Genbank accession number NM_006648.

Polynucleotides of the present disclosure that will act to inhibit expression of a WNK2 polypeptide, include polynucleotides with a sense strand that is substantially identical or identical to a region of to NM_006648. Examples of such polynucleotides that will act to inhibit expression of a polypeptide encoded by a WNK2 coding region include SEQ ID NO: 48.

TMC6

In another aspect, the present disclosure includes polynucleotides that inhibit expression of a polypeptide encoded by a TMC6 coding region. As used herein a TMC6 coding region refers to the genomic nucleotide sequence disclosed under GeneID: 11322. An example of a target mRNA encoding a TMC6 polypeptide are the sequences available at Genbank accession numbers NM_001127198 and NM_007267.

Polynucleotides of the present disclosure that will act to inhibit expression of a TMC6 polypeptide, include polynucleotides with a sense strand that is substantially identical or identical to a region of NM_001127198 or NM_007267. Examples of such polynucleotides that will act to inhibit expression of a polypeptide encoded by a TMC6 coding region include SEQ ID NO: 49.

CFL1

In another aspect, the present disclosure includes polynucleotides that inhibit expression of a polypeptide encoded by a CFL1 coding region. As used herein a CFL1 coding region refers to the genomic nucleotide sequence disclosed under GeneID: 1072. An example of a target mRNA encoding a CFL1 polypeptide is the sequence available at Genbank accession number NM_005507.

Polynucleotides of the present disclosure that will act to inhibit expression of a CFL1 polypeptide, include polynucleotides with a sense strand that is substantially identical or identical to a region of NM_005507. Examples of such polynucleotides that will act to inhibit expression of a polypeptide encoded by a CFL1 coding region include SEQ ID NO: 50.

ABI2

In another aspect, the present disclosure includes polynucleotides that inhibit expression of a polypeptide encoded by a ABI2 coding region. As used herein a ABI2 coding region refers to the genomic nucleotide sequence disclosed under GeneID: 10152. An example of a target mRNA encoding a ABI2 polypeptide is the sequence available at Genbank accession number NM_005759.

Polynucleotides of the present disclosure that will act to inhibit expression of a ABI2 polypeptide, include polynucleotides with a sense strand that is substantially identical or identical to a region of NM_005759. Examples of such polynucleotides that will act to inhibit expression of a polypeptide encoded by a ABI2 coding region include SEQ ID NO: 51.

ARRDC3

In another aspect, the present disclosure includes polynucleotides that inhibit expression of a polypeptide encoded by a ARRDC3 coding region. As used herein a ARRDC3 coding region refers to the genomic nucleotide sequence disclosed under GeneID: 57561. An example of a target mRNA encoding a ARRDC3 polypeptide is the sequence available at Genbank accession number NM_020801.

Polynucleotides of the present disclosure that will act to inhibit expression of a ARRDC3 polypeptide, include polynucleotides with a sense strand that is substantially identical or identical to a region of NM_020801. Examples of such polynucleotides that will act to inhibit expression of a polypeptide encoded by a ARRDC3 coding region include SEQ ID NO: 52.

BRCA1

In another aspect, the present disclosure includes polynucleotides that inhibit expression of a polypeptide encoded by a BRCA1 coding region. As used herein a BRCA1 coding region refers to the genomic nucleotide sequence disclosed under GeneID: 672. An example of a target mRNA encoding a BRCA1 polypeptide are the sequence available at Genbank accession numbers NM_007294, NM_007297, NM_007298, NM_007299 and NM_007300.

Polynucleotides of the present disclosure that will act to inhibit expression of a BRCA1 polypeptide, include polynucleotides with a sense strand that is substantially identical or identical to a region of NM_007294, NM_007297, NM_007298, NM_007299 or NM_007300. Examples of such polynucleotides that will act to inhibit expression of a polypeptide encoded by a BRCA1 coding region include SEQ ID NO: 53, SEQ ID NO: 54 and SEQ ID NO: 55.

C17orf85

In another aspect, the present disclosure includes polynucleotides that inhibit expression of a polypeptide encoded by a C17orf85 coding region. As used herein a C17orf85 coding region refers to the genomic nucleotide sequence disclosed under GeneID: 55421. An example of a target mRNA encoding a C17orf85 polypeptide are the sequences available at Genbank accession numbers NM_001114118 and NM_018553.

Polynucleotides of the present disclosure that will act to inhibit expression of a C17orf85 polypeptide, include polynucleotides with a sense strand that is substantially identical or identical to a region of NM_001114118 or NM_018553. Examples of such polynucleotides that will act to inhibit expression of a polypeptide encoded by a C17orf85 coding region include SEQ ID NO: 56.

C1orf71 (CNST)

In another aspect, the present disclosure includes polynucleotides that inhibit expression of a polypeptide encoded by a C1orf71 coding region. As used herein a C1orf71 coding region refers to the genomic nucleotide sequence disclosed under GeneID: 163882. An example of a target mRNA encoding a C1orf71 polypeptide are the sequences available at Genbank accession numbers NM_001139459 and NM_152609.

Polynucleotides of the present disclosure that will act to inhibit expression of a C1orf71 polypeptide, include polynucleotides with a sense strand that is substantially identical or identical to a region of NM_001139459 or NM_152609. Examples of such polynucleotides that will act to inhibit expression of a polypeptide encoded by a C1orf71 coding region include SEQ ID NO: 57.

C6orf162

In another aspect, the present disclosure includes polynucleotides that inhibit expression of a polypeptide encoded by a C6orf162 coding region. As used herein a C6orf162 coding region refers to the genomic nucleotide sequence disclosed under GeneID: 57150. An example of a target mRNA encoding a C6orf162 polypeptide are the sequences available at Genbank accession numbers NM_001042493 and NM_020425.

Polynucleotides of the present disclosure that will act to inhibit expression of a C6orf162 polypeptide, include polynucleotides with a sense strand that is substantially identical or identical to a region of NM_001042493 or NM_020425. Examples of such polynucleotides that will act to inhibit expression of a polypeptide encoded by a C6orf162 coding region include SEQ ID NO: 58.

CCNJL

In another aspect, the present disclosure includes polynucleotides that inhibit expression of a polypeptide encoded by a CCNJL coding region. As used herein a CCNJL coding region refers to the genomic nucleotide sequence disclosed under GeneID: 79616. An example of a target mRNA encoding a CCNJL polypeptide is the sequence available at Genbank accession number NM_024565.

Polynucleotides of the present disclosure that will act to inhibit expression of a CCNJL polypeptide, include polynucleotides with a sense strand that is substantially identical or identical to a region of NM_024565. Examples of such polynucleotides that will act to inhibit expression of a polypeptide encoded by a CCNJL coding region include SEQ ID NO: 59.

GON4L

In another aspect, the present disclosure includes polynucleotides that inhibit expression of a polypeptide encoded by a GON4L coding region. As used herein a GON4L coding region refers to the genomic nucleotide sequence disclosed under GeneID: 54856. An example of a target mRNA encoding a GON4L polypeptide are the sequences available at Genbank accession numbers NM_001037533 and NM_032292.

Polynucleotides of the present disclosure that will act to inhibit expression of a GON4L polypeptide, include polynucleotides with a sense strand that is substantially identical or identical to a region of NM_001037533 or NM_032292. Examples of such polynucleotides that will act to inhibit expression of a polypeptide encoded by a GON4L coding region include SEQ ID NO: 60.

HIST1H2AB

In another aspect, the present disclosure includes polynucleotides that inhibit expression of a polypeptide encoded by a HIST1H2AB coding region. As used herein a HIST1H2AB coding region refers to the genomic nucleotide sequence disclosed under GeneID: 8335. An example of a target mRNA encoding a HIST1H2AB polypeptide is the sequence available at Genbank accession number NM_003513.

Polynucleotides of the present disclosure that will act to inhibit expression of a HIST1H2AB polypeptide, include polynucleotides with a sense strand that is substantially identical or identical to a region of NM_003513. Examples of such polynucleotides that will act to inhibit expression of a polypeptide encoded by a HIST1H2AB coding region include SEQ ID NO: 61.

HPS4

In another aspect, the present disclosure includes polynucleotides that inhibit expression of a polypeptide encoded by a HPS4 coding region. As used herein a HPS4 coding region refers to the genomic nucleotide sequence disclosed under GeneID: 89781. An example of a target mRNA encoding a HPS4 polypeptide are the sequences available at Genbank accession numbers NM_022081 and NM_152841.

Polynucleotides of the present disclosure that will act to inhibit expression of a HPS4 polypeptide, include polynucleotides with a sense strand that is substantially identical or identical to a region of NM_022081 or NM_152841. Examples of such polynucleotides that will act to inhibit expression of a polypeptide encoded by a HPS4 coding region include SEQ ID NO: 62.

LHX8

In another aspect, the present disclosure includes polynucleotides that inhibit expression of a polypeptide encoded by a LHX8 coding region. As used herein a LHX8 coding region refers to the genomic nucleotide sequence disclosed under GeneID: 431707. An example of a target mRNA encoding a LHX8 polypeptide is the sequence available at Genbank accession number NM_001001933.

Polynucleotides of the present disclosure that will act to inhibit expression of a LHX8 polypeptide, include polynucleotides with a sense strand that is substantially identical or identical to a region of NM_001001933. Examples of such polynucleotides that will act to inhibit expression of a polypeptide encoded by a LHX8 coding region include SEQ ID NO: 63.

RPL23

In another aspect, the present disclosure includes polynucleotides that inhibit expression of a polypeptide encoded by a RPL23 coding region. As used herein a RPL23 coding region refers to the genomic nucleotide sequence disclosed under GeneID: 9349. An example of a target mRNA encoding a RPL23 polypeptide is the sequence available at Genbank accession number NM_000978.

Polynucleotides of the present disclosure that will act to inhibit expression of a RPL23 polypeptide, include polynucleotides with a sense strand that is substantially identical or identical to a region of NM_000978. Examples of such polynucleotides that will act to inhibit expression of a polypeptide encoded by a RPL23 coding region include SEQ ID NO: 64.

RPL32

In another aspect, the present disclosure includes polynucleotides that inhibit expression of a polypeptide encoded by a RPL32 coding region. As used herein a RPL32 coding region refers to the genomic nucleotide sequence disclosed under GeneID: 6161. An example of a target mRNA encoding a RPL32 polypeptide are the sequences available at Genbank accession numbers NM_000994 and NM_001007073.

Polynucleotides of the present disclosure that will act to inhibit expression of a RPL32 polypeptide, include polynucleotides with a sense strand that is substantially identical or identical to a region of NM_000994 or NM_001007073. Examples of such polynucleotides that will act to inhibit expression of a polypeptide encoded by a RPL32 coding region include SEQ ID NO: 65.

LOC730139

In another aspect, the present disclosure includes polynucleotides that inhibit expression of a polypeptide encoded by a LOC730139 coding region. As used herein a LOC730139 coding region refers to the genomic nucleotide sequence disclosed under GeneID: 730139. An example of a target mRNA encoding a LOC730139 polypeptide is the sequence of SEQ ID NO: 66.

Polynucleotides of the present disclosure that will act to inhibit expression of a LOC730139 polypeptide, include polynucleotides with a sense strand that is substantially identical or identical to a region of SEQ ID NO: 66. Examples of such polynucleotides that will act to inhibit expression of a polypeptide encoded by a LOC730139 coding region include SEQ ID NO: 67 and SEQ ID NO: 68.

LRRC39

In another aspect, the present disclosure includes polynucleotides that inhibit expression of a polypeptide encoded by a LRRC39 coding region. As used herein a LRRC39 coding region refers to the genomic nucleotide sequence disclosed under GeneID: 127495. An example of a target mRNA encoding a LRRC39 polypeptide is the sequence available at Genbank accession number NM_144620.

Polynucleotides of the present disclosure that will act to inhibit expression of a LRRC39 polypeptide, include polynucleotides with a sense strand that is substantially identical or identical to a region of NM_144620. Examples of such polynucleotides that will act to inhibit expression of a polypeptide encoded by a LRRC39 coding region include SEQ ID NO: 69 and SEQ ID NO: 70.

NRG1

In another aspect, the present disclosure includes polynucleotides that inhibit expression of a polypeptide encoded by a NRG1 coding region. As used herein a NRG1 coding region refers to the genomic nucleotide sequence disclosed under GeneID: 3084. An example of a target mRNA encoding a NRG1 polypeptide is the sequence available at Genbank accession number NM_001159995, NM_001159996, NM_001159999, NM_001160001, NM_001160002, NM_001160004, NM_001160005, NM_001160007, NM_001160008, NM_004495, NM_013956, NM_013957, NM_013958, NM_013959, NM_013960, NM_013962 and NM_013964.

Polynucleotides of the present disclosure that will act to inhibit expression of a NRG1 polypeptide, include polynucleotides with a sense strand that is substantially identical or identical to a region of NM_001159995, NM_001159996, NM_001159999, NM_001160001, NM_001160002, NM_001160004, NM_001160005, NM_001160007, NM_001160008, NM_004495, NM_013956, NM_013957, NM_013958, NM_013959, NM_013960, NM_013962 or NM_013964. Examples of such polynucleotides that will act to inhibit expression of a polypeptide encoded by a NRG1 coding region include SEQ ID NO: 71.

OR52A1

In another aspect, the present disclosure includes polynucleotides that inhibit expression of a polypeptide encoded by a OR52A1 coding region. As used herein a OR52A1 coding region refers to the genomic nucleotide sequence disclosed under GeneID: 23538. An example of a target mRNA encoding a OR52A1 polypeptide is the sequence available at Genbank accession number NM_012375.

Polynucleotides of the present disclosure that will act to inhibit expression of a OR52A 1 polypeptide, include polynucleotides with a sense strand that is substantially identical or identical to a region of NM_012375. Examples of such polynucleotides that will act to inhibit expression of a polypeptide encoded by a OR52A1 coding region include SEQ ID NO: 72 and SEQ ID NO: 73.

PLEKHH1

In another aspect, the present disclosure includes polynucleotides that inhibit expression of a polypeptide encoded by a PLEKHH1 coding region. As used herein a PLEKHH1 coding region refers to the genomic nucleotide sequence disclosed under GeneID: 57475. An example of a target mRNA encoding a PLEKHH1 polypeptide is the sequence available at Genbank accession number NM_020715.

Polynucleotides of the present disclosure that will act to inhibit expression of a PLEKHH1 polypeptide, include polynucleotides with a sense strand that is substantially identical or identical to a region of NM_020715. Examples of such polynucleotides that will act to inhibit expression of a polypeptide encoded by a PLEKHH1 coding region include SEQ ID NO: 74.

PTPN13

In another aspect, the present disclosure includes polynucleotides that inhibit expression of a polypeptide encoded by a PTPN13 coding region. As used herein a PTPN13 coding region refers to the genomic nucleotide sequence disclosed under GeneID: 5783. An example of a target mRNA encoding a PTPN13 polypeptide is the sequence available at Genbank accession number NM_006264, NM_080683, NM_080684 and NM_080685.

Polynucleotides of the present disclosure that will act to inhibit expression of a PTPN13 polypeptide, include polynucleotides with a sense strand that is substantially identical or identical to a region of NM_006264, NM_080683, NM_080684 or NM_080685. Examples of such polynucleotides that will act to inhibit expression of a polypeptide encoded by a PTPN13 coding region include SEQ ID NO: 75.

PTPRJ

In another aspect, the present disclosure includes polynucleotides that inhibit expression of a polypeptide encoded by a PTPRJ coding region. As used herein a PTPRJ coding region refers to the genomic nucleotide sequence disclosed under GeneID: 5795. An example of a target mRNA encoding a PTPRJ polypeptide is the sequence available at Genbank accession number NM_001098503 and NM_002843.

Polynucleotides of the present disclosure that will act to inhibit expression of a PTPRJ polypeptide, include polynucleotides with a sense strand that is substantially identical or identical to a region of NM_001098503 or NM_002843. Examples of such polynucleotides that will act to inhibit expression of a polypeptide encoded by a PTPN13 coding region include SEQ ID NO: 76 and SEQ ID NO: 77.

RLN1

In another aspect, the present disclosure includes polynucleotides that inhibit expression of a polypeptide encoded by a RLN1 coding region. As used herein a RLN1 coding region refers to the genomic nucleotide sequence disclosed under GeneID: 6013. An example of a target mRNA encoding a RLN1 polypeptide is the sequence available at Genbank accession number NM_006911.

Polynucleotides of the present disclosure that will act to inhibit expression of a RLN1 polypeptide, include polynucleotides with a sense strand that is substantially identical or identical to a region of NM_006911. Examples of such polynucleotides that will act to inhibit expression of a polypeptide encoded by a RLN1 coding region include SEQ ID NO: 78.

RNF19A

In another aspect, the present disclosure includes polynucleotides that inhibit expression of a polypeptide encoded by a RNF19A coding region. As used herein a RNF19A coding region refers to the genomic nucleotide sequence disclosed under GeneID: 25897. An example of a target mRNA encoding a RNF19A polypeptide are the sequence available at Genbank accession numbers NM_015435 and NM_183419.

Polynucleotides of the present disclosure that will act to inhibit expression of a RNF19A polypeptide, include polynucleotides with a sense strand that is substantially identical or identical to a region of NM_015435 or NM_183419. Examples of such polynucleotides that will act to inhibit expression of a polypeptide encoded by a RLN1 coding region include SEQ ID NO: 79.

SLC7A 14

In another aspect, the present disclosure includes polynucleotides that inhibit expression of a polypeptide encoded by a SLC7A14 coding region. As used herein a SLC7A14 coding region refers to the genomic nucleotide sequence disclosed under GeneID: 57709. An example of a target mRNA encoding a SLC7A14 polypeptide is the sequence available at Genbank accession number NM_020949.

Polynucleotides of the present disclosure that will act to inhibit expression of a SLC7A14 polypeptide, include polynucleotides with a sense strand that is substantially identical or identical to a region of NM_020949. Examples of such polynucleotides that will act to inhibit expression of a polypeptide encoded by a SLC7A14 coding region include SEQ ID NO: 80.

ST8SL43

In another aspect, the present disclosure includes polynucleotides that inhibit expression of a polypeptide encoded by a ST8SIA3 coding region. As used herein a ST8SIA3 coding region refers to the genomic nucleotide sequence disclosed under GeneID: 51046. An example of a target mRNA encoding a ST8SIA3 polypeptide is the sequence available at Genbank accession number NM_015879.

Polynucleotides of the present disclosure that will act to inhibit expression of a ST8SIA3 polypeptide, include polynucleotides with a sense strand that is substantially identical or identical to a region of NM_015879. Examples of such polynucleotides that will act to inhibit expression of a polypeptide encoded by a SLC7A14 coding region include SEQ ID NO: 81 and SEQ ID NO: 82.

TMTC4

In another aspect, the present disclosure includes polynucleotides that inhibit expression of a polypeptide encoded by a TMTC4 coding region. As used herein a TMTC4 coding region refers to the genomic nucleotide sequence disclosed under GeneID: 84899. An example of a target mRNA encoding a TMTC4 polypeptide are the sequences available at Genbank accession numbers NM_001079669 and NM_032813.

Polynucleotides of the present disclosure that will act to inhibit expression of a TMTC4 polypeptide, include polynucleotides with a sense strand that is substantially identical or identical to a region of NM_001079669 or NM_032813. Examples of such polynucleotides that will act to inhibit expression of a polypeptide encoded by a TMTC4 coding region include SEQ ID NO: 84 and SEQ ID NO: 85.

TTN

In another aspect, the present disclosure includes polynucleotides that inhibit expression of a polypeptide encoded by a TTN coding region. As used herein a TTN coding region refers to the genomic nucleotide sequence disclosed under GeneID: 7273. An example of a target mRNA encoding a TTN polypeptide is the sequence available at Genbank accession numbers NM_003319, NM_133378, NM_133379, NM_133432 and NM_133437.

Polynucleotides of the present disclosure that will act to inhibit expression of a TTN polypeptide, include polynucleotides with a sense strand that is substantially identical or identical to a region of NM_003319, NM_133378, NM_133379, NM_133432 or NM_133437. Examples of such polynucleotides that will act to inhibit expression of a polypeptide encoded by a TTN coding region include SEQ ID NO: 86 and SEQ ID NO: 87.

UBXN7

In another aspect, the present disclosure includes polynucleotides that inhibit expression of a polypeptide encoded by a UBXN7 coding region. As used herein a UBXN7 coding region refers to the genomic nucleotide sequence disclosed under GeneID: 26043. An example of a target mRNA encoding a UBXN7 polypeptide is the sequence available at Genbank accession number NM_015562.

Polynucleotides of the present disclosure that will act to inhibit expression of a UBXN7 polypeptide, include polynucleotides with a sense strand that is substantially identical or identical to a region of NM_015562. Examples of such polynucleotides that will act to inhibit expression of a polypeptide encoded by a UBXN7 coding region include SEQ ID NO: 88.

YPEL2

In another aspect, the present disclosure includes polynucleotides that inhibit expression of a polypeptide encoded by a YPEL2 coding region. As used herein a YPEL2 coding region refers to the genomic nucleotide sequence disclosed under GeneID: 388403. An example of a target mRNA encoding a YPEL2 polypeptide is the sequence available at Genbank accession number NM_001005404.

Polynucleotides of the present disclosure that will act to inhibit expression of a YPEL2 polypeptide, include polynucleotides with a sense strand that is substantially identical or identical to a region of NM_001005404. Examples of such polynucleotides that will act to inhibit expression of a polypeptide encoded by a YPEL2 coding region include SEQ ID NO: 89 and SEQ ID NO: 90.

ZNF251

In another aspect, the present disclosure includes polynucleotides that inhibit expression of a polypeptide encoded by a ZNF251 coding region. As used herein a ZNF251 coding region refers to the genomic nucleotide sequence disclosed under GeneID: 90987. An example of a target mRNA encoding a ZNF251 polypeptide is the sequence available at Genbank accession number NM_138367.

Polynucleotides of the present disclosure that will act to inhibit expression of a ZNF251 polypeptide, include polynucleotides with a sense strand that is substantially identical or identical to a region of NM_138367. Examples of such polynucleotides that will act to inhibit expression of a polypeptide encoded by a ZNF251 coding region include SEQ ID NO: 91 and SEQ ID NO: 92.

MERTK

In another aspect, the present disclosure includes polynucleotides that inhibit expression of a polypeptide encoded by a MERTK coding region. As used herein a MERTK coding region refers to the genomic nucleotide sequence disclosed under GeneID: 10461. An example of a target mRNA encoding a MERTK polypeptide is the sequence available at Genbank accession number NM_006343.

Polynucleotides of the present disclosure that will act to inhibit expression of a MERTK polypeptide, include polynucleotides with a sense strand that is substantially identical or identical to a region of NM_006343. Examples of such polynucleotides that will act to inhibit expression of a polypeptide encoded by a MERTK coding region include SEQ ID NO: 93, SEQ ID NO: 94 and SEQ ID NO: 95.

SCG2

In another aspect, the present disclosure includes polynucleotides that inhibit expression of a polypeptide encoded by a SCG2 coding region. As used herein a SCG2 coding region refers to the genomic nucleotide sequence disclosed under GeneID: 7857. An example of a target mRNA encoding a SCG2 polypeptide is the sequence available at Genbank accession number NM_003469.

Polynucleotides of the present disclosure that will act to inhibit expression of a SCG2 polypeptide, include polynucleotides with a sense strand that is substantially identical or identical to a region of NM_003469. Examples of such polynucleotides that will act to inhibit expression of a polypeptide encoded by a SCG2 coding region include SEQ ID NO: 96, SEQ ID NO: 97 and SEQ ID NO: 98.

A person skilled in the art will appreciate that other polynucleotides can be designed to inhibit the target host factor polypeptides.

Methods for designing such molecules are known in the art. For instance, polynucleotides that inhibit the expression of one of the polypeptides described herein may be identified by the use of cell lines including, but not limited to, HT29 and KM20. A candidate polynucleotide is the polynucleotide that is being tested to determine if it decreases expression of one of the polypeptides described herein. The candidate polynucleotide can be identical to nucleotides located in the region encoding the polypeptide, or located in the 5' or 3' untranslated regions of the mRNA. Other methods are known in the art and used for designing and selecting candidate polynucleotides. Candidate polynucleotides are typically screened using publicly available algorithms (e.g., BLAST) to compare the candidate polynucleotide sequences with coding sequences. Those that are likely to form a duplex with an mRNA expressed by a non-target coding region are typically eliminated from further consideration. The remaining candidate polynucleotides may then be tested to determine if they inhibit expression of one of the polypeptides described herein.

In general, candidate polynucleotides are individually tested by introducing a candidate polynucleotide into a cell that expresses the appropriate polypeptide. The candidate polynucleotides may be prepared in vitro and then introduced into a cell. Methods for in vitro synthesis include, for instance, chemical synthesis with a conventional DNA/RNA synthesizer. Commercial suppliers of synthetic polynucleotides and reagents for such synthesis are well known. Methods for in vitro synthesis also include, for instance, in vitro transcription using a circular or linear vector in a cell free system.

When evaluating whether a candidate polynucleotide functions to inhibit expression of one of the polypeptides described herein, the amount of target mRNA in a cell containing a candidate polynucleotide can be measured and compared to the same type of cell that does not contain the candidate polynucleotide. Methods for measuring mRNA levels in a cell are known in the art. Such methods include quantitative reverse-transcriptase polymerase chain reaction (RT-PCR). Primers and specific conditions for amplification of an mRNA vary depending upon the mRNA, and can be readily determined by the skilled person. Other methods include, for instance, Northern blotting, and array analysis.

Other methods for evaluating whether a candidate polynucleotide functions to inhibit expression of one of the polypeptides described herein include monitoring the polypeptide. For instance, assays can be used to measure a decrease in the amount of polypeptide encoded by the mRNA, or to measure a decrease in the activity of the polypeptide encoded by the mRNA. Methods for measuring a decrease in the amount of a polypeptide include assaying for the polypeptide present in cells containing a candidate polynucleotide and comparing to the same type of cell that does not contain the candidate polynucleotide. For instance, antibody to one of the polypeptides described herein can be used in Western immunoblot, immunoprecipitation, or immunohistochemistry.

Methods for measuring a decrease in the activity of one of the polypeptides, e.g., ABI2, ARRDC3, BAD, BRCA1, C17orf85, C1orf71, C6orf162, CCNJL, CFL1, GON4L, HCG 1986447, HIST1H2AB, HPS4, LHX8, RPS25, RPL23, RPL32, LOC730139, LRRC39, MALT1, MX1, MERTK, MX2, NRG1, OR52A1, PLEKHH1, PTPN13, PTPRJ, RLN1, RNF19A, SH3BP4, SLC7A14, ST8SIA3, STX3, TMC6, TMTC4, TNFSF12-TNFSF13, TNFSF13, TTN, UBXN7, USP47, WNK2, YPEL2, ZNF251 or SCG2, vary depending upon the polypeptide. In general, methods for measuring a decrease in the activity of a polypeptide include assaying the appropriate activity present in a cell containing a candidate polynucleotide and comparing to the same type of cell that does not contain the candidate polynucleotide. Methods for measuring the activity of a ABI2, ARRDC3, BAD, BRCA1, C17orf85, C1orf71, C6orf162, CCNJL, CFL1, GON4L, HCG 1986447, HIST1H2AB, HPS4, LHX8, RPS25, RPL23, RPL32, LOC730139, LRRC39, MALT1, MX1, MERTK, MX2, NRG1, OR52A1, PLEKHH1, PTPN13, PTPRJ, RLN1, RNF19A, SH3BP4, SLC7A14, ST8SIA3, STX3, TMC6, TMTC4, TNFSF12-TNFSF13, TNFSF13, TTN, UBXN7, USP47, WNK2, YPEL2, ZNF251 or SCG2 polypeptide are known in the art.

A candidate polynucleotide that is able to decrease the expression of a polypeptide encoded by a ABI2, ARRDC3, BAD, BRCA1, C17orf85, C1orf71, C6orf162, CCNJL, CFL1, GON4L, HCG 1986447, HIST1H2AB, HPS4, LHX8, RPS25, RPL23, RPL32, LOC730139, LRRC39, MALT1, MX1, MERTK, MX2, NRG1, OR52A1, PLEKHH1, PTPN13, PTPRJ, RLN1, RNF19A, SH3BP4, SLC7A14, ST8SIA3, STX3, TMC6, TMTC4, TNFSF12-TNFSF13, TNFSF13, TTN, UBXN7, USP47, WNK2, YPEL2, ZNF25 or SCG2 coding region, a polypeptide encoded by a ABI2, ARRDC3, BAD, BRCA1, C17orf85, C1orf71, C6orf162, CCNJL, CFL1, GON4L, HCG 1986447, HIST1H2AB, HPS4, LHX8, RPS25, RPL23, RPL32, LOC730139, LRRC39, MALT1, MX1, MERTK, MX2, NRG1, OR52A1, PLEKHH1, PTPN13, PTPRJ, RLN1, RNF19A, SH3BP4, SLC7A14, ST8SIA3, STX3, TMC6, TMTC4, TNFSF12-TNFSF13, TNFSF13, TTN, UBXN7, USP47, WNK2, YPEL2, ZNF251 or SCG2 coding region, or a target mRNA by at least 80%, or at least 90%, or up to 100%, is considered to be a polynucleotide of the present disclosure.

An inhibiting polynucleotide of the present disclosure can be present in a vector. A vector is a replicating polynucleotide, such as a plasmid, phage, or cosmid, to which another polynucleotide may be attached so as to bring about the replication of the attached polynucleotide. Construction of vectors containing a polynucleotide employs standard ligation techniques known in the art. See, e.g., Sambrook et al, Molecular Cloning: A Laboratory Manual., Cold Spring Harbor Laboratory Press (1989). A vector can provide for further cloning (amplification of the polynucleotide), i.e., a cloning vector, or for expression of the polynucleotide, i.e., an expression vector. The term vector includes, but is not limited to, plasmid vectors, viral vectors, cosmid vectors, or artificial chromosome vectors. Examples of viral vectors include, for instance, adenoviral vectors, adeno-associated viral vectors, lentiviral vectors, retroviral vectors, and herpes virus vectors. A vector may result in integration into a cell's genomic DNA. Typically, a vector is capable of replication in a bacterial host, for instance E. coli. Preferably the vector is a plasmid. A polynucleotide of the present disclosure can be present in a vector as two separate complementary polynucleotides, each of which can be expressed to yield a sense and an antisense strand of a dsRNA, or as a single polynucleotide containing a sense strand, a loop region, and an antisense strand, which can be expressed to yield an RNA polynucleotide having a sense and an antisense strand of the dsRNA.

Selection of a vector depends upon a variety of desired characteristics in the resulting construct, such as a selection marker, vector replication rate, and the like. Suitable host cells for cloning or expressing the vectors herein are prokaryotic or eukaryotic cells. Suitable eukaryotic cells include mammalian cells, such as murine cells and human cells. Suitable prokaryotic cells include eubacteria, such as gram-negative organisms, for example, *E. coli.*

An expression vector optionally includes regulatory sequences operably linked to the polynucleotide of the present disclosure. Typically, the promoter results in the production of an RNA polynucleotide. Examples of such promoters include, but are not limited to, those that cause binding of an RNA polymerase III complex to initiate transcription of an operably linked polynucleotide of the present disclosure. Examples of such promoters include U6 and H1 promoters. Vectors may also include inducible or regulatable promoters for expression of a polynucleotide of the present disclosure in a particular tissue or intracellular environment. The polynucleotide of the present disclosure also typically includes a transcription terminator. Suitable transcription terminators are known in the art and include, for instance, a stretch of 5 consecutive thymidine nucleotides.

Polynucleotides of the present disclosure can be produced in vitro or in vivo. For instance, methods for in vitro synthesis include, but are not limited to, chemical synthesis with a conventional DNA/RNA synthesizer. Commercial suppliers of synthetic polynucleotides and reagents for such synthesis are well known. Methods for in vitro synthesis also include, for instance, in vitro transcription using a circular or linear expression vector in a cell free system. Expression vectors can also be used to produce a polynucleotide of the present disclosure in a cell, and the polynucleotide then isolated from the cell.

The present disclosure is further directed to methods of treating viral infection and virus-mediated cytotoxicity by inhibiting the target host factors of the present disclosure.

RNAi, antisense, ribozyme and other nucleic acid therapeutics can be used to inhibit expression of ABI2, ARRDC3, BAD, BRCA1, C17orf85, C1orf71, C6orf162, CCNJL, CFL1, GON4L, HCG 1986447, HIST1H2AB, HPS4, LHX8, RPS25, RPL23, RPL32, LOC730139, LRRC39, MALT1, MX1, MERTK, MX2, NRG1, OR52A1, PLEKHH1, PTPN13, PTPRJ, RLN1, RNF19A, SH3BP4, SLC7A14, ST8SIA3, STX3, TMC6, TMTC4, TNFSF12-TNFSF13, TNFSF13, TTN, UBXN7, USP47, WNK2, YPEL2, ZNF251 or SCG2 or a combination thereof in patients suffering from virus infection. For example, a ABI2, ARRDC3, BAD, BRCA1, C17orf85, C1orf71, C6orf162, CCNJL, CFL1, GON4L, HCG 1986447, HIST1H2AB, HPS4, LHX8, RPS25, RPL23, RPL32, LOC730139, LRRC39, MALT1, MX1, MERTK, MX2, NRG1, OR52A1, PLEKHH1, PTPN13, PTPRJ, RLN1, RNF19A, SH3BP4, SLC7A14, ST8SIA3, STX3, TMC6, TMTC4, TNFSF12-TNFSF13, TNFSF13, TTN, UBXN7, USP47, WNK2, YPEL2, ZNF251 and/or SCG2 antisense strand (either RNA or DNA) may be directly introduced into the cells in a form that is capable of binding to the mRNA transcripts. Alternatively, a vector containing a sequence which once within the target cells, is transcribed into the appropriate antisense mRNA, may be administered. Antisense nucleic acids which hybridize to target mRNA decrease or inhibit production of the polypeptide product encoded by a gene by associating with the normally single-stranded mRNA transcript, thereby interfering with translation and thus, expression of the protein. For example, DNA containing a promoter, e.g., a tissue-specific is operably linked to a DNA sequence (an antisense template), which is transcribed into an antisense RNA. By "operably linked" is meant that a coding sequence and a regulatory sequence(s) (i.e., a promoter) are connected in such a way as to permit gene expression when the appropriate molecules (e.g., transcriptional activator proteins) are bound to the regulatory sequence(s).

Oligonucleotides complementary to various portions of ABI2, ARRDC3, BAD, BRCA1, C17orf85, C1orf71, C6orf162, CCNJL, CFL1, GON4L, HCG 1986447, HIST1H2AB, HPS4, LHX8, RPS25, RPL23, RPL32, LOC730139, LRRC39, MALT1, MX1, MERTK, MX2, NRG1, OR52A1, PLEKHH1, PTPN13, PTPRJ, RLN1, RNF19A, SH3BP4, SLC7A14, ST8SIA3, STX3, TMC6, TMTC4, TNFSF12-TNFSF13, TNFSF13, TTN, UBXN7, USP47, WNK2, YPEL2, ZNF251 or SCG2 can be determined in vitro for their ability to decrease production of ABI2, ARRDC3, BAD, BRCA1, C17orf85, C1orf71, C6orf162, CCNJL, CFL1, GON4L, HCG 1986447, HIST1H2AB, HPS4, LHX8, RPS25, RPL23, RPL32, LOC730139, LRRC39, MALT1, MX1, MERTK, MX2, NRG1, OR52A1, PLEKHH1, PTPN13, PTPRJ, RLN1, RNF19A, SH3BP4, SLC7A14, ST8SIA3, STX3, TMC6, TMTC4, TNFSF12-TNFSF13, TNFSF13, TTN, UBXN7, USP47, WNK2, YPEL2, ZNF251 or SCG2 in human cells according to standard methods. A reduction in ABI2, ARRDC3, BAD, BRCA1, C17orf85, C1orf71, C6orf162, CCNJL, CFL1, GON4L, HCG 1986447, HIST1H2AB, HPS4, LHX8, RPS25, RPL23, RPL32, LOC730139, LRRC39, MALT1, MX1, MERTK, MX2, NRG1, OR52A1, PLEKHH1, PTPN13, PTPRJ, RLN1, RNF19A, SH3BP4, SLC7A14, ST8SIA3, STX3, TMC6, TMTC4, TNFSF12-TNFSF13, TNFSF13, TTN, UBXN7, USP47, WNK2, YPEL2, ZNF251 or SCG2 gene product in cells contacted with the candidate antisense composition compared to cells cultured in the absence of the candidate composition is detected using ABI2, ARRDC3, BAD, BRCA1, C17orf85, C1orf71, C6orf162, CCNJL, CFL1, GON4L, HCG 1986447, HIST1H2AB, HPS4, LHX8, RPS25, RPL23, RPL32, LOC730139, LRRC39, MALT1, MX1, MERTK, MX2, NRG1, OR52A1, PLEKHH1, PTPN13, PTPRJ, RLN1, RNF19A, SH3BP4, SLC7A14, ST8SIA3, STX3, TMC6, TMTC4, TNFSF12-TNFSF13, TNFSF13, TTN, UBXN7, USP47, WNK2, YPEL2, ZNF251 or SCG2-specific antibodies or other detection strategies. Sequences which decrease production of ABI2, ARRDC3, BAD, BRCA1, C17orf85, C1orf71, C6orf162, CCNJL, CFL1, GON4L, HCG 1986447, HIST1H2AB, HPS4, LHX8, RPS25, RPL23, RPL32, LOC730139, LRRC39, MALT1, MX1, MERTK, MX2, NRG1, OR52A1, PLEKHH1, PTPN13, PTPRJ, RLN1, RNF19A, SH3BP4, SLC7A14, ST8SIA3, STX3, TMC6, TMTC4, TNFSF12-TNFSF13, TNFSF13, TTN, UBXN7, USP47, WNK2, YPEL2, ZNF251 or SCG2 in vitro cell-based or cell-free assays are then be tested in vivo in rats or mice to confirm decreased ABI2, ARRDC3, BAD, BRCA1, C17orf85, C1orf71, C6orf162, CCNJL, CFL1, GON4L, HCG 1986447, HIST1H2AB, HPS4, LHX8, RPS25, RPL23, RPL32, LOC730139, LRRC39, MALT1, MX1, MERTK, MX2, NRG1, OR52A1, PLEKHH1, PTPN13, PTPRJ, RLN1, RNF19A, SH3BP4, SLC7A14, ST8SIA3, STX3, TMC6, TMTC4, TNFSF12-TNFSF13, TNFSF13, TTN, UBXN7, USP47, WNK2, YPEL2, ZNF251 or SCG2 production in animals with virus infection.

Antisense therapy may be carried out by administering to a patient an antisense nucleic acid by standard vectors and/or gene delivery systems. Suitable gene delivery systems may include liposomes, polymers, receptor-mediated delivery systems, naked DNA, and viral vectors such as herpes viruses, retroviruses, adenoviruses and adeno-associated viruses, among others. A therapeutic nucleic acid composition is formulated in a pharmaceutically acceptable carrier. The therapeutic composition may also include a gene delivery system as described above.

The present disclosure is also directed to compositions including one or more inhibitors of the target host factor polypeptide of the present disclosure. Such compositions typically include a pharmaceutically acceptable carrier. As used herein "pharmaceutically acceptable carrier" includes saline, solvents, dispersion media, coatings, antibacterial and antifungal agents, isotonic and absorption delaying agents, and the like, compatible with pharmaceutical administration. Additional active compounds can also be incorporated into the compositions.

Pharmaceutically acceptable carriers are biologically compatible vehicles which are suitable for administration to an animal: e.g., physiological saline. A therapeutically effective amount of a compound is an amount which is capable of producing a medically desirable result such as reduced production of a ABI2, ARRDC3, BAD, BRCA1, C17orf85, C1orf71, C6orf162, CCNJL, CFL1, GON4L, HCG 1986447, HIST1H2AB, HPS4, LHX8, RPS25, RPL23, RPL32, LOC730139, LRRC39, MALT1, MX1, MERTK, MX2, NRG1, OR52A1, PLEKHH1, PTPN13, PTPRJ, RLN1, RNF19A, SH3BP4, SLC7A14, ST8SIA3, STX3, TMC6, TMTC4, TNFSF12-TNFSF13, TNFSF13, TTN, UBXN7, USP47, WNK2, YPEL2, ZNF251 or SCG2 gene product in a treated animal.

Parenteral administration, such as intravenous, subcutaneous, intramuscular, and intraperitoneal delivery routes, may be used to deliver nucleic acids or ABI2, ARRDC3, BAD, BRCA1, C17orf85, C1orf71, C6orf162, CCNJL, CFL1, GON4L, HCG 1986447, HIST1H2AB, HPS4, LHX8, RPS25, RPL23, RPL32, LOC730139, LRRC39, MALT1, MX1, MERTK, MX2, NRG1, OR52A1, PLEKHH1, PTPN13, PTPRJ, RLN1, RNF19A, SH3BP4, SLC7A14, ST8SIA3, STX3, TMC6, TMTC4, TNFSF12-TNFSF13, TNFSF13, TTN, UBXN7, USP47, WNK2, YPEL2, ZNF251 or SCG2-inhibitory peptides on non-peptide compounds. Liposome formulations of therapeutic compounds may also facilitate activity.

Dosages for any one patient depends upon many factors, including the patient's size, body surface area, age, the particular nucleic acid to be administered, sex, time and route of administration, general health, and other drugs being administered concurrently.

A list of sequence identification numbers of the present disclosure is given in Table 7.

TABLE 7

List of Sequence Identification numbers.

| SEQ ID NO: | Description | Table/Figure |
|---|---|---|
| 1 | BAD shRNA V2HS_15289 | Table 2 and 8A |
| 2 | BAD shRNA V2HS_243025 | Table 2 and 8A |
| 3 | BAD shRNA V2HS_201511 | Table 2 and 8A |
| 4 | BAD shRNA V2HS_202976 | Table 2 and 8A |
| 5 | BAD shRNA V2HS_262043 | Table 2 and 8A |
| 6 | BAD siRNA J-003870-09 | Table 2 |
| 7 | BAD siRNA J-003870-10 | Table 2 |
| 8 | BAD siRNA J-003870-11 | Table 2 |
| 9 | BAD siRNA J-003870-12 | Table 2 |
| 10 | BAD transcript variant 1 (NM_004322.3) | FIG. 1A |
| 11 | TNFSF12-TNFSF13/TNFSF13 shRNA V2HS_17313 | Table 3 and 8A |
| 12 | TNFSF12-TNFSF13/TNFSF13 shRNA V2HS_17314 | Table 3 and 8A |
| 13 | TNFSF12-TNFSF13/TNFSF13 shRNA V2HS_17316 | Table 3 and 8A |

TABLE 7-continued

List of Sequence Identification numbers.

| SEQ ID NO: | Description | Table/Figure |
|---|---|---|
| 14 | TNFSF12-TNFSF13/TNFSF13 shRNA V2HS_17317 | Table 3 and 8A |
| 15 | TNFSF12-TNFSF13/TNFSF13 shRNA V2HS_17318 | Table 3 and 8A |
| 16 | TNFSF12-TNFSF13/TNFSF13 siRNA J-032530-05 | Table 3 |
| 17 | TNFSF12-TNFSF13/TNFSF13 siRNA J-032530-06 | Table 3 |
| 18 | TNFSF12-TNFSF13/TNFSF13 siRNA J-032530-07 | Table 3 |
| 19 | TNFSF12-TNFSF13/TNFSF13 siRNA J-032530-08 | Table 3 |
| 20 | TNFSF12-TNFSF13 siRNA J-011523-05 | Table 4 |
| 21 | TNFSF12-TNFSF13 siRNA J-011523-06 | Table 4 |
| 22 | TNFSF12-TNFSF13 siRNA J-011523-07 | Table 4 |
| 23 | TNFSF12-TNFSF13 siRNA J-011523-08 | Table 4 |
| 24 | MX2 transcript | FIG. 1C |
| 25 | MX2 shRNA V2HS_152031 | Table 5 and 8A |
| 26 | MX2 siRNA J-011736-05 | Table 5 |
| 27 | MX2 siRNA J-011736-06 | Table 5 |
| 28 | MX2 siRNA J-011736-07 | Table 5 |
| 29 | MX2 siRNA J-011736-08 | Table 5 |
| 30 | USP 47 transcript | FIG. 1D |
| 31 | USP47 shRNA V2HS_174637 | Table 6 and 8A |
| 32 | USP47 shRNA V2HS_174639 | Table 6 and 8A |
| 33 | USP47 shRNAV2HS_174641 | Table 6 and 8A |
| 34 | USP47 shRNA V2HS_174642 | Table 6 and 8A |
| 35 | USP47 shRNA V2HS_218228 | Table 6 and 8A |
| 36 | USP47 siRNA J-006093-05 | Table 6 and 8A |
| 37 | USP47 siRNA J-006093-06 | Table 6 and 8A |
| 38 | USP47 siRNA J-006093-07 | Table 6 and 8A |
| 39 | USP47 siRNA J-006093-08 | Table 6 and 8A |
| 40 | USP47 shRNA V2HS-174640 | Table 6 and 8A |
| 41 | MX1 shRNA V2HS_152026 | Table 8A |
| 42 | MX1 shRNA V2HS_152028 | Table 8A |
| 43 | MALT1 shRNA V2HS_84222 | Table 8A |
| 44 | RPS25 shRNA V2HS_93855 | Table 8A |
| 45 | SH3BP4 shRNA V2HS_260346 | Table 8A |
| 46 | HCG 1986447 transcript | FIG. 1E |
| 47 | HCG 1986447 shRNA V2HS_29650 | Table 8A |
| 48 | WNK2 shRNA V2HS_238923 | Table 8A |
| 49 | TMC6 shRNA V2HS_198493 | Table 8A |
| 50 | CFL1 shRNA V2HS_64314 | Table 8A |
| 51 | ABI2 shRNA V2HS_196634 | Table 8A |
| 52 | ARRDC3 shRNA V2HS_217697 | Table 8A |
| 53 | BRCA1 shRNA V2HS_254648 | Table 8A |
| 54 | BRCA1 shRNA V2HS_280394 | Table 8A |
| 55 | BRCA1 shRNA V2HS_255064 | Table 8A |
| 56 | C17orf85 shRNA V2HS_176062 | Table 8A |
| 57 | C1orf71 shRNA V2HS_44617 | Table 8A |
| 58 | C6orf162 shRNA V2HS_35766 | Table 8A |
| 59 | CCNJL shRNA V2HS_136349 | Table 8A |
| 60 | GON4L shRNA V2HS_138350 | Table 8A |
| 61 | HIST1H2AB shRNA V2HS_33954 | Table 8A |
| 62 | HPS4 shRNA V2HS_70495 | Table 8A |
| 63 | LHX8 shRNA V2HS_75780 | Table 8A |
| 64 | RPL23 shRNA V2HS_23046 | Table 8A |
| 65 | RPL32 shRNA V2HS_165267 | Table 8A |
| 66 | LOC730139 transcript | FIG. 1F |
| 67 | LOC730139 shRNA V2HS_25169 | Table 8A |
| 68 | LOC730139 shRNA V2HS_25168 | Table 8A |
| 69 | LRRC39 shRNA V2HS_18852 | Table 8A |
| 70 | LRRC39 shRNA V2HS_18851 | Table 8A |
| 71 | NRG1 shRNA V2HS_84939 | Table 8A |
| 72 | OR52A1 shRNA V2HS_244561 | Table 8A |
| 73 | OR52A1 shRNA V2HS_49243 | Table 8A |
| 74 | PLEKHH1 shRNA V2HS_46786 | Table 8A |
| 75 | PTPN13 shRNA V2HS_57273 | Table 8A |
| 76 | PTPRJ shRNA V2HS_91546 | Table 8A |
| 77 | PTPRJ shRNA V2HS_171000 | Table 8A |
| 78 | RLN1 shRNA V2HS_94799 | Table 8A |
| 79 | RNF19A shRNA V2HS_96523 | Table 8A |
| 80 | SLC7A14 shRNA V2HS_57109 | Table 8A |
| 81 | ST8SIA3 shRNA V2HS_114878 | Table 8A |
| 82 | ST8SIA3 shRNA V2HS_114879 | Table 8A |
| 83 | STX3 shRNA V2HS_33937 | Table 8A |

TABLE 7-continued

List of Sequence Identification numbers.

| SEQ ID NO: | Description | Table/Figure |
|---|---|---|
| 84 | TMTC4 shRNA V2HS_177667 | Table 8A |
| 85 | TMTC4 shRNA V2HS_275500 | Table 8A |
| 86 | TTN shRNA V2HS_171633 | Table 8A |
| 87 | TTN shRNA V2HS_171637 | Table 8A |
| 88 | UBXN7 shRNA V2HS_130208 | Table 8A |
| 89 | YPEL2 shRNA V2HS_77698 | Table 8A |
| 90 | YPEL2 shRNA V2HS_77701 | Table 8A |
| 91 | ZNF251 shRNA V2HS_250202 | Table 8A |
| 92 | ZNF251 shRNA V2HS_215547 | Table 8A |
| 93 | MERTK shRNA V2HS_1643 | Table 8B |
| 94 | MERTK shRNA V2HS_168768 | Table 8B |
| 95 | MERTK shRNA V2HS_197158 | Table 8B |
| 96 | SCG2 shRNA V2HS_172404 | Table 8B |
| 97 | SCG2 shRNA V2HS_172401 | Table 8B |
| 98 | SCG2 shRNA V2HS_172400 | Table 8B |
| 99 | TNFSF12-TNFSF13 transcript | FIG. 1G |
| 100 | TNFSF13 transcript variant alpha | FIG. 1H |
| 101 | TNFSF13 transcript variant beta | FIG. 1I |
| 102 | TNFSF13 transcript variant gamma | FIG. 1J |
| 103 | BAD transcript variant 2 (NM_032989) | FIG. 1B |

The present invention will be further illustrated in the following examples. However it is to be understood that these examples are for illustrative purposes only, and should not be used to limit the scope of the present invention in any manner.

EXAMPLE 1

*Drosophila*-based screens' have been used to identify genes involved in influenza replication, and two very recent studies employed genome-wide siRNA arrays to identify mammalian host proteins involved in various stages of the influenza virus lifecycle.[6,7] Severe influenza pathology has been seen with pandemic 1918 virus[8] and SOIV-infected patient lung pathology showed alveolar damage and hemorrhage suggestive of atypical immune responses.[9] Studies in pigtailed macaques reported that the activation of apoptotic pathways may contribute to tissue damage during infection[10].

Human genes (target host factors) required for viral replication and cytotoxicity were identified. Interference with these proteins provided a basis for inhibiting viral production while protecting infected cells from virus-induced death.

Multiple genome-wide lentiviral-based shRNAmir screens consistently identified 35 annotated candidate genes associated with cell survival despite infection (see Table 1). Initial analysis of 4 candidate genes (BAD, INFSF12-13/INFSF13, MX2, and USP47), using lentiviral-based and synthetic RNAi silencing confirmed protective roles with dramatic inhibition of virus replication after challenge with influenza viruses of multiple H and N types, including the contemporary pandemic swine-origin H1N1 virus.

High Throughput Genome-Wide Screens

The availability of human genome-wide lentiviral-based shRNAi (short hairpin RNA interference) libraries provides the ability to identify host genes important in influenza pathology. RNAi regulates gene expression through sequence-specific mRNA targeting, and genome-wide RNAi screens produce genome-wide loss-of-function phenotypes.[11] This allows for a system-level understanding of the host cellular processes and comprehensive identification of molecular components underlying influenza pathogenicity. The lentiviral-based Decode™ RNAi library (Open Biosystems), consisting of 7 pools, each with ~10,000 shRNAmir constructs, was used to establish stably transduced genome-wide knockdown of every host gene in human lung adenocarcinoma A549 cells (FIG. 2). Cells were transduced at an MOI of 0.3, which allowed 100-fold coverage of each clone and reduced the risk of any single cell being multiply transduced to less than 4% of the cell population. The transduced cells were then infected with influenza virus strain A/New York/55/2004(H3N2) (NY55) at an MOI of 7 PFU/cell to ensure >99% of cells were initially infected (FIG. 2). Illumina®-mediated high throughput sequencing of all 7 pools was then individually performed on two independent biological replicate screens of surviving transduced, infected cells. The combined high throughput genome-wide screens identified more than 1000 potential targets (FIG. 3). 35 genes were identified in both trials (FIG. 3), knockdown of which provided protection against influenza A/NY/55/2005 infection. Many of these genes' ontological functions are shown in FIG. 4-6 and discussed below. Of the 35 genes found in both high-throughput screens (FIG. 3), 4 genes—BAD, INFSF12-TNFSF13/TNFSF13, MX2, and USP47—appeared at 100- to 1000-fold higher frequencies during Illumina® high-throughput sequencing than did most of the other genes (Table 8). BAD, TNFSF12-TNFSF13/INFSF13, MX2, and USP47 genes were also identified in a preliminary manual screen of 2 library pools in which transduced cell clones that survived NY55 infection were individually isolated, amplified (which demonstrated each survived long-term transduction and infection), and sequenced to identify the shRNA insert.

TABLE 8-A Genes detected in both high-throughput genomic screens

| Gene | # Trials | # Pools | Oligo ID | Sense Sequence | SEQ ID NO | Description | Count |
|---|---|---|---|---|---|---|---|
| BAD | 2 | 4 | V2HS_243025 | CAGTGACCTTCGCTCCACA | 2 | BCL2-associated agonist of | 343116 |
| | | | V2HS_201511 | GAGTTTGTGGACTCCTTTA | 3 | cell death | 31 |
| | | | V2HS_262043 | GACTTGGACTTGGATGTAA | 5 | | 31 |
| | | | V2HS_15289 | CTCACTACCAAATGTTAAT | 1 | | 30 |
| | | | V2HS_202976 | GTGCTCACTACCAAATGTT | 4 | | 1 |
| MX2 | 2 | 1 | V2HS_152031 | GACAAGATGTTCTTTCTAA | 25 | Myxovirus (influenza virus) resistance 2 | 16774 |
| TNFSF12-TNFSF13, TNFSF13 | 2 | 5 | V2HS_17314 | GATATTCTGAGTGTCATAA | 12 | Tumor necrosis factor (ligand) | 766 |
| | | | V2HS_17318 | CTCCAGAGATGTAGCTATT | 15 | superfamily, member 13; | 306 |
| | | | V2HS_17313 | GCCGCCCTCTGCTAGGGAA | 11 | TNFST12-TNFSF-13 | 164 |
| | | | V2HS_17317 | GAGACTCTATTCCGATGTA | 14 | readthrough transcript | 86 |
| | | | V2HS_17316 | GGTGCCTTCGCAGTCAAAT | 13 | | 75 |

| Gene | | | Clone ID | Sequence | SEQ ID | Description | Value |
|---|---|---|---|---|---|---|---|
| USP47 | 2 | 6 | V2HS_174637 | GAATCTGTCTTGAAACCAA | 31 | Ubiquitin specific peptidase 47 | 1110 |
| | | | V2HS_174640 | CTTATAAGATGATGGATTT | 40 | | 269 |
| | | | V2HS_174642 | GATTTAGACTGGAATCCTA | 34 | | 59 |
| | | | V2HS_218228 | CAATGACTTGCTATTTGAA | 35 | | 39 |
| | | | V2HS_174641 | GGATTCCTTTGGATGATAT | 33 | | 10 |
| | | | V2HS_174639 | CGCAATACATGCAAGATAA | 32 | | 5 |
| MX1 | 2 | 2 | V2HS_152026 | CTCATCACACATATCTGTA | 41 | Myxovirus (influenza virus) resistance 1, interferon-inducible protein p78 | 1952 |
| | | | V2HS_152028 | CTGCCAGGCTTTGTGAATT | 42 | | 178 |
| MALT1 | 2 | 1 | V2HS_84222 | CCAATATTGTGTTTGGATA | 43 | Mucosa associated lymphoid tissue lymphoma translocation gene 1 | 323 |
| RPS25 (LOC100131196) | 2 | 1 | V2HS_93855 | CTTAGTAAAGGACTTATCA | 44 | Ribosomal protein S25; similar to hCG1640659 | 173 |
| SH3BP4 | 2 | 1 | V2HS_260346 | CTTTCTATTTGTTAAGTAT | 45 | SH3-domain binding protein 4 | 99 |
| hCG1986447 | 2 | 1 | V2HS_29650 | GTGCTTTATTCAAATCTAA | 47 | HCG1986447 | 40 |
| WNK2 | 2 | 1 | V2HS_238923 | GTCTGAGAGAGTGACCTAT | 48 | WNK lysine deficient protein kinase 2 | 33 |
| TMC6 | 2 | 1 | V2HS_198493 | GGGACTCTATTTATTCTGA | 49 | Transmembrane channel-like 6 | 24 |
| CFL1 | 2 | 1 | V2HS_64314 | CCCTCTATGATGCAACCTA | 50 | Cofilin 1 (non-muscle) | 8 |
| ABI2 | 2 | 1 | V2HS_196634 | ACCAGTTCGTTATATTAGA | 51 | Abl interactor 2 | 3 |
| ARRDC3 | 2 | 1 | V2HS_217697 | GGCCTTGGCTACTACCAGT | 52 | Arrestin domain containing 3 | 2 |
| BRCA1 | 2 | 3 | V2HS_254648 | CACAAAGTGTGACCACATA | 53 | Breast cancer 1, early onset | 1 |
| | | | V2HS_280394 | GATCGATTATGTGACTTAA | 54 | | 1 |
| | | | V2HS_255064 | CCCTTTCACCCATACACAT | 55 | | 1 |
| C17orf85 | 2 | 1 | V2HS_176062 | CCGATACTCGGGAGAAGAA | 56 | Chromosome 17 open reading frame 85 | 2 |
| C1orf71 | 2 | 1 | V2HS_44617 | CGGAGGAACTCTGTTAGAA | 57 | Chromosome 1, open reading frame 71 | 2 |
| C6orf162 | 2 | 1 | V2HS_35766 | GTGTTCTTATAGTTATTTA | 58 | Chromosome 6, open reading frame 62 | 2 |
| CCNJL | 2 | 1 | V2HS_136349 | CTCAGCACGTGTATTGAAA | 59 | Cyclin J-like | 2 |
| GON4L | 2 | 1 | V2HS_138350 | CAGGTGAGAGCTGGAGAAT | 60 | Gon-4-like (*C. elegans*) | 2 |
| HIST1H2AB | 2 | 1 | V2HS_33954 | CATCATAAGGCCAAGGGAA | 61 | Histone cluster 1, H2ab | 2 |
| HPS4 | 2 | 1 | V2HS_70495 | GCCTATCCGTGTATATGGA | 62 | Hermansky-Pudlak syndrome 4 | 2 |
| LHX8 | 2 | 1 | V2HS_75780 | ACCATTCTGAGTTTATTAA | 63 | LIM homeobox 8 | 2 |
| RPL23 (LOC646949) | 2 | 1 | V2HS_23046 | GGACCAGTAGCAAAGGAGT | 64 | Ribosomal proein L23; hypothetical LOC646949 | 2 |
| RPL32 (LOC728572) | 2 | 1 | V2HS_165267 | CTGAGATTGCTCACAATGT | 65 | Similar to rCG33193 | 2 |
| LOC730139 | 2 | 1 | V2HS_25169 | GGATGTAAGTGTTACATCT | 67 | Hypothetical protein LOC730139 | 1 |
| | | | V2HS_25168 | GTGTACACATGCTGACACA | 68 | | 1 |
| LRRC39 | 2 | 2 | V2HS_18852 | GAATTATTTGGCCTTCAGT | 69 | Leucine rich repeat containing 39 | 2 |
| | | | V2HS_18851 | ACCTTGATCTGAGTATGAA | 70 | | 1 |
| NRG1 | 2 | 1 | V2HS_84939 | ATGTGTTATTTGTCACAAA | 71 | Neuregulin 1 | 2 |
| OR52A1 | 2 | 2 | V2HS_244561 | GCTAGGTTTAAAGCATTCA | 72 | Olfactory receptor, family 52, subfamily A, member 1 | 1 |
| | | | V2HS_49243 | CTTGGAATATTCTGGTTTA | 73 | | 1 |
| PLEKHH1 | 2 | 1 | V2HS_46786 | CTCTGGATTTAGAGATATA | 74 | Pleckshin homology domain containing, family H (with MyTH4 domain) member 1 | 2 |

-continued

| Gene | # Trials | # Pools | Oligo ID | Sense Sequence | | Description | Count |
|------|----------|---------|----------|----------------|---|-------------|-------|
| PTPN13 | 2 | 1 | V2HS_57273 | CAGTGAAAGTCCATCTATT | 75 | Protein tyrosine phosphatase, non-receptor type 13 (APO-1/CD95 (Fas)-associated phosphatase) | 4 |
| PTPRJ | 2 | 2 | V2HS_91546 | CTAATTGACTCCACTGGAT | 76 | Protein tyrosine phosphatase, receptor type, J | 1 |
| | | | V2HS_171000 | GGAAGTCACGTATTTGAAT | 77 | | 1 |
| RLN1 | 2 | 1 | V2HS_94799 | CAATCTTAGCTTTGAAGAA | 78 | Relaxin 1 | 2 |
| RNF19A | 2 | 1 | V2HS_96523 | GTTCTTCATCCATTAGTTA | 79 | Ring finger protein 19A | 2 |
| SLC7A14 | 2 | 1 | V2HS_57109 | GTGTTGACAATATATTGAT | 80 | Solute carrier family 7 (cationic amino add transporter, y + system), member 14 | 3 |
| ST8SIA3 | 2 | 2 | V2HS_114878 | CTGAGCACAGGTATTCTTA | 81 | ST8 alpha-N-acetyl-neuramide alpha-2,8-sialyltransferase 3 | 1 |
| | | | V2HS_114879 | GGAAGATCTTCCATACCAT | 82 | | 1 |
| STX3 | 2 | 1 | V2HS_33937 | CCCAGAAACTGCAATGTAT | 83 | Syntaxin 3 | 3 |
| TMTC4 | 2 | 2 | V2HS_177667 | CTTTATTCCTCAAGGCAAT | 84 | Transmembrane and tetratricopeptide repeat containing 4 | 1 |
| | | | V2HS_275500 | CATGAATAATCTTGGAAAT | 85 | | 1 |
| TTN | 2 | 1 | V2HS_171633 | GTTCCCGACTTGAAATGAA | 86 | Titin | 1 |
| | | | V2HS_171637 | CCATCTCGGTTCTTTAGAA | 87 | | 1 |
| UBXN7 | 2 | 2 | V2HS_130208 | CATTATTTGGTGCTCCTAA | 88 | UBX domain protein 7 | 1 |
| YPEL2 | 2 | 2 | V2HS_77698 | CTCTTTAACTCAGTAGTTA | 89 | Yippee-like 2 (*Drosophila*) | 1 |
| | | | V2HS_77701 | CAAGGACGAGCATACCTCT | 90 | | 1 |
| ZNF251 | 2 | 1 | V2HS_250202 | GACCAAGAAGGAACTATCT | 91 | Zinc finger protein 251 | 1 |
| | | | V2HS_215547 | AATATTACTGGCAAAGTAA | 92 | | 1 |

Count: number of times indicated sequence was detected by Illumina® high-throughput sequencing.
Sequences identified >7 times are arranged by decreasing count at top of table;
all sequences identified <7 times are arranged alphabetically.

Table 8-B Genes detected in a single high-throughput genomic screen but at high frequency

| Gene | # Trials | # Pools | Oligo ID | Sense Sequence | | Description | Count |
|------|----------|---------|----------|----------------|---|-------------|-------|
| MERTK | 1 | 3 | V2HS_1643 | CTGCATACTTACTTACTTT | 93 | c-mer proto-oncogene tyrosine kinase | 1178 |
| | | | V2HS_168768 | CAGACGTTATTTACCGTCA | 94 | | 460 |
| | | | V2HS_197158 | CCTTCAGTGATCCAGTGAA | 95 | | 371 |
| SCG2 | 1 | 3 | V2HS_172404 | GCCAGGATGCTAGTTAAAT | 96 | Secretogranin II (chromogranin C) | 19 |
| | | | V2HS_172401 | CTCTTGATTCTCAGTCTAT | 97 | | 3 |
| | | | V2HS_172400 | CTCCTATGTATGAAGAGAA | 98 | | 2 |

EXAMPLE 2

Target Host Factor Validation

Figure 7:
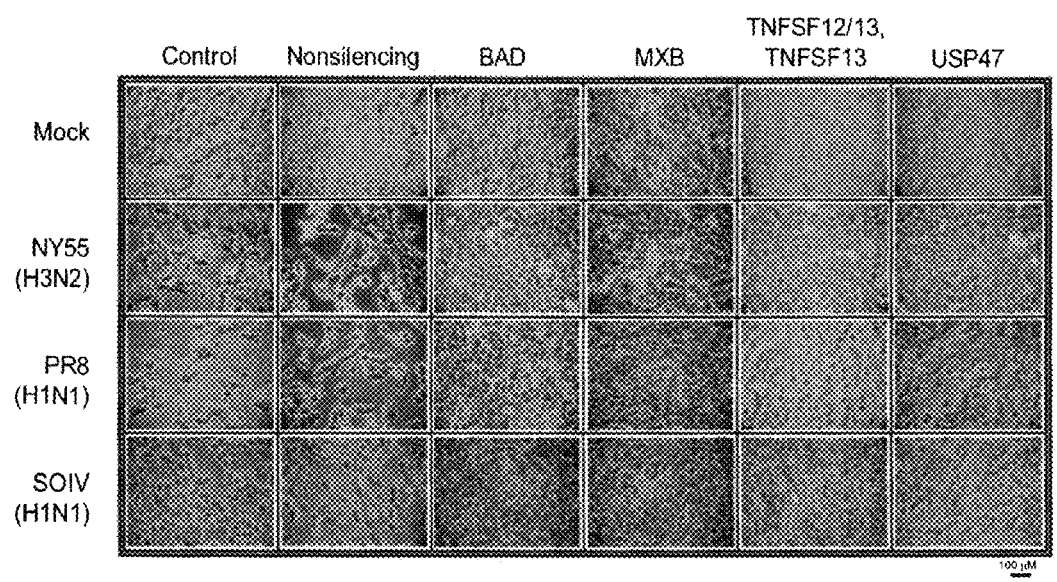
FIG. 7 shows Influenza virus replication in A549 knockdown cells. Cytopathic effect (CPE) of cells knocked down with one of indicated shRNA, mock infected (top row), or infected with NY55 (48 hpi after MOI 1—2nd row), PR8 (72 hpi after MOI 0.1—3rd row), or SOIV (72 hpi after MOI 0.1—bottom row). Cells were examined with a Nikon Eclipse TE2000-S inverted microscope and images obtained with a Canon PowerShot A700 digital camera.
Figure 8A:
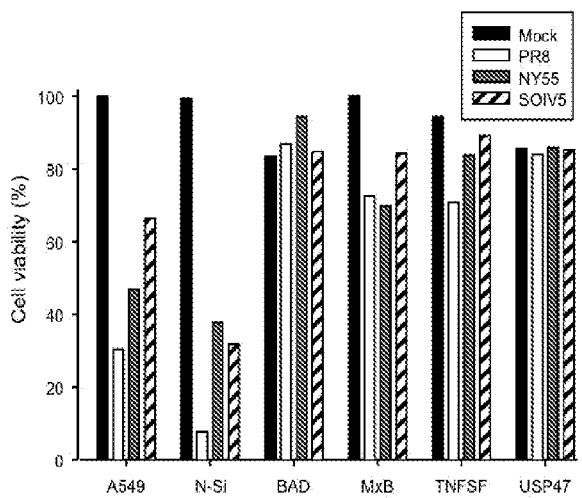
FIG. 8 shows (a) Measurements of cell viability (measured by trypan blue exclusion) of normal A549 and A549 knockdown cells at 72 hpi after mock infection or infection with PR8, NY55 and SOIV virus; (b) Measurements of NY55 (48 hpi), PR8 (72 hpi), and SOIV (72 hpi) replication in shRNA knockdown A549 cells at MOI 1, 0.01, and 0.5, respectively. Additional data presented in FIG. 9; (c) NY55 and SOIV virus replication in siRNA-knockdown A549 cells after 48 h infection at MOI 0.1. NSi=non-silencing. Error bars represent standard deviation from 2-3 biological replicates.
Figure 8B:
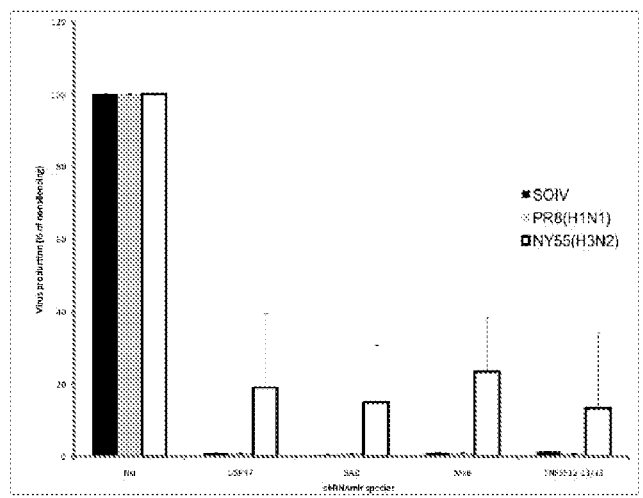

As an initial confirmation that BAD, TNFSF12-TNFSF13/TNFSF13, MX2, and USP47 knockdown eliminate influenza virus-mediated cytotoxicity, sets of A549 cells were individually transduced with shRNA-lentiviruses specifically targeting each transcript. The shRNA constructs contained puromycin markers for positive selection of transduced cells. Stably transduced cells were passaged in puromycin at least twice to remove non-transduced cells, followed by infection with various influenza A viruses. Non-transduced cells, as well as cells transduced with an irrelevant non-silencing shRNA, were killed after being infected with NY55 at an MOI of 1. In contrast, there was no observable cytopathic effect (CPE) in influenza virus infected cells that had been transduced with BAD-, TNFSF12-TNFSF13/TNFSF13-, MX2-, or USP47-specific shRNAs (FIG. 7). Knockdown of these genes also resulted in significant reductions in virus titer compared to non-transduced and non-silencing transduction, with virus titers being generally reduced to about 20% of control levels (FIG. 8b). The shRNA constructs that target TNFSF13 mRNA also inhibits TNFSF12-13 mRNA. WST-1 cell viability assay (Roche) showed no significant reduction in knockdown cell viability compared to controls (FIG. 9a).

Figure 8C:
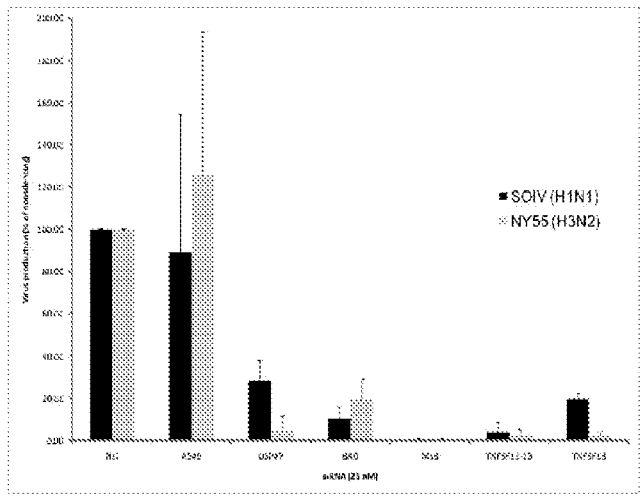
Figure 11:
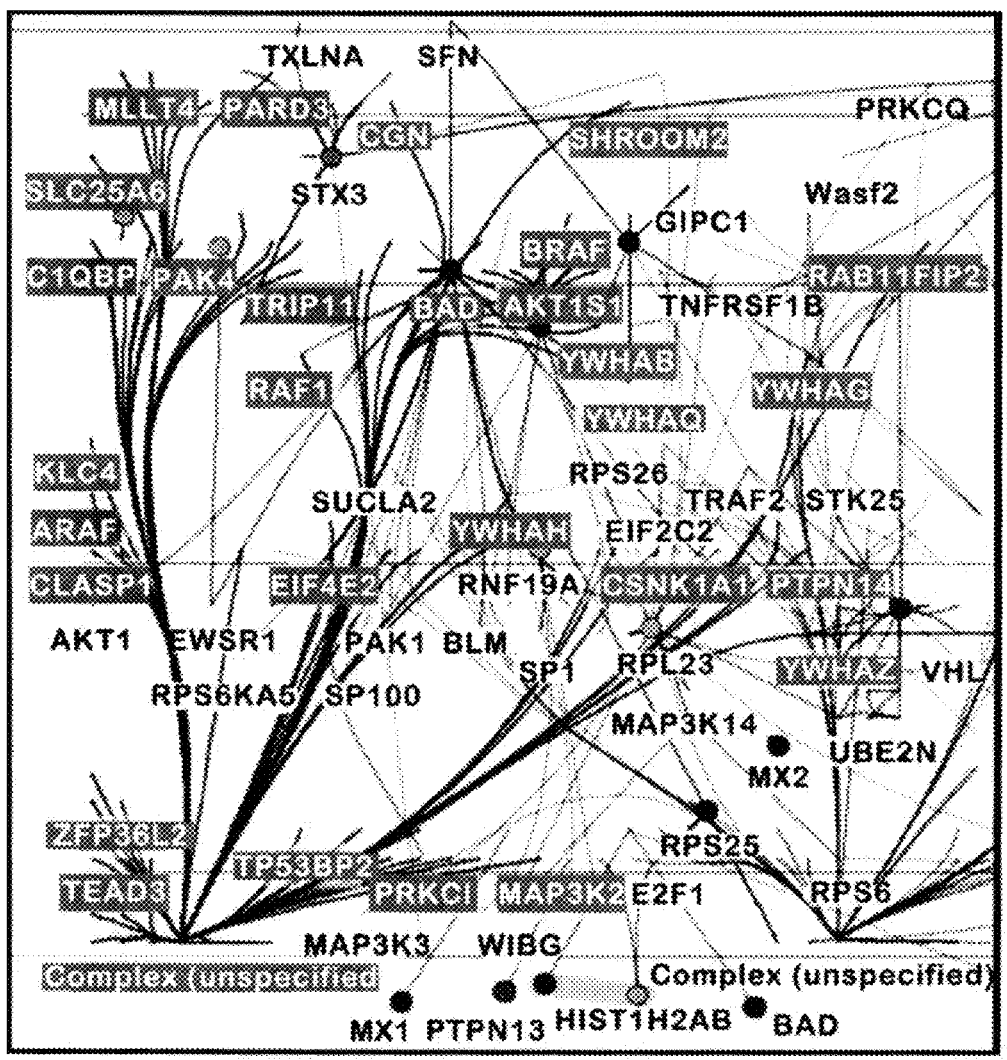
FIG. 11 shows an analysis of critical nodes within the interaction network of the 31 identified genes, with focus on three unspecified protein complexes.
Figure 12:
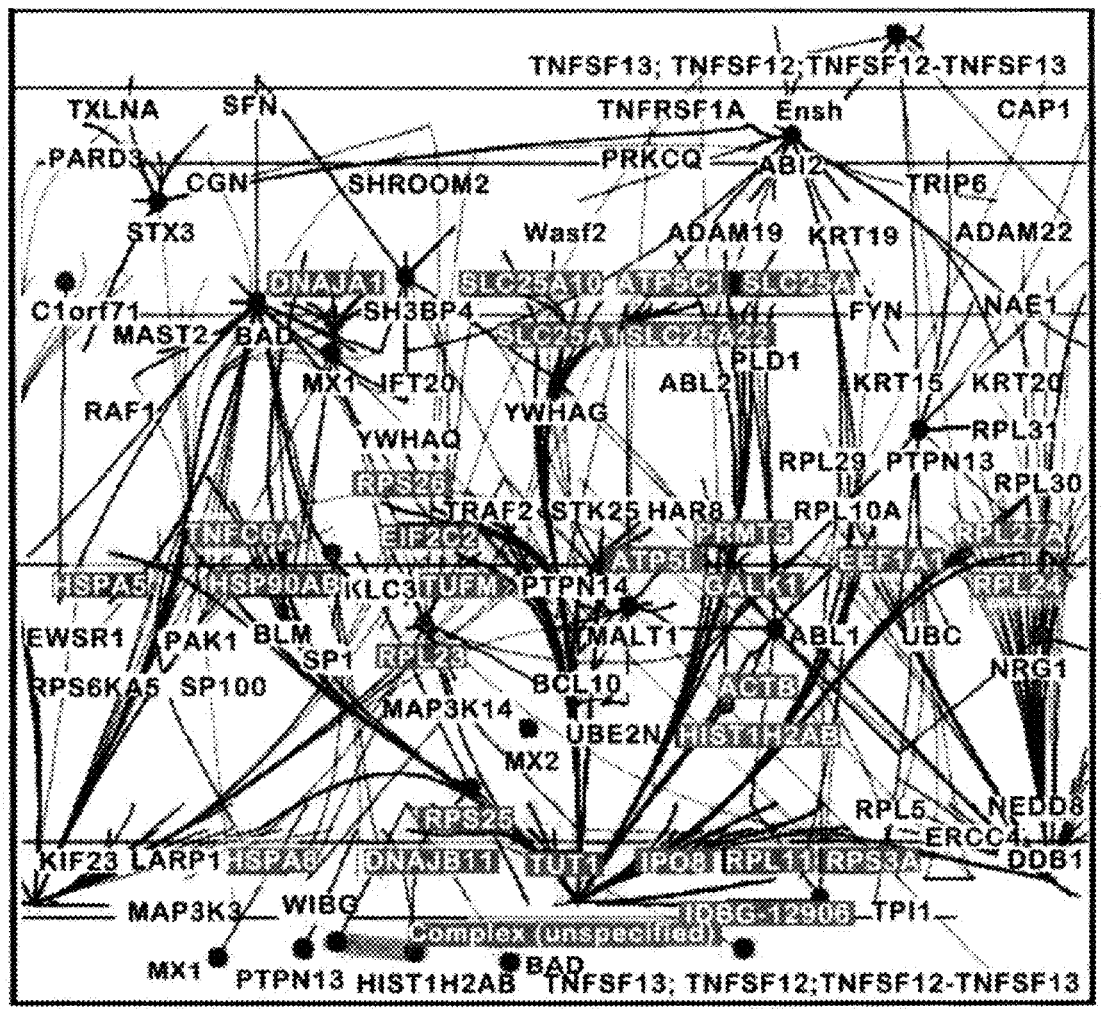
FIG. 12 shows an analysis of critical nodes within the interaction network of the 31 identified genes, with focus on BAD. Critical nodes are shown in black circle and the direct interacting protein partners of these critical nodes (gene product) are shown in highlighted boxes.
Figure 13:
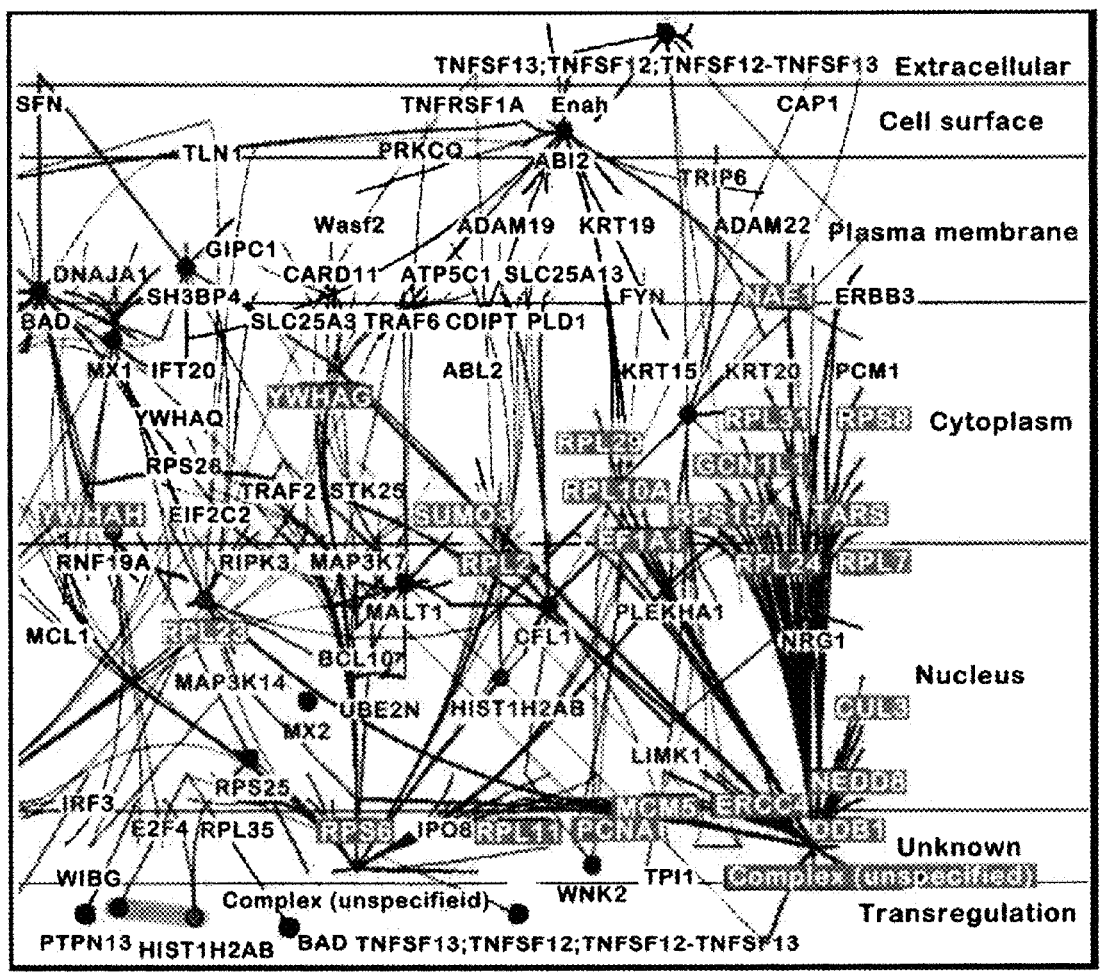
FIG. 13 shows an analysis of critical nodes within the interaction network of the 31 identified genes, with focus on TNFSF12-13/TNFSF13. Critical nodes shown in black circle and the direct interacting protein partners of these critical nodes (gene product) are shown in highlighted boxes.

As further validation, to ensure that lack of cytotoxicity and reduced virus replication were not caused by off-target effects or other artifacts, protein knockdowns were repeated with siRNA duplexes (Dharmacon®). Sets of A549 cells were treated with each of four distinct siRNAs that target each of the four proteins (plus an irrelevant non-silencing control) twice, 24 h apart, and after a further 24 h, were infected with influenza virus. Influenza virus replication was dramatically reduced by each of the four BAD-, TNFSF12-TNFSF13/TNFSF13-, MX2-, and USP47-specific siRNAs (FIG. 8c; and FIG. 10) and no detectable CPE was observed.

Since NY55 is an H3N2 virus (like the 1968 pandemic "Hong Kong" virus), it was then determined whether these observations could be extended more broadly to other influenza virus subtypes. Therefore, the effects of knocking down these genes were examined on cytopathology and replication of the A/Puerto Rico/8/1934 (H1N1) (PR8) and contemporary pandemic SOIV H1N1 isolates. Similar to effects observed with NY55, knockdown of BAD, TNFSF12-TNFSF13/TNFSF13, MX2, and USP47 also protected the host cell from virus-induced cytopathology during PR8 (H1N1) and SOIV (H1N1) infections (FIG. 7*a*) and resulted in reduced virus replication (FIG. 8*b,c*). These data strongly indicate that MX2, BAD, TNFSF12-13, TNFSF13, and USP47 knockdown protect human lung epithelial A549 cells from virus-mediated cytotoxicity during infection by viruses of multiple H and N types. Thus, different influenza virus subtypes require certain common cellular pathways for replication and the roles played by BAD, TNFSF12-TNFSF13/TNFSF13, MX2, and USP47 are virus-type independent. Each of these 4 genes (BAD, TNFSF12-TNFSF13/TNFSF13, MX2, and USP47), and many of the other 31 consistently identified genes, participate in integrated cellular pathways with broad biological impact, including host defence, autoimmunity, cancer and cell cycle, and inflammation. For example, BAD is a pro-apoptotic protein that belongs to the BH3-only subfamily. In light of the pro-apoptotic nature of BAD, a reduction in viral replication seen here suggests a synergistic role of BAD in the virus' lifecycle by sequestering Bcl-2 and promoting apoptosis.

TNFSF13 and the fusion protein TNFSF12-13—also known as APRIL and TWE-PRIL, respectively—belong to the tumour necrosis factor (TNF) ligand superfamily.[12,13] Influenza virus infection up-regulates TNFSF13 expression in lung tissues and affects recruitment of macrophages to the site of infection in TNFSF13 deficient mice.[14] Human MX2 protein has no anti-influenza virus activity described to date; however, it localizes to the nuclear membrane where it may play a role in nucleocytoplasmic trafficking.[15,16,17,18] USP47 is a deubiquitinase, whose specific role in cellular processes remains relatively unknown.[19] Although there are previous reports indicating the importance of the ubiquitin-proteasome pathway in other viruses, the involvement of deubiquitylation in influenza remains relatively unknown. More studies on the cellular functions and their involvement in influenza infection are warranted to delineate the specific molecular mechanisms to which TNFSF12-13, TNFSF13 and USP47 proteins contribute.

In order to delineate host biomolecular interactions that may function in conferring protection against viral infection, network analysis[20,21] was performed. The genes identified in this study participated in 175 binary interactions and three regulatory protein complexes (FIG. 6, Table 9 and FIG. 11-13). Network analysis highlighted the role of BAD and TNFSF12-13/TNFSF13 as being critical nodes within the pathways (FIG. 12), and predicted the involvement of NF-κB, MAPK and AKT pathways in host processes that confer host cell survival.

Knockdown of host MX2, BAD, TNFSF12-13, TNFSF13, or USP47 genes confers broad, non-lethal and long-lasting virus type-independent protection against influenza virus-mediated cytotoxicity and promotes host cell survival.

EXAMPLE 3

Target Host Factors

Cytopathology induced during influenza infection is a contributing factor to tissue damage and has been suggested to be a catalyst for aberrant host immune response during disease progression, but the underlying molecular mechanisms remain obscure.

BAD is a pro-apoptotic protein that belongs to the BH3-only subfamily. Its interaction with Bcl-2 and Bcl-$X_L$ inhibits the function of these two anti-apoptotic molecules to promote apoptosis.[1,2] In West Nile virus (WNV)[3,4], the human immunodeficiency virus (HIV)[5,6], and Hepatitis B and C viruses[7], viral-induction of apoptosis are significant contributing factors to disease pathology. It also has been recently reported that influenza viruses initiate and require cellular apoptosis for efficient virus replication, and that the anti-apoptotic Bcl-2 protein negatively effects influenza virus replication.[8,9,10] Similarly, a study with the 1918 pandemic virus in macaques indicate up-regulation of cell death and inflammatory related genes[11]. Without whishing to be bound by theory the results suggest a synergistic role of BAD in the virus' lifecycle by sequestering Bcl-2 and promoting apoptosis.

TNFSF13 and the fusion protein TNFSF12-13 belong to the tumour necrosis factor (TNF) ligand superfamily.[12,13] Intergenic splicing between exon 6 of TNFSF12, another member of the TNF superfamily, and exon 2 of TNFSF13 leads to the production of a fusion protein called TNFSF12-13, which displays the same receptor specificity as TNFSF13.[12] TNFSF13 and TNFSF12-13 are reported to induce cellular proliferation and be involved in innate and adaptive immune responses.[14] TNFSF13 is a proliferation inducing ligand located in the cytosol and reportedly involved in class switch recombination in B cell responses.[15] Influenza virus infection has been shown to upregulate TNFSF13 expression in lung tissues and affect recruitment of macrophages to the site of infection in TNFSF13 deficient mice.[16]

Human MX2 protein has no anti-influenza virus activity described to date; however, it localizes to the nuclear membrane where it may play a role in nucleocytoplasmic trafficking.[17,18,19] Without whishing to be bound by theory the results suggest that MX2 has a role in trafficking specific viral proteins or protein complexes between the cytoplasm and the nucleus.[20,21]

USP47 is a deubiquitinase, whose specific role in cellular processes remains relatively unknown.[22] Recently, USP47 has been reported to play a function in scattering responses in epithelial cells.[23] Although there are previous reports indicating the importance of the ubiquitin-proteasome pathway in other viruses, the involvement of deubiquitylation in influenza remains relatively unknown.

31 of the 35 gene candidates identified in the Illumina® screen (4 genes had no known functions) were used for bioinformatics interrogation in order to identify host biomolecular interactions that these candidates participated in employing a open source interaction database analysis platform[24,25]. Computational network analysis demonstrated that several members of the two regulatory pathways Nuclear factor (NF)-κB and the mitogen activated protein kinase (MAPK) pathways were direct interactors of the identified gene candidates. For example, (i) the gene product of MALT-1 interacts with IκBκG (NF-κB essential modulator, NEMO), TRAF-6 (regulator of TLRNF-κB pathway), MAP3K and MAKP9, and TNFAIP3 (a negative regulator of NF-κB), (ii) RPL23 and PTPNI3 directly interacts with NF-κBIA (a regulator of NF-κB), (iii) RPL23 participated in direct interactions with members of the MAPK pathway and TRAF-2 (TRAF-2 is required for the activation of both MAPK/JNK and NF-κB pathways), (iv) Members of MAPK family and AKT, known to phosphorylate NF-κB subunits[26] were demonstrated to be direct to interacting protein partner with BAD, (v) 14-3-3 family of proteins, known to be involved in protection against viral infections[27], including in AKT signalling pathway[28], were found to be direct interacting partners for four of the 31 candidates, BAD, SH3BP4, CFL1 and RPL23 (Table 9). (vi) TNFSF-12-13 (TWE-PRIL) a critical node in the analyses was previously demonstrated to be involved in stimulating lymphocyte proliferation. Further, the 31 identified gene candidates were analyzed for the overrepresentation of transcription factor binding sites. Over represented transcription factors (TFs) were defined if the binding sites for the factors were predicted in the promoter region of at least three of the candidate genes. This analysis revealed 36 transcription factor binding sites to be enriched within the promoter regions of the submitted genes, among which several TFs were known to be active in host responses downstream of the NF-κB and MAPK pathways. Over represented TFs such as MEF2A, AIRE, SRF, CREB1 and IRF1, all are known to be involved in host responses against pathogenic infections, including viral infections[29,30,31,32,33,34]. This analysis was consistent with the interaction network analysis which also demonstrated the involvement of both NF-κB and MAPK pathways in the activity of the identified candidates. The human genome-wide screen identified genes that play significant roles in protecting host cells from virus-induced cytopathic effect, and also are important in influenza propagation.

TABLE 9

Immunity-related interacting protein partners of the identified target polypeptides.

| Unique Identifier | Gene Name | Log (Sum of Frequency) | Interaction Level | Interaction | Interactor Species | PMID |
|---|---|---|---|---|---|---|
| NM_004322 | BAD | 5.5 | Direct interaction | Transcription factor HNF4A binds with BAD gene | Homo sapiens | 14988562 |
| NM_004322 | BAD | 5.5 | Direct interaction | Phosphorylation of BAD by RAF1 | Homo sapiens | 15849194 |
| NM_004322 | BAD | 5.5 | Direct interaction | Phosphorylation of BAD by PAK1 | Homo sapiens | 10611223 |
| NM_004322 | BAD | 5.5 | Direct interaction | Phosphorylation of BAD by AKT1 | Homo sapiens | 15998799 |
| NM_004322 | BAD | 5.5 | Direct interaction | BAD interacts with YWHAZ | Homo sapiens | 11410287 |
| NM_004322 | BAD | 5.5 | Direct interaction | BAD interacts with YWHAQ | Homo sapiens | 9369453\|15694340 |
| NM_004322 | BAD | 5.5 | Direct interaction | BAD interacts with TMBIM6 | Homo sapiens | 9660918 |
| NM_004322 | BAD | 5.5 | Direct interaction | BAD interacts with SNCA | Homo sapiens | 11742726 |
| NM_004322 | BAD | 5.5 | Direct interaction | BAD interacts with S100A10, YWHAB, YWHAH, YWHAE | Homo sapiens | 9369453 |
| NM_004322 | BAD | 5.5 | Direct interaction | BAD interacts with RPS6KA5, PRKACA, RPS6KA1 | Homo sapiens | 11500364 |
| NM_004322 | BAD | 5.5 | Direct interaction | BAD interacts with PRKCI | Homo sapiens | 15705582 |
| NM_004322 | BAD | 5.5 | Direct interaction | BAD interacts with PPP1CA | Homo sapiens | 17274640 |
| NM_004322 | BAD | 5.5 | Direct interaction | BAD interacts with PIM2 | Homo sapiens | 12954615 |
| NM_004322 | BAD | 5.5 | Direct interaction | BAD interacts with MCL1 | Homo sapiens | 11483855\|15694340 |
| NM_004322 | BAD | 5.5 | Direct interaction | BAD interacts with GRB2 | Homo sapiens | 17474147 |
| NM_004322 | BAD | 5.5 | Direct interaction | BAD interacts with EWSR1, SFN | Homo sapiens | 16189514 |
| NM_004322 | BAD | 5.5 | Direct interaction | BAD interacts with BCL2L2 | Homo sapiens | 11483855\|15694340\|10381646\|12115603 |
| NM_004322 | BAD | 5.5 | Direct interaction | BAD interacts with BCL2L1 | Homo sapiens | 14681455\|15705582\|11494146\|7834748\|9389483\|9305851\|11206074\|10620799\|15694340\|12137781\|12115603\|9824152\|11077446 |
| NM_004322 | BAD | 5.5 | Direct interaction | BAD interacts with BCL2A1 | Homo sapiens | 15694340\|11483855 |
| NM_004322 | BAD | 5.5 | Direct interaction | BAD interacts with BCL2 | Homo sapiens | 9388232\|9463381 |
| NM_004322 | BAD | 5.5 | Direct interaction | BAD and Gimap5, Gimap3 | Mus musculus/ Homo sapiens | 16509771 |
| NM_004322 | BAD | 5.5 | Direct interaction | BAD and BNIP3L | Homo sapiens | 9973195 |
| NM_002463 | MX2 | 4.2 | Direct interaction | MX2 interacts with MX2 | Homo sapiens | 9405443 |
| NM_002462 | MX1 | 3.3 | Direct interaction | Transcription factor IRF3 binds with MX1 gene | Homo sapiens | 17494065 |
| NM_002462 | MX1 | 3.3 | Direct interaction | MX1 interacts with TRPC7 | Homo sapiens | 15757897 |
| NM_002462 | MX1 | 3.3 | Direct interaction | MX1 interacts with TRPC6 | Homo sapiens | 15757897 |

TABLE 9-continued

Immunity-related interacting protein partners of the identified target polypeptides.

| Unique Identifier | Gene Name | Log (Sum of Frequency) | Interaction Level | Interaction | Interactor Species | PMID |
|---|---|---|---|---|---|---|
| NM_002462 | MX1 | 3.3 | Direct interaction | MX1 interacts with TRPC5 | Homo sapiens | 15757897 |
| NM_002462 | MX1 | 3.3 | Direct interaction | MX1 interacts with TRPC4 | Homo sapiens | 15757897 |
| NM_002462 | MX1 | 3.3 | Direct interaction | MX1 interacts with TRPC3 | Homo sapiens | 15757897 |
| NM_002462 | MX1 | 3.3 | Direct interaction | MX1 interacts with TRPC1 | Homo sapiens | 15757897 |
| NM_002462 | MX1 | 3.3 | Direct interaction | MX1 interacts with SUMO1 | Homo sapiens | 11716541 |
| NM_002462 | MX1 | 3.3 | Direct interaction | MX1 interacts with SP100 | Homo sapiens | 11716541 |
| NM_002462 | MX1 | 3.3 | Direct interaction | MX1 interacts with PIAS1 | Homo sapiens | 11716541 |
| NM_002462 | MX1 | 3.3 | Direct interaction | FANCA interacts with MX1 | Homo sapiens | 14499622 |
| NM_002462 | MX1 | 3.3 | Direct interaction | DAXX interacts with MX1 | Homo sapiens | 11716541 |
| NM_002462 | MX1 | 3.3 | Direct interaction | BLM interacts with MX1 | Homo sapiens | 11716541 |
| NM_003808 | TNFSF13; TNFSF12; TNFSF12-TNFSF13 | 3.1 | Direct interaction | Transcription factor HNF4A binds with TNFSF13; TNFSF12; TNFSF12-TNFSF13 gene | Homo sapiens | 14988562 |
| NM_003808 | TNFSF13; TNFSF12; TNFSF12-TNFSF13 | 3.1 | Direct interaction | TNFSF13; TNFSF12; TNFSF12-TNFSF13 interacts with TNFSF13; TNFSF12; TNFSF12-TNFSF13 | Homo sapiens | 12370363 |
| NM_003808 | TNFSF13; TNFSF12; TNFSF12-TNFSF13 | 3.1 | Direct interaction | TNFSF13; TNFSF12; TNFSF12-TNFSF13 interacts with XPO1 | Homo sapiens | 11565755 |
| NM_003808 | TNFSF13; TNFSF12; TNFSF12-TNFSF13 | 3.1 | Direct interaction | TNFSF13; TNFSF12; TNFSF12-TNFSF13 interacts with TNFSF13B | Homo sapiens | 12370363 |
| NM_003808 | TNFSF13; TNFSF12; TNFSF12-TNFSF13 | 3.1 | Direct interaction | TNFRSF1A interacts with TNFSF13; TNFSF12; TNFSF12-TNFSF13 | Homo sapiens | 10706119 |
| NM_003808 | TNFSF13; TNFSF12; TNFSF12-TNFSF13 | 3.1 | Direct interaction | TNFRSF14 interacts with TNFSF13; TNFSF12; TNFSF12-TNFSF13 | Homo sapiens | 10706119 |
| NM_003808 | TNFSF13; TNFSF12; TNFSF12-TNFSF13 | 3.1 | Direct interaction | TNFRSF13B interacts with TNFSF13; TNFSF12; TNFSF12-TNFSF13 | Homo sapiens | 10956646 |
| NM_003808 | TNFSF13; TNFSF12; TNFSF12-TNFSF13 | 3.1 | Direct interaction | TNFRSF13B interacts with TNFSF13; TNFSF12; TNFSF12-TNFSF13 | Homo sapiens | 10956646 |
| NM_003808 | TNFSF13; TNFSF12; TNFSF12-TNFSF13 | 3.1 | Direct interaction | TNFRSF11B interacts with TNFSF13; TNFSF12; TNFSF12-TNFSF13 | Homo sapiens | 10706119 |
| NM_003808 | TNFSF13; TNFSF12; TNFSF12-TNFSF13 | 3.1 | Direct interaction | FAS interacts with TNFSF13; TNFSF12; TNFSF12-TNFSF13 | Homo sapiens | 10706119 |
| NM_003808 | TNFSF13; TNFSF12; TNFSF12-TNFSF13 | 3.1 | Direct interaction | AGGF1 interacts with TNFSF13; TNFSF12; TNFSF12-TNFSF13 | Homo sapiens | 14961121 |
| NM_006785 | MALT1 | 2.5 | Direct interaction | MALT1, MALT1, UBE2N, UBE2V2 (complex) | Homo sapiens | 14695475 |
| NM_006785 | MALT1 | 2.5 | Direct interaction | MALT1 physically interacts with TNFAIP3 | Homo sapiens | 18223652 |
| NM_006785 | MALT1 | 2.5 | Direct interaction | MALT1 interacts with VHL | Homo sapiens | 17353931 |
| NM_006785 | MALT1 | 2.5 | Direct interaction | MALT1 interacts with UBE2G2 | Homo sapiens | 17353931 |
| NM_006785 | MALT1 | 2.5 | Direct interaction | MALT1 interacts with UBB | Homo sapiens | 14695475 |
| NM_006785 | MALT1 | 2.5 | Direct interaction | MALT1 interacts with UBA52 | Homo sapiens | 17948050 |
| NM_006785 | MALT1 | 2.5 | Direct interaction | MALT1 interacts with TRAF6 | Homo sapiens | 17948050 |
| NM_006785 | MALT1 | 2.5 | Direct interaction | MALT1 interacts with TRAF6 | Homo sapiens | 15125833 |
| NM_006785 | MALT1 | 2.5 | Direct interaction | MALT1 interacts with TRAF2 | Homo sapiens | 15125833 |
| NM_006785 | MALT1 | 2.5 | Direct interaction | MALT1 interacts with SQSTM1 | Homo sapiens | 16874300 |

TABLE 9-continued

Immunity-related interacting protein partners of the identified target polypeptides.

| Unique Identifier | Gene Name | Log (Sum of Frequency) | Interaction Level | Interaction | Interactor Species | PMID |
|---|---|---|---|---|---|---|
| NM_006785 | MALT1 | 2.5 | Direct interaction | MALT1 interacts with PRKCQ | Homo sapiens | 17363905 |
| NM_006785 | MALT1 | 2.5 | Direct interaction | MALT1 interacts with MAP3K7IP2 | Homo sapiens | 17948050 |
| NM_006785 | MALT1 | 2.5 | Direct interaction | MALT1 interacts with MAP3K7 | Homo sapiens | 17948050 |
| NM_006785 | MALT1 | 2.5 | Direct interaction | MALT1 interacts with MALT1 | Homo sapiens | 14695475 |
| NM_006785 | MALT1 | 2.5 | Direct interaction | IKBKG, MALT1, UBE2N, UBE2V2 (complex) | Homo sapiens | 14695475 |
| NM_006785 | MALT1 | 2.5 | Direct interaction | IKBKG interacts with MALT1 | Homo sapiens | 17948050 |
| NM_006785 | MALT1 | 2.5 | Direct interaction | Cleavage reaction involving MALT1 and TNFAIP3 | Homo sapiens | 18223652 |
| NM_006785 | MALT1 | 2.5 | Direct interaction | CARD11 interacts with MALT1 | Homo sapiens | 17948050 |
| NM_006785 | MALT1 | 2.5 | Direct interaction | BCL10, MALT1, TRAF6 (complex) | Homo sapiens | 17948050 |
| NM_006785 | MALT1 | 2.5 | Direct interaction | BCL10, MALT1, MAPK9 (complex) | Homo sapiens | 17189706 |
| NM_006785 | MALT1 | 2.5 | Direct interaction | BCL10, CARD11, MALT1 (complex) | Homo sapiens | 17948050 |
| NM_006785 | MALT1 | 2.5 | Direct interaction | BCL10 interacts with MALT1 | Homo sapiens | 11090634\|14695475 |
| NM_006785 | MALT1 | 2.5 | Direct interaction | BCL10 interacts with MALT1 | Homo sapiens | 18223652\|11090634\|14695475 |
| NM_001028 | RPS25 | 2.2 | Direct interaction | Transcription factor HNF4A binds with RPS25 gene | Homo sapiens | 14988562 |
| NM_001028 | RPS25 | 2.2 | Direct interaction | RPS25 interacts with UPF2 | Homo sapiens | 15231747 |
| NM_001028 | RPS25 | 2.2 | Direct interaction | RPS25 interacts with SGSM2 | Homo sapiens | 16169070 |
| NM_001028 | RPS25 | 2.2 | Direct interaction | HAP1 interacts with RPS25 | Homo sapiens | 16169070 |
| NM_001028 | RPS25 | 2.2 | Direct interaction | CDC5L interacts with RPS25 | Homo sapiens | 11101529 |
| NM_014521 | SH3BP4 | 2 | Direct interaction | SH3BP4 interacts with YWHAZ | Homo sapiens | 15161933 |
| NM_014521 | SH3BP4 | 2 | Direct interaction | SH3BP4 interacts with YWHAQ | Homo sapiens | 17353931 |
| NM_014521 | SH3BP4 | 2 | Direct interaction | SH3BP4 interacts with YWHAG | Homo sapiens | 15324660\|17353931 |
| NM_014521 | SH3BP4 | 2 | Direct interaction | SH3BP4 interacts with YWHAB | Homo sapiens | 17353931 |
| NM_014521 | SH3BP4 | 2 | Direct interaction | SFN interacts with SH3BP4 | Homo sapiens | 15778465 |
| NM_014521 | SH3BP4 | 2 | Direct interaction | GIPC1 interacts with SH3BP4 | Homo sapiens | 17353931 |
| NM_014521 | SH3BP4 | 2 | Direct interaction | EPS15 interacts with SH3BP4 | Homo sapiens | 9303539 |
| NM_006648 | WNK2 | 1.5 | Direct interaction | FYN interacts with WNK2 | Homo sapiens | 17474147 |
| NM_006648 | WNK2 | 1.5 | Direct interaction | ATXN1 interacts with WNK2 | Homo sapiens | 16713569 |
| NM_006648 | WNK2 | 1.5 | Direct interaction | ABL1 interacts with WNK2 | Homo sapiens | 17474147 |
| NM_005507 | CFL1 | 0.9 | Direct interaction | Phosphorylation of CFL1 by LIMK1 | Homo sapiens | 17853892 |
| NM_005507 | CFL1 | 0.9 | Direct interaction | Colocalization of CFL1 and PLD1 | Homo sapiens | 17853892 |
| NM_005507 | CFL1 | 0.9 | Direct interaction | CFL1 interacts with YWHAZ | Homo sapiens | 15161933\|12361576 |
| NM_005507 | CFL1 | 0.9 | Direct interaction | CFL1 interacts with YWHAG | Homo sapiens | 15598710 |
| NM_005507 | CFL1 | 0.9 | Direct interaction | CFL1 interacts with TXNDC17 | Homo sapiens | 14607843 |
| NM_005507 | CFL1 | 0.9 | Direct interaction | CFL1 interacts with TPI1 | Homo sapiens | 12359716 |
| NM_005507 | CFL1 | 0.9 | Direct interaction | CFL1 interacts with TAGLN | Homo sapiens | 17353931 |
| NM_005507 | CFL1 | 0.9 | Direct interaction | CFL1 interacts with ROCK1 | Homo sapiens | 10436159 |
| NM_005507 | CFL1 | 0.9 | Direct interaction | CFL1 interacts with PLD2 | Homo sapiens | 17853892 |

TABLE 9-continued

Immunity-related interacting protein partners of the identified target polypeptides.

| Unique Identifier | Gene Name | Log (Sum of Frequency) | Interaction Level | Interaction | Interactor Species | PMID |
|---|---|---|---|---|---|---|
| NM_005507 | CFL1 | 0.9 | Direct interaction | CFL1 interacts with PLD1 | Homo sapiens | 17853892 |
| NM_005507 | CFL1 | 0.9 | Direct interaction | CFL1 interacts with MYCBP | Homo sapiens | 16169070 |
| NM_005507 | CFL1 | 0.9 | Direct interaction | CFL1 interacts with LIMK2 | Homo sapiens | 10436159 |
| NM_005507 | CFL1 | 0.9 | Direct interaction | CFL1 interacts with LIMK1 | Homo sapiens | 10436159\|12963706 |
| NM_005507 | CFL1 | 0.9 | Direct interaction | CFL1 interacts with HSPH1 | Homo sapiens | 14733918 |
| NM_005507 | CFL1 | 0.9 | Direct interaction | CFL1 and YWHAZ | Homo sapiens | 12361576 |
| NM_005507 | CFL1 | 0.9 | Direct interaction | CFL1 and PLD2 | Homo sapiens | 17853892 |
| NM_005507 | CFL1 | 0.9 | Direct interaction | CFL1 and PLD1 | Homo sapiens | 17853892 |
| NM_005507 | CFL1 | 0.9 | Direct interaction | CAP1 interacts with CFL1 | Homo sapiens | 11950878 |
| NM_005507 | CFL1 | 0.9 | Direct interaction | ATXN1 interacts with CFL1 | Homo sapiens | 16713569 |
| NM_005507 | CFL1 | 0.9 | Direct interaction | ACTG1 interacts with CFL1 | Homo sapiens | 16189514 |
| NM_005507 | CFL1 | 0.9 | Direct interaction | ACTB interacts with CFL1 | Homo sapiens | 16189514 |
| NM_005507 | CFL1 | 0.9 | Direct interaction | ACTA1 interacts with CFL1 | Homo sapiens | 11950878 |
| NM_006264 | PTPN13 | 0.6 | Direct interaction | Transcription factor IRF8 binds with PTPN13 gene | Homo sapiens | 18195016 |
| NM_006264 | PTPN13 | 0.6 | Direct interaction | PTPN13 physically interacts with TRIP6 | Homo sapiens | 10400701\|17591779 |
| NM_006264 | PTPN13 | 0.6 | Direct interaction | PLEKHA2 interacts with PTPN13 | Homo sapiens | 14516276 |
| NM_006264 | PTPN13 | 0.6 | Direct interaction | PKN2 interacts with PTPN13 | Homo sapiens | 11356191 |
| NM_006264 | PTPN13 | 0.6 | Direct interaction | PDCD10, PTPN13, STK25 (complex) | Homo sapiens | 17657516 |
| NM_006264 | PTPN13 | 0.6 | Direct interaction | PDCD10 interacts with PTPN13 | Homo sapiens | 17657516 |
| NM_006264 | PTPN13 | 0.6 | Direct interaction | NFKBIA interacts with PTPN13 | Homo sapiens | 14743216 9882613\|11106428 |
| NM_006264 | PTPN13 | 0.6 | Direct interaction | FASLG interacts with PTPN13 | Homo sapiens | 9261095 |
| NM_006264 | PTPN13 | 0.6 | Direct interaction | FAS interacts with PTPN13 | Homo sapiens | 10918185\|18195016 |
| NM_006264 | PTPN13 | 0.6 | Direct interaction | EFNB1 interacts with PTPN13 | Homo sapiens | 9920925 |
| NM_006264 | PTPN13 | 0.6 | Direct interaction | Dephosphorylation reaction involving PTPN13 and TRIP6 | Homo sapiens | 17591779 |
| NM_006264 | PTPN13 | 0.6 | Direct interaction | Dephosphorylation reaction involving NFKBIA and PTPN13 | Homo sapiens | 11106428 |
| NM_006264 | PTPN13 | 0.6 | Direct interaction | CTNNB1 interacts with PTPN13 | Homo sapiens | 10951583 |
| NM_006264 | PTPN13 | 0.6 | Direct interaction | Colocalization of PLEKHA1 and PTPN13 | Homo sapiens | 14516276 |
| NM_006264 | PTPN13 | 0.6 | Direct interaction | Colocalization of PKN2 and PTPN13 | Homo sapiens | 11356191 |
| NM_006264 | PTPN13 | 0.6 | Direct interaction | ARHGAP29 interacts with PTPN13 | Homo sapiens | 9305890 |
| NM_004177 | STX3 | 0.5 | Direct interaction | STX3 interacts with ZFYVE9 | Homo sapiens | 17693260 |
| NM_004177 | STX3 | 0.5 | Direct interaction | STX3 interacts with VCL | Homo sapiens | 15163412 |
| NM_004177 | STX3 | 0.5 | Direct interaction | STX3 interacts with VAMP3 | Homo sapiens | 12828989 |
| NM_004177 | STX3 | 0.5 | Direct interaction | STX3 interacts with VAMP2 | Homo sapiens | 12828989 |
| NM_004177 | STX3 | 0.5 | Direct interaction | STX3 interacts with TXLNA | Homo sapiens | 12558796 |
| NM_004177 | STX3 | 0.5 | Direct interaction | STX3 interacts with TLN1 | Homo sapiens | 15163412 |
| NM_004177 | STX3 | 0.5 | Direct interaction | STX3 interacts with SYT1 | Homo sapiens | 10397765 |
| NM_004177 | STX3 | 0.5 | Direct interaction | STX3 interacts with STXBP2 | Homo sapiens | 7768895 |

TABLE 9-continued

Immunity-related interacting protein partners of the identified target polypeptides.

| Unique Identifier | Gene Name | Log (Sum of Frequency) | Interaction Level | Interaction | Interactor Species | PMID |
|---|---|---|---|---|---|---|
| NM_004177 | STX3 | 0.5 | Direct interaction | STX3 interacts with STXBP1 | *Homo sapiens* | 7768895 |
| NM_004177 | STX3 | 0.5 | Direct interaction | STX3 interacts with Snap23 | *Mus musculus/ Homo sapiens* | 9168999 |
| NM_004177 | STX3 | 0.5 | Direct interaction | STX3 and ZFYVE9 | *Homo sapiens* | 17693260 |
| NM_004177 | STX3 | 0.5 | Direct interaction | SNAP29 interacts with STX3 | *Homo sapiens* | 9852078 |
| NM_004177 | STX3 | 0.5 | Direct interaction | SNAP25 interacts with STX3 | *Homo sapiens* | 8663154\|7768895\| 9852078 |
| NM_004177 | STX3 | 0.5 | Direct interaction | SNAP23 interacts with STX3 | *Homo sapiens* | 12828989\|8663154\| 9168999\|9852078 |
| NM_004177 | STX3 | 0.5 | Direct interaction | Colocalization of STX3 and ZFYVE9 | *Homo sapiens* | 17693260 |
| NM_005759 | ABI2 | 0.5 | Direct interaction | ABI2 interacts with VCL, KRT15, KRT19, KRT20, IFT20, NCK2, SNAP23, PCM1, CCDC53. | *Homo sapiens* | 16189514 |
| NM_005759 | ABI2 | 0.5 | Direct interaction | ABI2 interacts with TRIM32, UBC | *Homo sapiens* | 18632609 |
| NM_005759 | ABI2 | 0.5 | Direct interaction | ABI2 interacts with SH3KBP1 | *Homo sapiens* | 10858458 |
| NM_005759 | ABI2 | 0.5 | Direct interaction | ABI2 interacts with Enah, Wasf2, ABL1. | *Mus musculus/ Homo sapiens* | 17101133 |
| NM_005759 | ABI2 | 0.5 | Direct interaction | ABI2 interacts with ADAM19, ADAM22, ADAM9. | *Mus musculus/ Homo sapiens* | 12463424 |
| NM_005759 | ABI2 | 0.5 | Direct interaction | ABI2 interacts with ADAM19 | *Homo sapiens* | 12463424 |
| NM_005759 | ABI2 | 0.5 | Direct interaction | ABI2 interacts with ABL2 | *Homo sapiens* | 8649853 |
| NM_005759 | ABI2 | 0.5 | Direct interaction | ABI2 interacts with ABL1 | *Homo sapiens* | 12569093\|7590236 |
| NM_003513 | HIST1H2AB | 0.3 | Direct interaction | Transcription factor E2F4 binds with HIST1H2AB gene | *Homo sapiens* | 11799066 |
| NM_003513 | HIST1H2AB | 0.3 | Direct interaction | Transcription factor E2F1 binds with HIST1H2AB gene | *Homo sapiens* | 11799066 |
| NM_000978 | RPL23 | 0.3 | Direct interaction | RPL23, RPS6, WIBG (complex) | *Homo sapiens* | 19410547 |
| NM_000978 | RPL23 | 0.3 | Direct interaction | RPL23 interacts with TRAF2 | *Homo sapiens* | 14743216 |
| NM_000978 | RPL23 | 0.3 | Direct interaction | RPL23 interacts with TNFRSF1B | *Homo sapiens* | 14743216 |
| NM_000978 | RPL23 | 0.3 | Direct interaction | RPL23 interacts with TNFRSF1A | *Homo sapiens* | 14743216 |
| NM_000978 | RPL23 | 0.3 | Direct interaction | RPL23 interacts with TLN1 | *Homo sapiens* | 15163412 |
| NM_015435 | RNF19A | 0.3 | Direct interaction | RNF19A interacts with UBE2L6 | *Homo sapiens* | 11237715 |
| NM_015435 | RNF19A | 0.3 | Direct interaction | RNF19A interacts with UBE2L3 | *Homo sapiens* | 11237715 |
| NM_015435 | RNF19A | 0.3 | Direct interaction | RNF19A interacts with SP1 | *Homo sapiens* | 10976766 |
| NM_015435 | RNF19A | 0.3 | Direct interaction | RNF19A interacts with SOD1 | *Homo sapiens* | 17666395 |
| NM_000978 | RPL23 | 0.3 | Direct interaction | RIPK3 interacts with RPL23 | *Homo sapiens* | 14743216 |
| NM_000978 | RPL23 | 0.3 | Direct interaction | RIPK1 interacts with RPL23 | *Homo sapiens* | 14743216 |
| NM_000978 | RPL23 | 0.3 | Direct interaction | PXN interacts with RPL23 | *Homo sapiens* | 15163412 |
| NM_000978 | RPL23 | 0.3 | Direct interaction | NFKBIA interacts with RPL23 | *Homo sapiens* | 14743216 |
| NM_003513 | HIST1H2AB | 0.3 | Direct interaction | Methylation reaction involving HIST1H2AB and PRMT5 | *Homo sapiens* | 15670829 |
| NM_000978 | RPL23 | 0.3 | Direct interaction | MDM2 interacts with RPL23 | *Homo sapiens* | 17310983\|17110929 |
| NM_000978 | RPL23 | 0.3 | Direct interaction | MAP3K7IP2 interacts with RPL23 | *Homo sapiens* | 14743216 |

TABLE 9-continued

Immunity-related interacting protein partners of the identified target polypeptides.

| Unique Identifier | Gene Name | Log (Sum of Frequency) | Interaction Level | Interaction | Interactor Species | PMID |
|---|---|---|---|---|---|---|
| NM_000978 | RPL23 | 0.3 | Direct interaction | MAP3K3 interacts with RPL23 | Homo sapiens | 14743216 |
| NM_013958 | NRG1 | 0.3 | Direct interaction | LIMK1 interacts with NRG1 | Homo sapiens | 9685409 |
| NM_000978 | RPL23 | 0.3 | Direct interaction | IKBKG interacts with RPL23 | Homo sapiens | 14743216 |
| NM_022081 | HPS4 | 0.3 | Direct interaction | HPS1 interacts with HPS4 | Homo sapiens | 12756248 |
| NM_003513 | HIST1H2AB | 0.3 | Direct interaction | HIST1H2AB interacts with TNFRSF1A | Homo sapiens | 14743216 |
| NM_013958 | NRG1 | 0.3 | Direct interaction | ERBB4 and NRG1 | Homo sapiens | 9168115\|10970856 |
| NM_013958 | NRG1 | 0.3 | Direct interaction | ERBB3 and NRG1 | Homo sapiens | 9168115\|11555649\|17697999\|10970856\|7592681 |
| NM_013958 | NRG1 | 0.3 | Direct interaction | ERBB2 interacts with NRG1 | Homo sapiens | 7592681 |
| NM_013958 | NRG1 | 0.3 | Direct interaction | EGFR interacts with NRG1 | Homo sapiens | 7730382 |
| NM_000978 | RPL23 | 0.3 | Direct interaction | Colocalization of RPL23 and WIBG | Homo sapiens | 19410547 |
| NM_152609 | C1orf71 | 0.3 | Direct interaction | C1orf71 interacts with EWSR1 | Homo sapiens | 16189514 |
| NM_000978 | RPL23 | 0.3 | Direct interaction | BCCIP interacts with RPL23 | Homo sapiens | 16189514 |
| NM_004322 | BAD | 5.5 | Direct interaction | ABLIM1, AKT1S1, ARAF, BAD, BAIAP2, BCAR1, BRAF, C1QBP, CEP250, CGN, CLASP1, CLASP2, CRTC1, CSNK1A1, DENND4A, EIF4E2, FAM53C, FOXO3, HDAC4, HDAC7, HSPA8, IRS2, KIF1B, KIF1C, KIF23, KIF5B, KLC1; C14orf153, KLC2, KLC3, KLC4, KSR1, LARP1, LIMA1, LMO7, LSR, MAP3K2, MARK2, MARK3, MAST2, MAST3, MLLT4, NADK, OSBPL3, PAK4, PARD3, PCTK3, PDZD11, PFKFB2, PKP2, PRKCI, PTPN14, RAB11FIP1, RAB11FIP2, RABEP1, RAF1, RASSF8, REEP1, SHROOM2, SLC25A6, SRGAP2, TBC1D1, TBC1D4, TEAD3, TIAM1, TP53BP2, TRIP11, TRIP11, TSC1, TSC2, USP8, VAMP8, WDR68, YWHAB, YWHAG, YWHAH, YWHAH, YWHAQ, YWHAZ, ZFP36L2 (complex). | Homo sapiens | 17979178 |
| NM_001028 | RPS25 | 2.2 | Direct interaction | ACTB, ADSL; TNRC6B, AGK, ARF4, ATP5C1, ATP5I, CCT5, CDIPT, DBT, DNAJA1, DNAJA2, DNAJB11, EEF1A1, EIF2C2, EIF2C3, EIF2C4, EIF4B, EMD, GALK1, HIST1H2AB, HNRNPC, HSP90AA1, HSP90AB1, HSPA1B, HSPA5, HSPA8, IDBG-12906, IGF2BP1, IPO8, JAK1, MYCBP, PABPC1, PABPC4, PGAM5, PRDX1, PRMT5, PTGES3, PTS, QPCTL, RBM10, RPL11, RPL12, RPL23, RPL24, RPL27, RPL27A, RPL35, RPL38, RPL8, RPS10L, RPS12, RPS18, RPS25, RPS26, RPS3A, RPS5, RPS9, SLC25A1, SLC25A10, SLC25A13, SLC25A22, SLC25A3, SLC25A5, SNRPD2, SSBP1, SUCLA2, TNRC6A, TRIM21, TUBA1A, TUBB, TUBB2C, TUFM, TUT1, WDR77, YBX1 (complex) | Homo sapiens | 19167051 |
| NM_003513 | HIST1H2AB | 0.3 | | | | |
| NM_000978 | RPL23 | 0.3 | | | | |

TABLE 9-continued

Immunity-related interacting protein partners of the identified target polypeptides.

| Unique Identifier | Gene Name | Log (Sum of Frequency) | Interaction Level | Interaction | Interactor Species | PMID |
|---|---|---|---|---|---|---|
| NM_000978 | RPL23 | 0.3 | Direct interaction | ARHGEF4, CUL1, CUL2, CUL3, CUL4A, CUL4B, CUL5, DDB1, DDX19B, EEF1A1, EEF1A2, EEF2, EIF2A, EMG1, ERCC4, GCN1L1, H2AFX, HARS, HIST2H2BE, KARS, MCM4, MCM5, NAE1, NEDD8, PCNA, PIAS1, PIAS1, PIAS2, PRPF3, PSMD2, RPL10A, RPL11, RPL12, RPL13, RPL14, RPL18, RPL21, RPL23, RPL23, RPL24, RPL26, RPL27, RPL29, RPL30, RPL31, RPL35A, RPL5, RPL6, RPL7, RPL7A, RPL8, RPL9, RPS11, RPS13, RPS14, RPS15A, RPS16, RPS2, RPS20, RPS23, RPS26P25, RPS3, RPS4X, RPS6, RPS7, RPS8, SCN1A, SF3B3, SSRP1, SUMO3, TARS, UBA52, UBE2M, YWHAG, YWHAH (complex) | Homo sapiens | 18274552 |

EXAMPLE 4

Methods Summary

Human whole-genome screen: A549 cells were transduced at MOI 0.3 with each of 7 Decode RNA GIPZ Lentiviral Positive Screening Library pools according to manufacturer's protocol (Open Biosystems). After 72 h, cells were washed twice with 1× phosphate-buffered saline (PBS) and infected with NY55 at an MOI of 7 PFU per cell. At 72 hpi, cells were washed twice with 1×PBS and harvested. Genomic DNA was isolated by phenol/chloroform extraction followed by ethanol precipitation.

PCR: PCR was carried out on isolated genomic DNA using Expand High Fidelity polymerase mix (Roche) and product was purified from polyacrylamide gels. Pooled cDNA was sequenced by high-throughput Illumina® sequencing technology at Canada's Michael Smith Genome Sciences Centre (Vancouver, British Columbia).

Lentivirus packaging and transduction: Individual human shRNAmir lentiviral clones (Thermo Scientific Open Biosystems; 3-4 for each gene target of interest) were prepared and isolated according to manufacturer's protocol. Individual shRNAs were packaged into lentivirus particles by co-transfection of each shRNAmir with pMD2.G and psPAX2 (Addgene plasmid 12260) in individual sets of HEK-293T cells according to Open Biosystems' Trans-lentiviral Packaging protocol. A549 cells were transduced with lentivirus at an MOI of 0.5. At 72 h post transduction, 3 μg/ml puromycin (Sigma) was added to the media. Cells were passaged twice in puromycin-supplemented completed media to select transductants before they were infected with virus (described below).

siRNA Transfection: Sets of A549 cells were treated with 25 nM of each of 40N-Targetplus siRNA (Dharmacon) targeting each of the USP47, TNFSF12-13, TNFSF13, and BAD genes. siRNAs were introduced into cells with Lipofectamine RNAiMAX (Invitrogen). Each cell set was re-treated with the same siRNA 24 h later. After a further 24 h, cells were infected with virus at an MOI 0.1 and harvested for analysis 48 hpi.

Influenza virus infections: Sets of transduced or transfected A549 cells were infected with influenza virus strains A/NY/55/2004(H3N2) at an MOI of 1 PFU/cell, or with A/PR/8/34(H1N1) at an MOI of 0.01, or with SOIV at an MOI of 0.1 and harvested at 48 hpi for virus titration by plaque assay.

Influenza plaque assay: Influenza plaque assay was carried out on MDCK cells as previously described[22].

Bioinformatics Analysis: Sequences were analysed by an in-house computer algorithm. Genes were functionally categorized using PANTHER ontology system[23,24]. Network analysis were done with InnateDB[20] database and visualization employing Cerebral[21].

TABLE 10

Replication of A/NY/55/2004(H3N2) in shRNA knockdown A549 cells. Cells were transduced with shRNA---packaged lentivirus at MOI 0.5, and infected 72 h later at MOI 1. Standard Deviation represents 3 biological replicates.

| Gene | shRNA | % of non-silencing | Standard Deviation |
|---|---|---|---|
| Non-silencing | | 100.00 | 0.00 |
| (MxB) | 152031 | 18.94 | 20.54 |
| (TNFSF) | 17313 | 30.98 | 15.24 |
| | 17314 | 27.46 | 10.54 |
| | 17316 | 22.73 | 16.40 |
| | 17317 | 14.85 | 15.79 |
| | 17318 | 16.53 | 20.25 |
| (BAD) | 15289 | 23.29 | 14.97 |
| | 201511 | 11.93 | 22.52 |
| | 202976 | 29.91 | 36.72 |
| (USP47) | 174637 | 13.23 | 20.82 |
| | 174641 | 25.45 | 32.42 |
| | 174642 | 176.72 | 33.88 |
| | 174639 | 59.96 | 118.71 |
| | 218228 | 42.49 | 90.22 |

TABLE 11

Replication of A/NY/55/2004(H3N2) in A549 siRNA transfected cells. Cells were treated with 25 pmol siRNA twice, 24 h apart, and after a further 24 h were infected at MOI 0.1. Standard Deviation Represents 2 biological replicates.

| Gene | siRNA | % of non-silencing | Standard Deviation |
|---|---|---|---|
| Non-silencing | | 100.00 | 0.00 |
| USP47 | si05 | 4.48 | 7.42 |
| | si06 | 9.95 | 12.22 |
| | si07 | 15.92 | 1.07 |

TABLE 11-continued

Replication of A/NY/55/2004(H3N2) in A549 siRNA transfected cells. Cells were treated with 25 pmol siRNA twice, 24 h apart, and after a further 24 h were infected at MOI 0.1. Standard Deviation Represents 2 biological replicates.

| Gene | siRNA | % of non-silencing | Standard Deviation |
|---|---|---|---|
|  | si08 | 18.91 | 30.15 |
| BAD | si09 | 22.39 | 9.40 |
|  | si10 | 16.42 | 17.47 |
|  | si11 | 18.91 | 10.13 |
|  | si12 | 23.38 | 19.09 |
| MxB | si05 | 19.40 | 11.12 |
|  | si06 | 1.49 | 0.09 |
|  | si07 | 0 | 0.00 |
|  | si08 | 3.48 | 5.43 |
| TNFSF12-13 | si05 | 5.47 | 1.72 |
|  | si06 | 5.97 | 3.45 |
|  | si07 | 2.49 | 2.72 |
|  | si08 | 15.42 | 3.16 |
| TNFSF13 | si05 | 16.42 | 8.23 |
|  | si06 | 12.44 | 0.26 |
|  | si07 | 1.99 | 2.18 |
|  | si08 | 3.98 | 3.35 |

All citations are herein incorporated by reference, as if each individual publication was specifically and individually indicated to be incorporated by reference herein and as though it were fully set forth herein. Citation of references herein is not to be construed nor considered as an admission that such references are prior art to the present invention.

One or more currently preferred embodiments of the invention have been described by way of example. The invention includes all embodiments, modifications and variations substantially as hereinbefore described and with reference to the examples and figures. It will be apparent to persons skilled in the art that a number of variations and modifications can be made without departing from the scope of the invention as defined in the claims. Examples of such modifications include the substitution of known equivalents for any aspect of the invention in order to achieve the same result in substantially the same way.

References

1. Smith, N. M. et al., Prevention and Control of Influenza: recommendations of the Advisory Committee on Immunization Practices (ACIP). *MMWR. Recommendations and reports: Morbidity and mortality weekly report. Recommendations and reports/Centers for Disease Control* 55 (RR-10), 1-42 (2006).
2. Wikramaratna, P. S. & Gupta, S., Influenza outbreaks. *Cell. Microbiol.* 11 (7), 1016-1024 (2009).
3. Pappaioanou, M., Highly pathogenic H5N1 avian influenza virus: cause of the next pandemic? *Comp. Immunol. Microbiol. Infect. Dis.* 32, 287-300 (2009).
4. Schnitzler, S. U. & Schnitzler, P., An update on swine-origin influenza virus A/H1N1: a review. *Virus Genes* 39, 279-292 (2009).
5. Hao, L. et al., *Drosophila* RNAi screen identifies host genes important for influenza virus replication. *Nature* 454, 890-894 (2008).
6. König, R. et al., Human host factors required for influenza virus replication. *Nature* (2009).
7. Karlas, A. et al., Genome-wide RNAi screen identifies human host factors crucial for influenza virus replication. *Nature* (2010).
8. Kobasa, D. et al., Aberrant innate immune response in lethal infection of macaques with the 1918 influenza virus. *Nature* 445, 319-323 (2007).
9. Mauad, T. et al., Lung pathology in fatal novel human influenza A (H1N1) infection. *Am. J. Respir. Crit. Care Med.* 181, 72-79 (2010).
10. Baskin, C. r. et al., Integration of Clinical Data, Pathology, and cDNA microarrays in influenza virus-infected pig-tailed macaques (*Macaca nemestrina*). *J. Virol.* 78 (19), 10420-10432 (2004).
11. Wolter, N. M. & MacKeigan, J. P., From sequence to function: using RNAi to elucidate the mechanisms of human disease. *Cell Death Differ.* 15, 809-819 (2008).
12. Pradet-Balade, B. et al., An endogenous hybrid mRNA encodes TWE-PRIL, a functional cell surface TWEAK-APRIL fusion protein. *EMBO J.* 21 (21), 5711-5720 (2002).
13. Daridon, C., Youinou, P., & Pers, J. -O., BAFF, APRIL, TWE-PRIL: who's who? *Autoimmun. Rev.* 7, 267-271 (2008).
14. Hardenberg, G., van der Sluijs, K., van der Poll, T., & Medema, J. P., APRIL affects antibody responses and early leukocyte infiltration, but not influenza A viral control. *Mol. Immunol.* 45, 3050-3058 (2008).
15. Pavlovic, J., Haller, O., & Staeheli, P., Human and mouse Mx proteins inhibit different steps of the influenza virus multiplication cycle. *J. Virol.* 66 (4), 2564-2569 (1992).
16. Pavlovic, J., Zürcher, T., Haller, O., & Staeheli, P., Resistance to influenza virus and vesicular stomatitis virus conferred by expression of human MxA protein. *J. Virol.* 64 (7), 3370-3375 (1990).
17. Haller, O. & Kochs, G., Interferon-induced Mx proteins: dynamin-like GTPases with antiviral activity. *Traffic* 3 (10), 710-717 (2002).
18. King, M. C., Raposo, G., & Lemmon, M. A., Inhibition of nuclear import and cell-cycle progression by mutated forms of the dynamin-like GTPase MxB. *Proc. Natl. Acad. Sci. U.S.A.* 101 (24), 8957-8962 (2004).
19. Quesada, V. et al., Cloning and enzymatic analysis of 22 novel human ubiquitin-specific proteases. *Biochem. Biophys. Res. Commun.* 314, 54-62 (2004).
20. Lynn, D. J. et al., InnateDB: facilitating systems-level analyses of the mammalian innate immune response. *Mol. Syst. Biol.* 4 (218), 218-226 (2008).
21. Barsky, A., Gardy, J. L., Hancock, R. E. W., & Munzner, T., Cerebral: a Cytoscape plugin for layout of and interaction with biological networks using subcellular localization annotation. *Bioinformatics* 23 (8), 1040-1042 (2007).
22. Szretter, K. J., Balish, A. L., & Katz, J.248 M., Influenza: propagation, quantification, and storage in *Curr Protoc Microbiol* (2006).
23. Mi, H. et al., The PANTHER database of protein familes, subfamiles, functions and pathways. *Nucleic Acids Res.* 33, D284-D288 (2005).
24. Thomas, P. D. et al., PANTHER: A library of protein families and subfamilies indexed by function. *Genome Res.* 13, 2129-2141 (2003).
25. Paddison et al., Genes & Dev. 16: 948-958, 2002.
26. Bass, Nature, 411:428-29, 2001.
27. Elbashir et al., Nature, 411:494-98, 2001.
28. Fire et al., Nature, 391:806-11, 1998.
29. Scherr et al., Curr. Med. Chem., 2003; 10(3):245-56).
30. Abbas-Turki et al., Hum. Gene Ther., 2002; 13(18):2197-201).
31. Tiscornia et al., Proc. Natl. Acad. Sci. U.S.A., 2003; 100:1844-8).

What is claimed is:

1. A method of reducing influenza virus replication comprising contacting virus-infected cells with an effective amount of an inhibitor of BCL2-associated agonist of cell death (BAD) wherein the inhibitor is selected from siRNA or shRNA.

2. A method of reducing influenza virus-mediated cytotoxicity comprising contacting virus-infected cells with an effective amount of an inhibitor of BAD wherein the inhibitor is selected from siRNA or shRNA.

3. A method for treating an influenza viral infection in a subject comprising administering to the subject a composition comprising an inhibitor of BAD wherein the inhibitor is selected from siRNA or shRNA, wherein the composition reduces expression or activity of BAD when administered to the subject.

4. The method of claim 1, 2 or 3, wherein the inhibitor is an siRNA.

5. The method of claim 1, 2 or 3, wherein the inhibitor is an siRNA comprising SEQ ID NO: 9.

6. The method of claim 1 or 2, wherein the cells are contacted by the inhibitor in vivo.

7. The method of claim 3, wherein the subject is a mammal.

8. The method of claim 7, wherein the mammal is a human.

* * * * *

SEQUENCE LISTING

<160> NUMBER OF SEQ ID NOS: 103

<210> SEQ ID NO 1
<211> LENGTH: 19
<212> TYPE: DNA
<213> ORGANISM: Artificial Sequence
<220> FEATURE:
<223> OTHER INFORMATION: BAD shRNA V2HS_15289

<400> SEQUENCE: 1
ctcactacca aatgttaat                                            19

<210> SEQ ID NO 2
<211> LENGTH: 19
<212> TYPE: DNA
<213> ORGANISM: Artificial Sequence
<220> FEATURE:
<223> OTHER INFORMATION: BAD shRNA V2HS_243025

<400> SEQUENCE: 2
cagtgacctt cgctccaca                                            19

<210> SEQ ID NO 3
<211> LENGTH: 19
<212> TYPE: DNA
<213> ORGANISM: Artificial Sequence
<220> FEATURE:
<223> OTHER INFORMATION: BAD shRNA V2HS_201511

<400> SEQUENCE: 3
gagtttgtgg actccttta                                            19

<210> SEQ ID NO 4
<211> LENGTH: 19
<212> TYPE: DNA
<213> ORGANISM: Artificial Sequence
<220> FEATURE:
<223> OTHER INFORMATION: BAD shRNA V2HS_202976

<400> SEQUENCE: 4
gtgctcacta ccaaatgtt                                            19

<210> SEQ ID NO 5
<211> LENGTH: 19
<212> TYPE: DNA
<213> ORGANISM: Artificial Sequence
<220> FEATURE:
<223> OTHER INFORMATION: BAD shRNA V2HS_262043

<400> SEQUENCE: 5
gacttggact tggatgtaa                                            19

<210> SEQ ID NO 6
<211> LENGTH: 19
<212> TYPE: RNA
<213> ORGANISM: Artificial Sequence
<220> FEATURE:
<223> OTHER INFORMATION: BAD siRNA J-003870-09

<400> SEQUENCE: 6
gaucggaacu ugggcaggg                                            19

<210> SEQ ID NO 7
<211> LENGTH: 19
<212> TYPE: RNA

```
<213> ORGANISM: Artificial Sequence
<220> FEATURE:
<223> OTHER INFORMATION: BAD siRNA J-003870-10

<400> SEQUENCE: 7
cagaguuuga gccgaguga                                                    19

<210> SEQ ID NO 8
<211> LENGTH: 19
<212> TYPE: RNA
<213> ORGANISM: Artificial Sequence
<220> FEATURE:
<223> OTHER INFORMATION: BAD siRNA J-003870-11

<400> SEQUENCE: 8
gagcuccgga ggaugagug                                                    19

<210> SEQ ID NO 9
<211> LENGTH: 19
<212> TYPE: RNA
<213> ORGANISM: Artificial Sequence
<220> FEATURE:
<223> OTHER INFORMATION: BAD siRNA J-003870-12

<400> SEQUENCE: 9
uuguggacuc cuuuaagaa                                                    19

<210> SEQ ID NO 10
<211> LENGTH: 1240
<212> TYPE: DNA
<213> ORGANISM: Homo sapiens

<400> SEQUENCE: 10
aactagggcc cggagcccgg ggtgctggag ggaggcggca ggcccgggtc agggggcctcg         60 agatcgggct tggggtgaga cctgtgcgcc gtcaccacgg gcggggcggg gcctgggtcc        120 accgggttc tgagggagaa ctgaggtcct gagccgacag cctcagctcc ctgccaggcc        180
agacccggca gacagatgag ggcccaggag gcctggcggg cctggggggcg ctacggtggg        240 agaggaagcc aggggtacct gcctctgcct tccaggggca ccgttggccc cagctgtgcc        300
ttgactacgt aacatcttgt cctcacagcc cagagcatgt tccagatccc agagtttgag        360
ccgagtgagc aggaagactc cagctctgca gagagggggcc tgggcccag ccccgcaggg        420 gacgggccct caggctccgg caagcatcat cgccaggccc caggcctcct gtgggacgcc        480
agtcaccagc aggagcagcc aaccagcagc agccatcatg gaggcgctgg ggctgtggag        540
atccggagtc gccacagctc ctaccccgcg gggacggagg acgacgaagg gatggggag        600 gagcccagcc cctttcgggg ccgctcgcgc tcggcgcccc ccaacctctg ggcagcacag        660
cgctatggcc gcgagctccg gaggatgagt gacgagtttg tggactcctt taagaaggga        720
cttcctcgcc cgaagagcgc gggcacagca acgcagatgc ggcaaagctc cagctggacg        780
cgagtcttcc agtcctggtg ggatcggaac ttgggcaggg gaagctccgc cccctcccag        840
tgaccttcgc tccacatccc gaaactccac ccgttccac tgcccctgggc agccatcttg        900 aatatgggcg gaagtacttc cctcaggcct atgcaaaaag aggatccgtg ctgtctcctt        960
tggagggagg gctgacccag attcccttcc ggtgcgtgtg aagccacgga aggcttggtc       1020
ccatcggaag ttttgggttt tccgcccaca gccgccggaa gtggctccgt ggccccgccc       1080
tcaggctccg gctttccccc caggcgcctg cgctaagtcg cgagccaggt ttaaccgttg       1140
cgtcaccggg acccgagccc ccgcgatgcc ctggggggccg tgctcactac caaatgttaa       1200
```

-continued

```
taaagcccgc gtctgtgccg ccgaaaaaaa aaaaaaaaaa                              1240
```

<210> SEQ ID NO 11
<211> LENGTH: 19
<212> TYPE: DNA
<213> ORGANISM: Artificial Sequence
<220> FEATURE:
<223> OTHER INFORMATION: TNFSF12-TNFSF13/TNFSF13 shRNA V2HS_17313

<400> SEQUENCE: 11

```
gccgccctct gctagggaa                                                      19
```

<210> SEQ ID NO 12
<211> LENGTH: 19
<212> TYPE: DNA
<213> ORGANISM: Artificial Sequence
<220> FEATURE:
<223> OTHER INFORMATION: TNFSF12-TNFSF13/TNFSF13 shRNA V2HS_17314

<400> SEQUENCE: 12

```
gatattctga gtgtcataa                                                      19
```

<210> SEQ ID NO 13
<211> LENGTH: 19
<212> TYPE: DNA
<213> ORGANISM: Artificial Sequence
<220> FEATURE:
<223> OTHER INFORMATION: TNFSF12-TNFSF13/TNFSF13 shRNA V2HS_17316

<400> SEQUENCE: 13

```
ggtgccttcg cagtcaaat                                                      19
```

<210> SEQ ID NO 14
<211> LENGTH: 19
<212> TYPE: DNA
<213> ORGANISM: Artificial Sequence
<220> FEATURE:
<223> OTHER INFORMATION: TNFSF12-TNFSF13/TNFSF13 shRNA V2HS_17317

<400> SEQUENCE: 14

```
gagactctat tccgatgta                                                      19
```

<210> SEQ ID NO 15
<211> LENGTH: 19
<212> TYPE: DNA
<213> ORGANISM: Artificial Sequence
<220> FEATURE:
<223> OTHER INFORMATION: TNFSF12-TNFSF13/TNFSF13 shRNA V2HS_17318

<400> SEQUENCE: 15

```
ctccagagat gtagctatt                                                      19
```

<210> SEQ ID NO 16
<211> LENGTH: 19
<212> TYPE: RNA
<213> ORGANISM: Artificial Sequence
<220> FEATURE:
<223> OTHER INFORMATION: TNFSF12-TNFSF13/TNFSF13 siRNA J-032530-05

<400> SEQUENCE: 16

```
gggcaagggc gaaacuuaa                                                      19
```

<210> SEQ ID NO 17
<211> LENGTH: 19
<212> TYPE: RNA
<213> ORGANISM: Artificial Sequence
<220> FEATURE:

```
<223> OTHER INFORMATION: TNFSF12-TNFSF13/TNFSF13 siRNA J-032530-06

<400> SEQUENCE: 17
gcaggugucu uccauuuac                                                   19

<210> SEQ ID NO 18
<211> LENGTH: 19
<212> TYPE: RNA
<213> ORGANISM: Artificial Sequence
<220> FEATURE:
<223> OTHER INFORMATION: TNFSF12-TNFSF13/TNFSF13 siRNA J-032530-07

<400> SEQUENCE: 18
ugacagaggu gauguggca                                                   19

<210> SEQ ID NO 19
<211> LENGTH: 19
<212> TYPE: RNA
<213> ORGANISM: Artificial Sequence
<220> FEATURE:
<223> OTHER INFORMATION: TNFSF12-TNFSF13/TNFSF13 siRNA J-032530-08

<400> SEQUENCE: 19
ggaguuuauc ugcuguaua                                                   19

<210> SEQ ID NO 20
<211> LENGTH: 19
<212> TYPE: RNA
<213> ORGANISM: Artificial Sequence
<220> FEATURE:
<223> OTHER INFORMATION: TNFSF12-TNFSF13 siRNA J-011523-05

<400> SEQUENCE: 20
gggcaagggc gaaacuuaa                                                   19

<210> SEQ ID NO 21
<211> LENGTH: 19
<212> TYPE: RNA
<213> ORGANISM: Artificial Sequence
<220> FEATURE:
<223> OTHER INFORMATION: TNFSF12-TNFSF13 siRNA J-011523-06

<400> SEQUENCE: 21
gcaggugucu uccauuuac                                                   19

<210> SEQ ID NO 22
<211> LENGTH: 19
<212> TYPE: RNA
<213> ORGANISM: Artificial Sequence
<220> FEATURE:
<223> OTHER INFORMATION: TNFSF12-TNFSF13 siRNA J-011523-07

<400> SEQUENCE: 22
ugacagaggu gauguggca                                                   19

<210> SEQ ID NO 23
<211> LENGTH: 19
<212> TYPE: RNA
<213> ORGANISM: Artificial Sequence
<220> FEATURE:
<223> OTHER INFORMATION: TNFSF12-TNFSF13 siRNA J-011523-08

<400> SEQUENCE: 23
ggaguuuauc ugcuguaua                                                   19

<210> SEQ ID NO 24
```

<211> LENGTH: 2961
<212> TYPE: DNA
<213> ORGANISM: Homo sapiens

<400> SEQUENCE: 24

| | | | | | |
|---|---|---|---|---|---|
| aagagatgat | ttctccatcc | tgaacgtgca | gcgagcttgt | caggaagatc | ggaggtgcca | 60 |
| agtagcagag | aaagcatccc | ccagctctga | cagggagaca | gcacatgtct | aaggcccaca | 120 |
| agccttggcc | ctaccggagg | agaagtcaat | tttcttctcg | aaaatacctg | aaaaaagaaa | 180 |
| tgaattcctt | ccagcaacag | ccaccgccat | tcggcacagt | gccaccacaa | atgatgtttc | 240 |
| ctccaaactg | gcaggggggca | gagaaggacg | ctgctttcct | cgccaaggac | ttcaactttc | 300 |
| tcactttgaa | caatcagcca | ccaccaggaa | acaggagcca | accagggca | atggggcccg | 360 |
| agaacaacct | gtacagccag | tacgagcaga | aggtgcgccc | ctgcattgac | ctcatcgact | 420 |
| ccctgcgggc | tctgggtgtg | gagcaggacc | tggccctgcc | agccatcgcc | gtcatcgggg | 480 |
| accagagctc | gggcaagagc | tctgtgctgg | aggcactgtc | aggagtcgcg | cttcccagag | 540 |
| gcagcggaat | cgtaaccagg | tgtccgctgg | tgctgaaact | gaaaaagcag | ccctgtgagg | 600 |
| catgggccgg | aaggatcagc | taccggaaca | ccgagctaga | gcttcaggac | cctggccagg | 660 |
| tggagaaaga | gatacacaaa | gcccagaacg | tcatggccgg | gaatggccgg | ggcatcagcc | 720 |
| atgagctcat | cagcctggag | atcacctccc | ctgaggttcc | agacctgacc | atcattgacc | 780 |
| ttcccggcat | caccagggtg | gctgtggaca | accagccccg | agacatcgga | ctgcagatca | 840 |
| aggctctcat | caagaagtac | atccagaggc | agcagacgat | caacttggtg | gtggttccct | 900 |
| gtaacgtgga | cattgccacc | acggaggcgc | tgagcatggc | ccatgaggtg | gacccggaag | 960 |
| gggacaggac | catcggtatc | ctgaccaaac | cagatctaat | ggacagggc | actgagaaaa | 1020 |
| gcgtcatgaa | tgtggtgcgg | aacctcacgt | acccccctcaa | gaagggctac | atgattgtga | 1080 |
| agtgccgggg | ccagcaggag | atcacaaaca | ggctgagctt | ggcagaggca | accaagaaag | 1140 |
| aaattacatt | ctttcaaaca | catccatatt | tcagagttct | cctggaggag | gggtcagcca | 1200 |
| cggttccccg | actggcagaa | agacttacca | ctgaactcat | catgcatatc | caaaaatcgc | 1260 |
| tcccgttgtt | agaaggacaa | ataagggaga | gccaccagaa | ggcgaccgag | gagctgcggc | 1320 |
| gttgcggggc | tgacatcccc | agccaggagg | ccgacaagat | gttctttcta | attgagaaaa | 1380 |
| tcaagatgtt | taatcaggac | atcgaaaagt | tagtagaagg | agaagaagtt | gtaagggaga | 1440 |
| atgagacccg | tttatacaac | aaaatcagag | aggattttaa | aaactgggta | ggcatacttg | 1500 |
| caactaatac | ccaaaaagtt | aaaaatatta | tccacgaaga | agttgaaaaa | tatgaaaagc | 1560 |
| agtatcgagg | caaggagctt | ctgggatttg | tcaactacaa | gacatttgag | atcatcgtgc | 1620 |
| atcagtacat | ccagcagctg | gtggagcccg | cccttagcat | gctccagaaa | gccatggaaa | 1680 |
| ttatccagca | agctttcatt | aacgtggcca | aaaacatttt | tggcgaattt | ttcaacctta | 1740 |
| accaaactgt | tcagagcacg | attgaagaca | taaaagtgaa | acacacagca | aaggcagaaa | 1800 |
| acatgatcca | acttcagttc | agaatggagc | agatggtttt | ttgtcaagat | cagatttaca | 1860 |
| gtgttgttct | gaagaaagtc | cgagaagaga | ttttttaaccc | tctggggacg | ccttcacaga | 1920 |
| atatgaagtt | gaactctcat | tttcccagta | atgagtcttc | ggtttcctcc | tttactgaaa | 1980 |
| taggcatcca | cctgaatgcc | tacttcttgg | aaaccagcaa | acgtctcgcc | aaccagatcc | 2040 |
| catttataat | tcagtatttt | atgctccgag | agaatggtga | ctccttgcag | aaagccatga | 2100 |
| tgcagatact | acaggaaaaa | aatcgctatt | cctggctgct | tcaagagcag | agtgagaccg | 2160 |
| ctaccaagag | aagaatccttt | aaggagagaa | tttaccggct | cactcaggcg | cgacacgcac | 2220 |

-continued

```
tctgtcaatt ctccagcaaa gagatccact gaagggcggc gatgcctgtg gttgttttct    2280
tgtgcgtact cattcattct aaggggagtc ggtgcaggat gccgcttctg ctttggggcc    2340
aaactcttct gtcactatca gtgtccatct ctactgtact ccctcagcat cagagcatgc    2400
atcaggggtc cacacaggct cagtctctc caccacccag ctcttccctg accttcacga    2460
agggatggct ctccagtcct tgggtcccgt agcacacagt tacagtgtcc taagatactg    2520
ctatcattct tcgctaattt gtatttgtat tcccttcccc ctacaagatt atgagacccc    2580 agaggggaa ggtctgggtc aaattcttct tttgtatgtc cagtctcctg cacagcacct     2640
gcagcattgt aactgcttaa taaatgacat ctcactgaac gaatgagtgc tgtgtaagtg    2700
atggagatac ctgaggctat tgctcaagcc caggccttgg acatttagtg actgttagcc    2760 ggtcccttc agatccagtg gccatgcccc ctgcttccca tggttcactg tcattgtgtt     2820
tcccagcctc tccactcccc cgccagaaag gagcctgagt gattctcttt tcttcttgtt    2880
tccctgatta tgatgagctt ccattgttct gttaagtctt gaagaggaat ttaataaagc    2940
aaagaaactt tttaaaaacg t    2961

<210> SEQ ID NO 25
<211> LENGTH: 19
<212> TYPE: DNA
<213> ORGANISM: Artificial Sequence
<220> FEATURE:
<223> OTHER INFORMATION: MX2 shRNA  V2HS_152031

<400> SEQUENCE: 25
gacaagatgt tctttctaa                                                 19

<210> SEQ ID NO 26
<211> LENGTH: 19
<212> TYPE: RNA
<213> ORGANISM: Artificial Sequence
<220> FEATURE:
<223> OTHER INFORMATION: MX2 siRNA J-011736-05

<400> SEQUENCE: 26
gagcacgauu gaagacaua                                                 19

<210> SEQ ID NO 27
<211> LENGTH: 19
<212> TYPE: RNA
<213> ORGANISM: Artificial Sequence
<220> FEATURE:
<223> OTHER INFORMATION: MX2 siRNA J-011736-06

<400> SEQUENCE: 27
ggagaaugag acccguuua                                                 19

<210> SEQ ID NO 28
<211> LENGTH: 19
<212> TYPE: RNA
<213> ORGANISM: Artificial Sequence
<220> FEATURE:
<223> OTHER INFORMATION: MX2 siRNA J-011736-07

<400> SEQUENCE: 28
gaauuuaccg gcucacuca                                                 19

<210> SEQ ID NO 29
<211> LENGTH: 19
<212> TYPE: RNA
<213> ORGANISM: Artificial Sequence
<220> FEATURE:
```

<223> OTHER INFORMATION: MX2 siRNA J-011736-08

<400> SEQUENCE: 29
gggacgccuu cacagaaua                                                    19

<210> SEQ ID NO 30
<211> LENGTH: 7777
<212> TYPE: DNA
<213> ORGANISM: Homo sapiens

<400> SEQUENCE: 30

| | | |
|---|---|---|
| agaggggaaa agaacgtcag gagagtgaac gggagcaaat aaaacgctgt ccattctgac | 60 |
| tggaagggcc agagccgtgt ctaagggcgg gggccgggag gtggcccgcg gtggtgtctc | 120 |
| taccaggacg aggcctgggg tatctgaaga ggggatgacg tccaggcgct ttgctaaagg | 180 |
| gaagccagaa gggtatgagt tgctagggtc agagatgggg ctttcggctc gagtcttttcc | 240 |
| ctgcagggca gagagtccga agagcccgag aaggcaggga ggacagtggg cctggtcctt | 300 |
| ccccggccgg cagagggagt cccgagatgg aacgtccagc tctcctctaa cgaaaagcgt | 360 |
| ttgcatggct gtctcgccaa ttctgtacct cccggggctg aggaagagcc gaggtgacta | 420 |
| gaagctagcg acaagtgccg gccacctccg acgccaggcg ccgggcttgg agcccgacgg | 480 |
| gccgaattct cgcgagagcg gccgccgcca ttttttccatt gattgcagcg ggctggggga | 540 |
| ggggccgacg acgaaggcgg ctgtggtagc ggcggcgggcg gcggcggagc cctgggtcgg | 600 |
| tgtctgcgcg ctggtgtctg aggcccaggc tgaggcctcc gctattgctg gagcgcaggc | 660 |
| ggcggagagg atgactgccg ctgccattct ctcttgagct agcgagccgc cgccaccctc | 720 |
| caccctcccc cggcagggcg gagaggagcg gccggagtca gcgatggtgc ccggcgagga | 780 |
| gaaccaactg gtcccgaaag aggcaccact ggatcatacc agtgacaagt cacttctcga | 840 |
| cgctaatttt gagccaggaa agaagaactt tctgcatttg acagataaag atggtgaaca | 900 |
| acctcaaata ctgctggagg attccagtgc tggggaagac agtgttcatg acaggtttat | 960 |
| aggtccgctt ccaagagaag gttctggggg ttctaccagt gattatgtca gccaaagcta | 1020 |
| ctcctactca tctattttga ataaatcaga aactggatat gtgggactag taaaccaagc | 1080 |
| aatgacttgc tatttgaata gccttttgca aacacttttt atgactcctg aatttaggaa | 1140 |
| tgcattatat aagtgggaat ttgaagaatc tgaagaagat ccagtgacaa gtattccata | 1200 |
| ccaacttcaa aggcttttttg ttttgttaca aaccagcaaa aagagagcaa ttgaaaccac | 1260 |
| agatgttaca aggagctttg gatgggatag tagtgaggct tggcagcagc atgatgtaca | 1320 |
| agaactatgc agagtcatgt ttgatgcttt ggaacagaaa tggaagcaaa cagaacaggc | 1380 |
| tgatcttata aatgagctat atcaaggcaa gctgaaggac tacgtgagat gtctggaatg | 1440 |
| tggttatgag ggctggcgaa tcgacacata tcttgatatt ccattggtca tccgacctta | 1500 |
| tgggtccagc caagcatttg ctagtgtgga agaagcattg catgcattta ttcagccaga | 1560 |
| gattctggat ggcccaaatc agtattttttg tgaacgttgt aagaagaagt gtgatgcacg | 1620 |
| gaagggcctt cggttttttgc attttccttta tctgctgacc ttacagctga aaagattcga | 1680 |
| ttttgattat acaaccatgc ataggattaa actgaatgat cgaatgacat ttcccgagga | 1740 |
| actagatatg agtactttta ttgatgttga agatgagaaa tctcctcaga ctgaaagttg | 1800 |
| cactgacagt ggagcagaaa atgaaggtag ttgtcacagt gatcagatga gcaacgattt | 1860 |
| ctccaatgat gatggtgttg atgaaggaat ctgtcttgaa accaatagtg gaactgaaaa | 1920 |
| gatctcaaaa tctggacttg aaaagaattc cttgatctat gaactttttct ctgttatggt | 1980 |

```
tcattctggg agcgctgctg gtggtcatta ttatgcatgt ataaagtcat tcagtgatga    2040
gcagtggtac agcttcaatg atcaacatgt cagcaggata acacaagagg acattaagaa    2100
aacacatggt ggatcttcag gaagcagagg atattattct agtgctttcg caagttccac    2160
aaatgcatat atgctgatct atagactgaa ggatccagcc agaaatgcaa aatttctaga    2220
agtggatgaa tacccagaac atattaaaaa cttggtgcag aaagagagag agttggaaga    2280
acaagaaaag agacaacgag aaattgagcg caatacatgc aagataaaat tattctgttt    2340
gcatcctaca aaacaagtaa tgatggaaaa taaattggag gttcataagg ataagacatt    2400
aaaggaagca gtagaaatgg cttataagat gatggattta aagaggtaa taccccctgga    2460 ttgctgtcgc cttgttaaat atgatgagtt tcatgattat ctagaacggt catatgaagg    2520
agaagaagat acaccaatgg ggcttctact aggtggcgtc aagtcaacat atatgtttga    2580
tctgctgttg gagacgagaa agcctgatca ggttttccaa tcttataaac ctggagaagt    2640
gatggtgaaa gttcatgttg ttgatctaaa ggcagaatct gtagctgctc ctataactgt    2700
tcgtgcttac ttaaatcaga cagttacaga attcaaacaa ctgatttcaa aggccatcca    2760
tttacctgct gaaacaatga gaatagtgct ggaacgctgc tacaatgatt tgcgtcttct    2820
cagtgtctcc agtaaaaccc tgaaagctga aggatttttt agaagtaaca aggtgtttgt    2880
tgaaagctcc gagactttgg attaccagat ggcctttgca gactctcatt tatggaaact    2940
cctggatcgg catgcaaata caatcagatt atttgttttg ctacctgaac aatccccagt    3000
atcttattcc aaaaggacag cataccagaa agctggaggc gattctggta atgtggatga    3060
tgactgtgaa agagtcaaag gacctgtagg aagcctaaag tctgtggaag ctattctaga    3120
agaaagcact gaaaaactca aaagcttgtc actgcagcaa cagcaggatg gagataatgg    3180
ggacagcagc aaaagtactg agacaagtga ctttgaaaac atcgaatcac ctctcaatga    3240
gagggactct tcagcatcag tggataatag agaacttgaa cagcatattc agacttctga    3300
tccagaaaat tttcagtctg aagaacgatc agactcagat gtgaataatg acaggagtac    3360
aagttcagtg gacagtgata ttcttagctc cagtcatagc agtgatactt tgtgcaatgc    3420
agacaatgct cagatcccctt tggctaatgg acttgactct cacagtatca caagtagtag    3480
aagaacgaaa gcaatgaag ggaaaaaaga acatgggat acagcagaag aagactctgg    3540
aactgatagt gaatatgatg agagtggcaa gagtagggga gaaatgcagt acatgtattt    3600
caaagctgaa ccttatgctg cagatgaagg ttctggggaa ggacataaat ggttgatggt    3660
gcatgttgat aaaagaatta ctctggcagc tttcaaacaa catttagagc cctttgttgg    3720
agttttgtcc tctcacttca aggtctttcg agtgtatgcc agcaatcaag gtttgagag    3780 cgtccggctg aatgagacac tttcatcatt ttctgatgac aataagatta caattagact    3840
ggggagagca cttaaaaaag gagaatacag agttaaagta taccagcttt tggtcaatga    3900
acaagagcca tgcaagtttc tgctagatgc tgtgtttgct aaaggaatga ctgtacggca    3960
atcaaaagag gaattaattc ctcagctcag ggagcaatgt ggtttagagc tcagtattga    4020
caggtttcgt ctaaggaaaa aaacatgaa gaatcctggc actgtctttt tggattatca    4080
tatttatgaa gaagatatta atatttccag caactgggag gttttccttg aagttcttga    4140 tgggtagag aagatgaagt ccatgtcaca gcttgcagtt ttgtcaagac ggtggaagcc    4200
ttcagagatg aagttggatc ccttccagga ggttgtattg gaaagcagta gtgtggacga    4260
attgcgagag aagcttagtg aaatcagtgg gattcctttg gatgatatttg aatttgctaa    4320 gggtagagga acatttcccct gtgatatttc tgtccttgat attcatcagg atttagactg    4380
```

```
gaatcctaaa gtttctaccc tgaatgtctg gcctctttat atctgtgatg atggtgcggt    4440
catattttat agggataaaa cagaagaatt aatggaattg acagatgagc aaagaaatga    4500
actgatgaaa aagaaagca gtcgactcca gaagactgga catcgtgtaa catactcacc    4560
tcgtaaagag aaagcactaa aaatatatct ggatggagca ccaaataaag atctgactca    4620
agactgactc tgatagtgta gcattttccc tgggggagtt ttggttttaa ttagatggtt    4680
cactaccact gggtagtgcc attttggccg acatggttg gggtaaccca gtgacaccag     4740
cactgattgg actgccctac accaatcaga agctcagtgc ccaatgggcc actgttttga    4800
ctcggaatca tgttgtgcac tatagtcaaa tgtactgtaa agtgaaaagg gatgtgcaaa    4860
aaaataaaaa aaacaacaa aaaaagctaa ccttctatta gaaaggggga caggggaatg     4920
agtaaacttc ttttattgcg acaaatgtg cacatagccg ctagtaaaac tagcctcaaa     4980
caggatgctc atagcttaat aataaaagct gtgcaaaggc catgaatgaa tgaattttct    5040
gtttatttca ctgatgcaca cattacctca ttgacaattc agaagtaaat ccaacgtgtg    5100
ttgactcttg gaaagcagca aaaacaggag ctgaagaaaa gaaattcttg gaaccagccg    5160
taacccagta aggaattgtg aagttgtgtt tttattttgt ttcattttt gcagagtatt     5220 aagaacatta ttctggaaca tcagaacgtt tcccttagac cgatcccagc aggtggcagc    5280
tcagattgct gcagtgttgt aattataact gattgtactt aagttatgga tgtagagaat    5340
atgtttcatt catttattca gcatgtaaat aaaattgatc ctgttgagtt atcataattg    5400
cagttcaact atctgccatg attattcttt tcacgtatca ttcattctgt catttgtgt     5460 acattgagaa gtatagcaat ctatgtaaat gtaatcctca gtgaggttcc tcagtgctag    5520
gtcccatagg attgtcgttg cccttgttaa tgaggtttct ctgttcagcg gcttcaattt    5580
ttttctcttt gtacatctag ttttgaagat ttacttcaag tttgaatctt ctagaatgct    5640
tgtaagtcca gttttaattt ttagagtcaa tttgtagtta catgtagttt aacttttggg    5700
aaacgtctta acattgttct gaataaactt gctaatgagg tcaggtcatg gtacagactg    5760
atgcagtcaa catgatttca ttgcagagtt tattagtatc agcaagtttt tgctttgcta    5820
aataaaagta ctcaatgaac acaattctac ataaattttg acataccatc taatttataa    5880
aaatcaataa aaaggtttt ggtaaaactt tttcatgcca gatgctgttt acaacaatga     5940
acatgccaat aaaacatttg ttcattctgt tgtgttattt tagtcattaa acttctgtgg    6000
atgaagaatc tgggttaaga atagatttgt catctttaaa tatgacattt tgtaatgtgt    6060
attggatatc tcatttctat gataaaggta tatttacagt aaagttctca taagagaaat    6120
gaaaagctgt gttaatatct aactttgggg aaccctgtca gtatttcaga tccgattttt    6180 acccttttt tcttataaga aagataaaat tagaaaatac tgttagcaaa tgtggctctg    6240
ccatttgaat ataatcaccg agaattccat gtcttaaaag tctcctggaa tccacaatga    6300 aaaaaaaat cttttctaag gtattttct ggctaatttt tatttgaaga aagctatagc     6360
atttagcgaa atttgactga agtaatgttc tgagtttgca ttagtgggat tggtgatgtt    6420
ctcagaagaa aattggaaac acttgtgatg aattgtcttt cagatcactt agattttctg    6480
atgtaagagg acagctgttt ggttctgata caggcctgct tacttgggat gtagggttag    6540
taaatggggt ttctgcttta aaggactgac ttgctatcac acaaaagagg cagacttgta    6600
aacacaatgg gctttggagt ttggtctgat tgggtttggt ttagtattcc tatgagcgta    6660
aatggtaaaa ttcttctgat acccactctt tagactgtgc cttctgctct gttctttgtt    6720
ttatgtttaa ctgctgtttc taattgcagg tgtattacag atacaaataa gagtaaagaa    6780
```

```
aatatatttc attatagaaa agaaaaaatt aaaagcttct tgcttttcag tgcctgatag    6840
agtgaaaaca caaagttgca ctttaataat ttcaataaaa gctaatctgt gtcagcctcc    6900
ctctgcttca gagagtcagg tgagcatcca taacctaaca ggcagagccc tagcgatgtg    6960
gatcaagttt cctgagcccg ggggcggtgg agcctcatga tctcttatct tttgaggctg    7020
aggcaggtca catgcaacaa attgtgaccc tgctccccac aagtcatgca aaggttttga    7080
agagctttta ccgtggggca gatgaacttg tgtcaaccat gcacaccctg tgagaaccaa    7140
gtacctgtgt ttctaaggcg ggcactcaag gtgaggggtg cattctggcc aaagaaacaa    7200
aagctgtggt ttcaggacca tgccgtgtgt agctgatctg tacgggacgt gtatgtaagg    7260
aagagcaatc atgatagata agaacagtgt gtgaagcagc cttcacacta gagtgtttgg    7320
tcatctctta taatgtaagg gaaggtactt taaaattctg ggaagatgcg atgaactcat    7380
gtcccagtca gaaaataatc caatgaaata agcattggtt gccaggccac agttaggaat    7440
tgtattgtga tacatctaga ggccaagaga gcaggagaga gctaccaact tacactgtgg    7500
tttaagctaa atgaccgcac agcatcatag cattgcagtg ttgttactaa atctggaagt    7560
gacctgtgaa tgtatggaat acaataaagt cttttattct ggttcatttg ctagtacttc    7620 cttttgatt ggatactgta gttcttcctc tggatttat tttgttcagc gtcaaggccc     7680
taattttgca aatgtagtct aaaccacatt acgtggacta gaggatactc tgaattagca    7740
agttttttgt ttgctgaata aaactattcc atcttaa                              7777

<210> SEQ ID NO 31
<211> LENGTH: 19
<212> TYPE: DNA
<213> ORGANISM: Artificial Sequence
<220> FEATURE:
<223> OTHER INFORMATION: USP47 shRNA V2HS_174637

<400> SEQUENCE: 31
gaatctgtct tgaaaccaa                                                   19

<210> SEQ ID NO 32
<211> LENGTH: 19
<212> TYPE: DNA
<213> ORGANISM: Artificial Sequence
<220> FEATURE:
<223> OTHER INFORMATION: USP47 shRNA V2HS_174639

<400> SEQUENCE: 32
cgcaatacat gcaagataa                                                   19

<210> SEQ ID NO 33
<211> LENGTH: 19
<212> TYPE: DNA
<213> ORGANISM: Artificial Sequence
<220> FEATURE:
<223> OTHER INFORMATION: USP47 shRNAV2HS_174641

<400> SEQUENCE: 33
ggattccttt ggatgatat                                                   19

<210> SEQ ID NO 34
<211> LENGTH: 19
<212> TYPE: DNA
<213> ORGANISM: Artificial Sequence
<220> FEATURE:
<223> OTHER INFORMATION: USP47 shRNA V2HS_174642

<400> SEQUENCE: 34
```

```
gatttagact ggaatccta                                              19

<210> SEQ ID NO 35
<211> LENGTH: 19
<212> TYPE: DNA
<213> ORGANISM: Artificial Sequence
<220> FEATURE:
<223> OTHER INFORMATION: USP47 shRNA V2HS_218228

<400> SEQUENCE: 35
caatgacttg ctatttgaa                                              19

<210> SEQ ID NO 36
<211> LENGTH: 19
<212> TYPE: RNA
<213> ORGANISM: Artificial Sequence
<220> FEATURE:
<223> OTHER INFORMATION: USP47 siRNA J-006093-05

<400> SEQUENCE: 36
gcaacgauuu cuccaauga                                              19

<210> SEQ ID NO 37
<211> LENGTH: 19
<212> TYPE: RNA
<213> ORGANISM: Artificial Sequence
<220> FEATURE:
<223> OTHER INFORMATION: USP47 siRNA J-006093-06

<400> SEQUENCE: 37
caacauguca gcaggauaa                                              19

<210> SEQ ID NO 38
<211> LENGTH: 19
<212> TYPE: RNA
<213> ORGANISM: Artificial Sequence
<220> FEATURE:
<223> OTHER INFORMATION: USP47 siRNA J-006093-07

<400> SEQUENCE: 38
gcugucgccu uguuaaaua                                              19

<210> SEQ ID NO 39
<211> LENGTH: 19
<212> TYPE: RNA
<213> ORGANISM: Artificial Sequence
<220> FEATURE:
<223> OTHER INFORMATION: USP47 siRNA J-006093-08

<400> SEQUENCE: 39
cgcaauacau gcaagauaa                                              19

<210> SEQ ID NO 40
<211> LENGTH: 19
<212> TYPE: DNA
<213> ORGANISM: Artificial Sequence
<220> FEATURE:
<223> OTHER INFORMATION: USP47 shRNA V2HS-174640

<400> SEQUENCE: 40
cttataagat gatggattt                                              19

<210> SEQ ID NO 41
<211> LENGTH: 19
<212> TYPE: DNA
<213> ORGANISM: Artificial Sequence
<220> FEATURE:
```

<223> OTHER INFORMATION: MX1 shRNA V2HS_152026

<400> SEQUENCE: 41
ctcatcacac atatctgta					19

<210> SEQ ID NO 42
<211> LENGTH: 19
<212> TYPE: DNA
<213> ORGANISM: Artificial Sequence
<220> FEATURE:
<223> OTHER INFORMATION: MX1 shRNA V2HS_152028

<400> SEQUENCE: 42
ctgccaggct ttgtgaatt					19

<210> SEQ ID NO 43
<211> LENGTH: 19
<212> TYPE: DNA
<213> ORGANISM: Artificial Sequence
<220> FEATURE:
<223> OTHER INFORMATION: MALT1 shRNA V2HS_84222

<400> SEQUENCE: 43
ccaatattgt gtttggata					19

<210> SEQ ID NO 44
<211> LENGTH: 19
<212> TYPE: DNA
<213> ORGANISM: Artificial Sequence
<220> FEATURE:
<223> OTHER INFORMATION: RPS25 shRNA V2HS_93855

<400> SEQUENCE: 44
cttagtaaag gacttatca					19

<210> SEQ ID NO 45
<211> LENGTH: 19
<212> TYPE: DNA
<213> ORGANISM: Artificial Sequence
<220> FEATURE:
<223> OTHER INFORMATION: SH3BP4 shRNA V2HS_260346

<400> SEQUENCE: 45
ctttctattt gttaagtat					19

<210> SEQ ID NO 46
<211> LENGTH: 2611
<212> TYPE: DNA
<213> ORGANISM: Homo sapiens

<400> SEQUENCE: 46
gtcgcacacc accaccttcc tgccctggct gtccatcgtc cgcccaggga agagccgctg		60 cagccgcaca acctacagcc accgccgccc ggccgttttc tcttcttcct cttgcgtctt		120 cccggcccct ccttcggccc aacttttttc ccccgaccgg aagccgccgc cgggctccgc		180 ccgtcattta gctgaatgcc tgcacgaaaa gggtgggacg ggcaggcagc gcgactggca		240 gcggtgagct ccaataaaag atggaggagc gtcgaggccc ctcccgcagc tccgcttccg		300 gctcggctgt cacggtcgct gcccaccccgg gttcttcgct gcttctagtt ccgggcgctt		360 tgccgggcgt taatggcggc caacatcgcc ggtgctgcgg cttttctccct aaagtgtcac		420 aggagctaag ggcgctgctt aacgaactgc agaagacgca ggcaggtgaa ggacaccggt		480 tctgctgcgg cagtggaatg tggcggagaa gctggcgggt agggcgggga gcaagcctgg		540

-continued

```
aggtcctggc ggaccccacc attcgacagg gcttggtgtg ttattgcttc taggccttt     600
cagcggacag aactgggatg gatacacaca tgcttatttg aaatcatgcg tttgttccat     660
actccaatgt cagcccaccc cttctttgcc caagttgctc tatggtcaag tgagcgagag     720
caggtgcctg catttccagc ctcgtggctc accgcctcct tccagtagtc ccatgttgct     780
tcacacctct taagtacatg tacttctgtg aacccagagc cttggctttg aaatcagaca     840
accccagttt caaacgtggc gctgccactc acgagttttg tgattttggc ataccccgt     900
ctgcatgggg ataataactt ctatctccat aggtgtggtg aggataaaag tctatgcatg     960
gaggaaatgt tcattcagtg gtagctattt ctaattctgt tcttctggac ctatgattct    1020
atctacgatg cctcattttt tttccttttt aatcaattgg caaacttgtg ctctgagacc    1080
cagcttgtta catctctgat gacagctgat atcctcagga tattccgtac ttcctttctc    1140
cctattactt tactatgaat atatgaataa cattgtgctt attgcatgca acaaatattt    1200
attagatgaa tgacattaaa attcacctt aaaatgccat cctttatgag aggtgagaaa     1260
tagaactttt ccttcgacat ggctgtacat gttcaacaac tagaataaaa cagtcatcat    1320
gaaccctcaa tccagtattc tttttataat atagctgcct gtcagttttc actgttcttt    1380
tattagacca gtgattttca aaccttttta aaggcataca gtgctttatt caaatctaat    1440
cttatatgga accctcaaca cataaatatt aagataaaaa taaagctgcc attgttgcaa    1500
ttagaagttt gagaggttag aataggtagg aagtctcgga ggaacatttc ttcgttttac    1560
ctgctttaac agtcagagaa gtacctcagc cagcagaaaa atttatttgt tcataaattc    1620
cttgagtata gagtccgtat cttattttg tggcctccaa tgctagtgct gtgcagtttt    1680
cttgaaagtg catttattg gtctcagcaa attgaactca agcatttctg tgttctttta    1740
cttttcctct tgtggaatt aaggggattg ctaatttgta tttttaaaga aagaacatta    1800
ttccgggcgc ggtggctcac gcctgtaatc ccagcacttg gggaggccaa ggagggcaaa    1860
tcacctgaga tcaggagttc aagacaaggc tgaccaacat ggcaaaaccc cgtctctact    1920
aaaaatacaa aaattagctg ggcgtgttgg cacgcgcctg taatcccagc cactcaggaa    1980
gctgaggcag gagaatcgct tgaacccggg aagcagaggt tgcagtgaca gagatcgtgc    2040
cactgcactc cagcctggtg agagcaagac tctgtctcaa aaaaaaaaaa aaaaaattgg    2100
caagtttggc cctaaaattt atatgaaatg aaaaggaacc agaataaaag gatttcgaaa    2160
cagaaaaaga tggagaactt ccactacctg aattcaaaac ttattataaa gctacagtaa    2220
tgaagactgt aatactggca tagaggcaga tatatcgatc aatggaatca aatagtccac    2280
aaataaacct ttacattatg gtcagttgat tttcaacaat ggtgctaaaa caatccatgg    2340
ggaaagggta atcttttcaa tgaatgatgt gggagggaaa aaaagaact ttgattctta    2400
cctcacatca cacataaaaa ttgatttaag tggatcatag acctaaatat aaaagctaaa    2460
actataaatt tcagaagaaa aagaggaaaa tcttttgata ttaagttaag caaagtttgc    2520
ttagatatga cgctaaaatc gtgatctata aaagaaaaaa ttgatagttg acataataga    2580
aatttaaagc ttttagttca tgtattgaaa c                                   2611
```

<210> SEQ ID NO 47
<211> LENGTH: 19
<212> TYPE: DNA
<213> ORGANISM: Artificial Sequence
<220> FEATURE:
<223> OTHER INFORMATION: HCG 1986447 shRNA V2HS_29650

<400> SEQUENCE: 47
gtgctttatt caaatctaa                                      19

<210> SEQ ID NO 48
<211> LENGTH: 19
<212> TYPE: DNA
<213> ORGANISM: Artificial Sequence
<220> FEATURE:
<223> OTHER INFORMATION: WNK2 shRNA V2HS_238923

<400> SEQUENCE: 48
gtctgagaga gtgacctat                                      19

<210> SEQ ID NO 49
<211> LENGTH: 19
<212> TYPE: DNA
<213> ORGANISM: Artificial Sequence
<220> FEATURE:
<223> OTHER INFORMATION: TMC6 shRNA V2HS_198493

<400> SEQUENCE: 49
gggactctat ttattctga                                      19

<210> SEQ ID NO 50
<211> LENGTH: 19
<212> TYPE: DNA
<213> ORGANISM: Artificial Sequence
<220> FEATURE:
<223> OTHER INFORMATION: CFL1 shRNA V2HS_64314

<400> SEQUENCE: 50
ccctctatga tgcaaccta                                      19

<210> SEQ ID NO 51
<211> LENGTH: 19
<212> TYPE: DNA
<213> ORGANISM: Artificial Sequence
<220> FEATURE:
<223> OTHER INFORMATION: ABI2 shRNA V2HS_196634

<400> SEQUENCE: 51
accagttcgt tatattaga                                      19

<210> SEQ ID NO 52
<211> LENGTH: 19
<212> TYPE: DNA
<213> ORGANISM: Artificial Sequence
<220> FEATURE:
<223> OTHER INFORMATION: ARRDC3 shRNA V2HS_217697

<400> SEQUENCE: 52
ggccttggct actaccagt                                      19

<210> SEQ ID NO 53
<211> LENGTH: 19
<212> TYPE: DNA
<213> ORGANISM: Artificial Sequence
<220> FEATURE:
<223> OTHER INFORMATION: BRCA1 shRNA V2HS_254648

<400> SEQUENCE: 53
cacaaagtgt gaccacata                                      19

<210> SEQ ID NO 54
<211> LENGTH: 19
<212> TYPE: DNA
<213> ORGANISM: Artificial Sequence
<220> FEATURE:

```
<223> OTHER INFORMATION: BRCA1 shRNA V2HS_280394

<400> SEQUENCE: 54
gatcgattat gtgacttaa                                              19

<210> SEQ ID NO 55
<211> LENGTH: 19
<212> TYPE: DNA
<213> ORGANISM: Artificial Sequence
<220> FEATURE:
<223> OTHER INFORMATION: BRCA1 shRNA V2HS_255064

<400> SEQUENCE: 55
ccctttcacc catacacat                                              19

<210> SEQ ID NO 56
<211> LENGTH: 19
<212> TYPE: DNA
<213> ORGANISM: Artificial Sequence
<220> FEATURE:
<223> OTHER INFORMATION: C17orf85 shRNA V2HS_176062

<400> SEQUENCE: 56
ccgatactcg ggagaagaa                                              19

<210> SEQ ID NO 57
<211> LENGTH: 19
<212> TYPE: DNA
<213> ORGANISM: Artificial Sequence
<220> FEATURE:
<223> OTHER INFORMATION: C1orf 71 shRNA V2HS_44617

<400> SEQUENCE: 57
cggaggaact ctgttagaa                                              19

<210> SEQ ID NO 58
<211> LENGTH: 19
<212> TYPE: DNA
<213> ORGANISM: Artificial Sequence
<220> FEATURE:
<223> OTHER INFORMATION: C6orf162 shRNA V2HS_35766

<400> SEQUENCE: 58
gtgttcttat agttattta                                              19

<210> SEQ ID NO 59
<211> LENGTH: 19
<212> TYPE: DNA
<213> ORGANISM: Artificial Sequence
<220> FEATURE:
<223> OTHER INFORMATION: CCNJL shRNA V2HS_136349

<400> SEQUENCE: 59
ctcagcacgt gtattgaaa                                              19

<210> SEQ ID NO 60
<211> LENGTH: 19
<212> TYPE: DNA
<213> ORGANISM: Artificial Sequence
<220> FEATURE:
<223> OTHER INFORMATION: GON4L shRNA V2HS_138350

<400> SEQUENCE: 60
caggtgagag ctggagaat                                              19

<210> SEQ ID NO 61
```

```
<211> LENGTH: 19
<212> TYPE: DNA
<213> ORGANISM: Artificial Sequence
<220> FEATURE:
<223> OTHER INFORMATION: HIST1H2AB shRNA V2HS_33954

<400> SEQUENCE: 61
catcataagg ccaagggaa                                                  19

<210> SEQ ID NO 62
<211> LENGTH: 19
<212> TYPE: DNA
<213> ORGANISM: Artificial Sequence
<220> FEATURE:
<223> OTHER INFORMATION: HPS4 shRNA V2HS_70495

<400> SEQUENCE: 62
gcctatccgt gtatatgga                                                  19

<210> SEQ ID NO 63
<211> LENGTH: 19
<212> TYPE: DNA
<213> ORGANISM: Artificial Sequence
<220> FEATURE:
<223> OTHER INFORMATION: LHX8 shRNA V2HS_75780

<400> SEQUENCE: 63
accattctga gtttattaa                                                  19

<210> SEQ ID NO 64
<211> LENGTH: 19
<212> TYPE: DNA
<213> ORGANISM: Artificial Sequence
<220> FEATURE:
<223> OTHER INFORMATION: RPL23 shRNA V2HS_23046

<400> SEQUENCE: 64
ggaccagtag caaaggagt                                                  19

<210> SEQ ID NO 65
<211> LENGTH: 19
<212> TYPE: DNA
<213> ORGANISM: Artificial Sequence
<220> FEATURE:
<223> OTHER INFORMATION: RPL32 shRNA V2HS_165267

<400> SEQUENCE: 65
ctgagattgc tcacaatgt                                                  19

<210> SEQ ID NO 66
<211> LENGTH: 953
<212> TYPE: DNA
<213> ORGANISM: Homo sapiens

<400> SEQUENCE: 66 tgagggtgg  agggcagagg  agaaactgcg  tcaggatgt   gtccgccacc  ttcatcctcc    60
agacgggact  tggagcggc   tgcaggaaac  cctgagagat  tcctctttag  ggaagtcatc   120
cagccctggg  gtcccttat   gccgggagca  gtgaggacag  aagaatgacc  atctatcttg   180
ctgaaagctc  tgtgagggag  gaacggaaga  acgagggag   ctacgacctt  gaccatcccc   240
tgagtgtcca  tggcctctgt  gctccggatg  atgccgggc   tgccagggac  cacagagcca   300
cccactggga  ggctgggggt  tggcctggct  caggggcgtt  cgtcagccat  agacacccac   360
agcatgtggt  gggcagggct  gggaggtgac  acaggaactg  aaaaacctga  gaagctccag   420
```

```
ccactccgca gggtaagtgc cacctgggg t aaaatgatta gctggttcca gcccctccgc    480
agggtaagtg gcacctgggg taaaatgact gcctggagct ggcagctgct ttctctgctc    540
tccccagggc cctgcaggga agcgtggaaa ggcggcacag ggctggaccc agaggagctc    600
tcagatgctg gactggactg tttcagggt catctagccc attccccgcc tccaggcgag     660
gatttgcttg agcctggaaa gatgaaggat cctcccagtg ccgtcaagcc ccggattcca    720
cctccctgta ggtggactgc cagcgcaggc cctgacaacg cagagaaaga cacaggaccc    780
agctgggcca gtgacagcag gagctcctgg tgccacaggt gagggtgggg acgcctggag    840
caccatgggg gtcctggttt agtctacagc agggtcttaa aataggatgt aagtgttaca    900
tcttgacaca gtgtacacat gctgacacat attaaaacaa attttacaca gca           953
```

```
<210> SEQ ID NO 67
<211> LENGTH: 19
<212> TYPE: DNA
<213> ORGANISM: Artificial Sequence
<220> FEATURE:
<223> OTHER INFORMATION: LOC730139 shRNA V2HS_25169

<400> SEQUENCE: 67
ggatgtaagt gttacatct                                                  19

<210> SEQ ID NO 68
<211> LENGTH: 19
<212> TYPE: DNA
<213> ORGANISM: Artificial Sequence
<220> FEATURE:
<223> OTHER INFORMATION: LOC730139 shRNA V2HS_25168

<400> SEQUENCE: 68
gtgtacacat gctgacaca                                                  19

<210> SEQ ID NO 69
<211> LENGTH: 19
<212> TYPE: DNA
<213> ORGANISM: Artificial Sequence
<220> FEATURE:
<223> OTHER INFORMATION: LRRC39 shRNA V2HS_18852

<400> SEQUENCE: 69
gaattatttg gccttcagt                                                  19

<210> SEQ ID NO 70
<211> LENGTH: 19
<212> TYPE: DNA
<213> ORGANISM: Artificial Sequence
<220> FEATURE:
<223> OTHER INFORMATION: LRRC39 shRNA V2HS_18851

<400> SEQUENCE: 70
accttgatct gagtatgaa                                                  19

<210> SEQ ID NO 71
<211> LENGTH: 19
<212> TYPE: DNA
<213> ORGANISM: Artificial Sequence
<220> FEATURE:
<223> OTHER INFORMATION: NRG1 shRNA V2HS_84939

<400> SEQUENCE: 71
atgtgttatt tgtcacaaa                                                  19

<210> SEQ ID NO 72
```

```
<211> LENGTH: 19
<212> TYPE: DNA
<213> ORGANISM: Artificial Sequence
<220> FEATURE:
<223> OTHER INFORMATION: OR52A1 shRNA V2HS_244561

<400> SEQUENCE: 72
gctaggttta aagcattca                                              19

<210> SEQ ID NO 73
<211> LENGTH: 19
<212> TYPE: DNA
<213> ORGANISM: Artificial Sequence
<220> FEATURE:
<223> OTHER INFORMATION: OR52A1 shRNA V2HS_49243

<400> SEQUENCE: 73
cttggaatat tctggttta                                              19

<210> SEQ ID NO 74
<211> LENGTH: 19
<212> TYPE: DNA
<213> ORGANISM: Artificial Sequence
<220> FEATURE:
<223> OTHER INFORMATION: PLEKHH1 shRNA V2HS_46786

<400> SEQUENCE: 74
ctctggattt agagatata                                              19

<210> SEQ ID NO 75
<211> LENGTH: 19
<212> TYPE: DNA
<213> ORGANISM: Artificial Sequence
<220> FEATURE:
<223> OTHER INFORMATION: PTPN13 shRNA V2HS_57273

<400> SEQUENCE: 75
cagtgaaagt ccatctatt                                              19

<210> SEQ ID NO 76
<211> LENGTH: 19
<212> TYPE: DNA
<213> ORGANISM: Artificial Sequence
<220> FEATURE:
<223> OTHER INFORMATION: PTPRJ shRNA V2HS_91546

<400> SEQUENCE: 76
ctaattgact ccactggat                                              19

<210> SEQ ID NO 77
<211> LENGTH: 19
<212> TYPE: DNA
<213> ORGANISM: Artificial Sequence
<220> FEATURE:
<223> OTHER INFORMATION: PTPRJ shRNA V2HS_171000

<400> SEQUENCE: 77
ggaagtcacg tatttgaat                                              19

<210> SEQ ID NO 78
<211> LENGTH: 19
<212> TYPE: DNA
<213> ORGANISM: Artificial Sequence
<220> FEATURE:
<223> OTHER INFORMATION: RLN1 shRNA V2HS_94799

<400> SEQUENCE: 78
```

-continued caatcttagc tttgaagaa                                           19

<210> SEQ ID NO 79
<211> LENGTH: 19
<212> TYPE: DNA
<213> ORGANISM: Artificial Sequence
<220> FEATURE:
<223> OTHER INFORMATION: RNF19A shRNA V2HS_96523

<400> SEQUENCE: 79
gttcttcatc cattagtta                                           19

<210> SEQ ID NO 80
<211> LENGTH: 19
<212> TYPE: DNA
<213> ORGANISM: Artificial Sequence
<220> FEATURE:
<223> OTHER INFORMATION: SLC7A14 shRNA V2HS_57109

<400> SEQUENCE: 80
gtgttgacaa tatattgat                                           19

<210> SEQ ID NO 81
<211> LENGTH: 19
<212> TYPE: DNA
<213> ORGANISM: Artificial Sequence
<220> FEATURE:
<223> OTHER INFORMATION: ST8SIA3 shRNA V2HS_114878

<400> SEQUENCE: 81
ctgagcacag gtattctta                                           19

<210> SEQ ID NO 82
<211> LENGTH: 19
<212> TYPE: DNA
<213> ORGANISM: Artificial Sequence
<220> FEATURE:
<223> OTHER INFORMATION: ST8SIA3 shRNA V2HS_114879

<400> SEQUENCE: 82
ggaagatctt ccataccat                                           19

<210> SEQ ID NO 83
<211> LENGTH: 19
<212> TYPE: DNA
<213> ORGANISM: Artificial Sequence
<220> FEATURE:
<223> OTHER INFORMATION: STX3 shRNA V2HS_33937

<400> SEQUENCE: 83
cccagaaact gcaatgtat                                           19

<210> SEQ ID NO 84
<211> LENGTH: 19
<212> TYPE: DNA
<213> ORGANISM: Artificial Sequence
<220> FEATURE:
<223> OTHER INFORMATION: TMTC4 shRNA V2HS_177667

<400> SEQUENCE: 84
ctttattcct caaggcaat                                           19

<210> SEQ ID NO 85
<211> LENGTH: 19
<212> TYPE: DNA
<213> ORGANISM: Artificial Sequence
<220> FEATURE:

<223> OTHER INFORMATION: TMTC4 shRNA V2HS_275500

<400> SEQUENCE: 85
catgaataat cttggaaat					19

<210> SEQ ID NO 86
<211> LENGTH: 19
<212> TYPE: DNA
<213> ORGANISM: Artificial Sequence
<220> FEATURE:
<223> OTHER INFORMATION: TTN shRNA V2HS_171633

<400> SEQUENCE: 86
gttcccgact tgaaatgaa					19

<210> SEQ ID NO 87
<211> LENGTH: 19
<212> TYPE: DNA
<213> ORGANISM: Artificial Sequence
<220> FEATURE:
<223> OTHER INFORMATION: TTN shRNA V2HS_171637

<400> SEQUENCE: 87
ccatctcggt tctttagaa					19

<210> SEQ ID NO 88
<211> LENGTH: 19
<212> TYPE: DNA
<213> ORGANISM: Artificial Sequence
<220> FEATURE:
<223> OTHER INFORMATION: UBXN7 shRNA V2HS_130208

<400> SEQUENCE: 88
cattatttgg tgctcctaa					19

<210> SEQ ID NO 89
<211> LENGTH: 19
<212> TYPE: DNA
<213> ORGANISM: Artificial Sequence
<220> FEATURE:
<223> OTHER INFORMATION: YPEL2 shRNA V2HS_77698

<400> SEQUENCE: 89
ctctttaact cagtagtta					19

<210> SEQ ID NO 90
<211> LENGTH: 19
<212> TYPE: DNA
<213> ORGANISM: Artificial Sequence
<220> FEATURE:
<223> OTHER INFORMATION: YPEL2  shRNA V2HS_77701

<400> SEQUENCE: 90
caaggacgag catacctct					19

<210> SEQ ID NO 91
<211> LENGTH: 19
<212> TYPE: DNA
<213> ORGANISM: Artificial Sequence
<220> FEATURE:
<223> OTHER INFORMATION: ZNF251 shRNA V2HS_250202

<400> SEQUENCE: 91
gaccaagaag gaactatct					19

<210> SEQ ID NO 92

```
<211> LENGTH: 19
<212> TYPE: DNA
<213> ORGANISM: Artificial Sequence
<220> FEATURE:
<223> OTHER INFORMATION: ZNF251 shRNA V2HS_215547

<400> SEQUENCE: 92
aatattactg gcaaagtaa                                                  19

<210> SEQ ID NO 93
<211> LENGTH: 19
<212> TYPE: DNA
<213> ORGANISM: Artificial Sequence
<220> FEATURE:
<223> OTHER INFORMATION: MERTK shRNA V2HS_1643

<400> SEQUENCE: 93
ctgcatactt acttacttt                                                  19

<210> SEQ ID NO 94
<211> LENGTH: 19
<212> TYPE: DNA
<213> ORGANISM: Artificial Sequence
<220> FEATURE:
<223> OTHER INFORMATION: MERTK shRNA V2HS_168768

<400> SEQUENCE: 94
cagacgttat ttaccgtca                                                  19

<210> SEQ ID NO 95
<211> LENGTH: 19
<212> TYPE: DNA
<213> ORGANISM: Artificial Sequence
<220> FEATURE:
<223> OTHER INFORMATION: MERTK shRNA V2HS_197158

<400> SEQUENCE: 95
ccttcagtga tccagtgaa                                                  19

<210> SEQ ID NO 96
<211> LENGTH: 19
<212> TYPE: DNA
<213> ORGANISM: Artificial Sequence
<220> FEATURE:
<223> OTHER INFORMATION: SCG2 shRNA V2HS_172404

<400> SEQUENCE: 96
gccaggatgc tagttaaat                                                  19

<210> SEQ ID NO 97
<211> LENGTH: 19
<212> TYPE: DNA
<213> ORGANISM: Artificial Sequence
<220> FEATURE:
<223> OTHER INFORMATION: SCG2 shRNA V2HS_172401

<400> SEQUENCE: 97
ctcttgattc tcagtctat                                                  19

<210> SEQ ID NO 98
<211> LENGTH: 19
<212> TYPE: DNA
<213> ORGANISM: Artificial Sequence
<220> FEATURE:
<223> OTHER INFORMATION: SCG2 shRNA V2HS_172400

<400> SEQUENCE: 98
```
ctcctatgta tgaagagaa                                                  19

<210> SEQ ID NO 99
<211> LENGTH: 1841
<212> TYPE: DNA
<213> ORGANISM: Homo sapiens

<400> SEQUENCE: 99

| | | | | | |
|---|---|---|---|---|---|
| atccctcggg | tcccgggatg | gggggggcggt | gaggcaggca | cagcccccg | ccccccatggc | 60 |
| cgcccgtcgg | agccagaggc | ggaggggggcg | ccgggggggag | ccgggcaccg | ccctgctggt | 120 |
| cccgctcgcg | ctgggcctgg | gcctggcgct | ggcctgcctc | ggcctcctgc | tggccgtggt | 180 |
| cagtttgggg | agccgggcat | cgctgtccgc | ccaggagcct | gcccaggagg | agctggtggc | 240 |
| agaggaggac | caggacccgt | cggaactgaa | tccccagaca | gaagaaagcc | aggatcctgc | 300 |
| gcctttcctg | aaccgactag | ttcggcctcg | cagaagtgca | cctaaaggcc | ggaaaacacg | 360 |
| ggctcgaaga | gcgatcgcag | cccattatga | agttcatcca | cgacctggac | aggacggagc | 420 |
| gcaggcaggt | gtggacggga | cagtgagtgg | ctgggaggaa | gccagaatca | acagctccag | 480 |
| ccctctgcgc | tacaaccgcc | agatcgggga | gtttatagtc | acccgggctg | ggctctacta | 540 |
| cctgtactgt | cagagttccg | atgccctgga | agcctgggag | aatggggaga | gatcccggaa | 600 |
| aaggagagca | gtgctcaccc | aaaaacagaa | gaagcagcac | tctgtcctgc | acctggttcc | 660 |
| cattaacgcc | acctccaagg | atgactccga | tgtgacagag | gtgatgtggc | aaccagctct | 720 |
| taggcgtggg | agaggcctac | aggcccaagg | atatggtgtc | cgaatccagg | atgctggagt | 780 |
| ttatctgctg | tatagccagg | tcctgtttca | agacgtgact | ttcaccatgg | gtcaggtggt | 840 |
| gtctcgagaa | ggccaaggaa | ggcaggagac | tctattccga | tgtataagaa | gtatgccctc | 900 |
| ccacccggac | cgggcctaca | acagctgcta | tagcgcaggt | gtcttccatt | tacaccaagg | 960 |
| ggatattctg | agtgtcataa | ttccccgggc | aagggcgaaa | cttaacctct | ctccacatgg | 1020 |
| aaccttcctg | gggtttgtga | aactgtgatt | gtgttataaa | aagtggctcc | cagcttggaa | 1080 |
| gaccaggggtg | ggtacatact | ggagacagcc | aagagctgag | tatataaagg | agagggaatg | 1140 |
| tgcaggaaca | gaggcgtctt | cctgggtttg | gctccccgtt | cctcactttt | ccctttcat | 1200 |
| tcccacccc | tagactttga | ttttacggat | atcttgcttc | tgttccccat | ggagctccga | 1260 |
| attcttgcgt | gtgtgtagat | gaggggcggg | ggacgggcgc | caggcattgt | ccagacctgg | 1320 |
| tcggggccca | ctggaagcat | ccagaacagc | accaccatct | agcggccgct | cgagggaagc | 1380 |
| acccgccggt | tggccgaagt | ccacgaagcc | gccctctgct | agggaaaacc | cctggttctc | 1440 |
| catgccacac | ctctctccag | gtgccctctg | cctcttcacc | ccacaagaag | ccttatccta | 1500 |
| cgtccttctc | tccatctatc | ggaccccagt | ttccatcact | atctccagag | atgtagctat | 1560 |
| tatgcgcccg | tctacagggg | gtgcccgacg | atgacggtgc | cttcgcagtc | aaattactct | 1620 |
| tcgggtccca | aggtttggct | ttcacgcgct | ccattgcccc | ggcgtggcag | gccattccaa | 1680 |
| gcccttccgg | gctggaactg | gtgtcggagg | agcctcgggt | gtatcgtacg | ccctggtgtt | 1740 |
| ggtgttgcct | cactcctctg | agctcttctt | tctgatcaag | ccctgcttaa | agttaaataa | 1800 |
| aatagaatga | atgataccccc | ggcaaaaaaa | aaaaaaaaaa | a | | 1841 |

<210> SEQ ID NO 100
<211> LENGTH: 2293
<212> TYPE: DNA
<213> ORGANISM: Homo sapiens

<400> SEQUENCE: 100

| | |
|---|---|
| ccggaaccct gtgtgctggg gaggaatccc gcagtggccg gggggcttga ggccgctgct | 60 |
| ttgtctcttc gtccagagcc ttatgtaaga gcttttctcg ggaaacagga agtcctgctt | 120 |
| gccaatttca gcacagggag tagtgcaggc cttattccaa cacacccggc ccagccttaa | 180 |
| ccccagaact cagccagttt cttgcttccg tgccccctggt tctcctcccc atcgagccca | 240 |
| cccctccttt cccaccttca gtcaccccta gtgaactgcc ccagcgatct ctgctgtgct | 300 |
| tgaccccgag ggtcttccac cctcgccctg accctggaca ctgcccagct ggcccccca | 360 |
| tcctgctcct ggcacaatgc cctctagcca gccaaccttc cctcccccaa ccctggggcc | 420 |
| gccccagggt tcctgcgcac tgcctgttcc tcctgggtgt cactggcagc cctgtccttc | 480 |
| ctagagggac tggaacctaa ttctcctgag gctgagggag ggtggagggt ctcaaggcaa | 540 |
| cgctggcccc acgacggagt gccaggagca ctaacagtac ccttagcttg ctttcctcct | 600 |
| ccctcctttt tattttcaag ttccttttta tttctccttg cgtaacaacc ttcttccctt | 660 |
| ctgcaccact gcccgtaccc ttacccgccc cgccacctcc ttgctacccc actcttgaaa | 720 |
| ccacagctgt tggcagggtc cccagctcat gccagcctca tctcctttct tgctagcccc | 780 |
| caaagggcct ccaggcaaca tgggggggccc agtcagagag ccggcactct cagttgccct | 840 |
| ctggttgagt tgggggggcag ctctgggggc cgtggcttgt gccatggctc tgctgaccca | 900 |
| acaaacagag ctgcagagcc tcaggagaga ggtgagccgg ctgcagggga caggaggccc | 960 |
| ctcccagaat ggggaagggt atccctggca gagtctcccg gagcagagtt ccgatgccct | 1020 |
| ggaagcctgg gagaatgggg agagatcccg gaaaaggaga gcagtgctca cccaaaaaca | 1080 |
| gaagaagcag cactctgtcc tgcacctggt tcccattaac gccacctcca aggatgactc | 1140 |
| cgatgtgaca gaggtgatgt ggcaaccagc tcttaggcgt gggagaggcc tacaggccca | 1200 |
| aggatatggt gtccgaatcc aggatgctgg agtttatctg ctgtatagcc aggtcctgtt | 1260 |
| tcaagacgtg actttcacca tgggtcaggt ggtgtctcga gaaggccaag gaaggcagga | 1320 |
| gactctattc cgatgtataa gaagtatgcc ctcccacccg accgggcct acaacagctg | 1380 |
| ctatagcgca ggtgtcttcc atttacacca aggggatatt ctgagtgtca taattccccg | 1440 |
| ggcaagggcg aaacttaacc tctctccaca tggaaccttc ctgggttttg tgaaactgtg | 1500 |
| attgtgttat aaaaagtggc tcccagcttg gaagaccagg gtgggtacat actggagaca | 1560 |
| gccaagagct gagtatataa aggagaggga atgtgcagga acagaggcgt cttcctgggt | 1620 |
| ttggctcccc gttcctcact tttcccttt cattcccacc ccctagactt tgattttacg | 1680 |
| gatatcttgc ttctgttccc catggagctc cgaattcttg cgtgtgtgta gatgaggggc | 1740 |
| ggggacggg cgccaggcat tgtccagacc tggtcggggc ccactggaag catccagaac | 1800 |
| agcaccacca tctagcggcc gctcgaggga agcacccgcc ggttggccga agtccacgaa | 1860 |
| gccgccctct gctagggaaa acccctggtt ctccatgcca cacctctctc caggtgccct | 1920 |
| ctgcctcttc accccacaag aagccttatc ctacgtcctt ctctccatct atcggacccc | 1980 |
| agtttccatc actatctcca gagatgtagc tattatgcgc ccgtctacag ggggtgcccg | 2040 |
| acgatgacgg tgccttcgca gtcaaattac tcttcgggtc ccaaggtttg gctttcacgc | 2100 |
| gctccattgc cccggcgtgg caggccattc caagcccttc cgggctggaa ctggtgtcgg | 2160 |
| aggagcctcg ggtgtatcgt acgccctggt gttggtgttg cctcactcct ctgagctctt | 2220 |
| ctttctgatc aagccctgct taaagttaaa taaaatagaa tgaatgatac cccggcaaaa | 2280 |
| aaaaaaaaaa aaa | 2293 |

<210> SEQ ID NO 101

<211> LENGTH: 2245
<212> TYPE: DNA
<213> ORGANISM: Homo sapiens

<400> SEQUENCE: 101

```
ccggaaccct gtgtgctggg gaggaatccc gcagtggccg gggggcttga ggccgctgct      60
ttgtctcttc gtccagagcc ttatgtaaga gcttttctcg ggaaacagga agtcctgctt     120
gccaatttca gcacagggag tagtgcaggc cttattccaa cacacccggc ccagccttaa     180
ccccagaact cagccagttt cttgcttccg tgccctggt tctcctcccc atcgagccca      240
cccctccttt cccaccttca gtcacccta gtgaactgcc ccagcgatct ctgctgtgct      300
tgaccccgag ggtcttccac cctcgccctg accctggaca ctgcccagct tggcccccca     360
tcctgctcct ggcacaatgc cctctagcca gccaacttc cctcccccaa ccctggggcc      420
gccccagggt tcctgcgcac tgcctgttcc tcctgggtgt cactggcagc cctgtccttc     480
ctagagggac tggaacctaa ttctcctgag gctgagggag ggtggagggt ctcaaggcaa     540
cgctggcccc acgacggagt gccaggagca ctaacagtac ccttagcttg ctttcctcct     600
ccctcctttt tattttcaag ttccttttta tttctccttg cgtaacaacc ttcttccctt     660
ctgcaccact gcccgtaccc ttacccgccc cgccacctcc ttgctacccc actcttgaaa     720
ccacagctgt tggcagggtc cccagctcat gccagcctca tctcctttct tgctagcccc     780
caaagggcct ccaggcaaca tggggggccc agtcagagag ccggcactct cagttgccct     840
ctggttgagt tgggggggcag ctctgggggc cgtggcttgt gccatggctc tgctgaccca    900
acaaacagag ctgcagagcc tcaggagaga ggtgagccgg ctgcagggga caggaggccc     960
ctcccagaat ggggaagggt atccctggca gagtctcccg gagcagagtt ccgatgccct    1020
ggaagcctgg gagaatgggg agagatcccg gaaaaggaga gcagtgctca cccaaaaaca    1080
gaagaatgac tccgatgtga cagaggtgat gtggcaacca gctcttaggc gtgggagagg    1140
cctacaggcc caaggatatg gtgtccgaat ccaggatgct ggagtttatc tgctgtatag    1200
ccaggtcctg tttcaagacg tgactttcac catgggtcag gtggtgtctc gagaaggcca    1260
aggaaggcag gagactctat tccgatgtat aagaagtatg ccctcccacc cggaccgggc    1320
ctacaacagc tgctatagcg caggtgtctt ccatttacac caagggata ttctgagtgt     1380
cataattccc cgggcaaggg cgaaacttaa cctctctcca catggaacct tcctggggtt    1440
tgtgaaactg tgattgtgtt ataaaagtg gctcccagct tggaagacca gggtgggtac     1500
atactggaga cagccaagag ctgagtatat aaaggagagg gaatgtgcag gaacagaggc    1560
gtcttcctgg gtttggctcc ccgttcctca cttttccctt ttcattccca cccctagac     1620
tttgatttta cggatatctt gcttctgttc cccatggagc tccgaattct tgcgtgtgtg    1680
tagatgaggg gcggggacg ggcgccaggc attgtccaga cctggtcggg gcccactgga     1740
agcatccaga acagcaccac catctagcgg ccgctcgagg gaagcacccg ccggttggcc    1800
gaagtccacg aagccgccct ctgctaggga aaaccctgg ttctccatgc cacacctctc     1860
tccaggtgcc ctctgcctct tcaccccaca agaagcctta tcctacgtcc ttctctccat    1920
ctatcggacc ccagtttcca tcactatctc cagagatgta gctattatgc gcccgtctac    1980
agggggtgcc cgacgatgac ggtgccttcg cagtcaaatt actcttcggg tcccaaggtt    2040
tggctttcac gcgctccatt gccccggcgt ggcaggccat tccaagccct tccgggctgg    2100
aactggtgtc ggaggagcct cgggtgtatc gtacgccctg tgttggtgt tgcctcactc     2160
ctctgagctc ttctttctga tcaagccctg cttaaagtta aataaaatag aatgaatgat    2220
```

| | |
|---|---:|
| accccggcaa aaaaaaaaaa aaaaa | 2245 |

<210> SEQ ID NO 102
<211> LENGTH: 2112
<212> TYPE: DNA
<213> ORGANISM: Homo sapiens

<400> SEQUENCE: 102

| | |
|---|---:|
| ccggaaccct gtgtgctggg gaggaatccc gcagtggccg gggggcttga ggccgctgct | 60 |
| ttgtctcttc gtccagagcc ttatgtaaga gcttttctcg ggaaacagga agtcctgctt | 120 |
| gccaatttca gcacagggag tagtgcaggc cttattccaa cacacccggc ccagccttaa | 180 |
| ccccagaact cagccagttt cttgcttccg tgccctggt tctcctcccc atcgagccca | 240 |
| cccctccttt cccaccttca gtcacccta gtgaactgcc ccagcgatct ctgctgtgct | 300 |
| tgaccccgag ggtcttccac cctcgccctg accctggaca ctgcccagct tggcccccca | 360 |
| tcctgctcct ggcacaatgc cctctagcca gccaaccttc cctcccccaa ccctggggcc | 420 |
| gccccagggt tcctgcgcac tgcctgttcc tcctgggtgt cactggcagc cctgtccttc | 480 |
| ctagagggac tggaacctaa ttctcctgag gctgagggag ggtggagggt ctcaaggcaa | 540 |
| cgctggcccc acgacggagt gccaggagca ctaacagtac ccttagcttg ctttcctcct | 600 |
| ccctcctttt tattttcaag ttccttttta tttctccttg cgtaacaacc ttcttccctt | 660 |
| ctgcaccact gcccgtaccc ttacccgccc cgccacctcc ttgctacccc actcttgaaa | 720 |
| ccacagctgt tggcagggtc cccagctcat gccagcctca tctcctttct tgctagcccc | 780 |
| caaagggcct ccaggcaaca tggggggccc agtcagagag ccggcactct cagttgccct | 840 |
| ctggttgagt tggggggcag ctctgggggc cgtggcttgt gccatggctc tgctgaccca | 900 |
| acaaacagag ctgcagagcc tcaggagaga ggtgagccgg ctgcaggga caggaggccc | 960 |
| ctcccagaat ggggaagggt atccctggca gagtctcccg gagcagagtt ccgatgccct | 1020 |
| ggaagcctgg gagaatgggg agagatcccg gaaaaggaga gcagtgctca cccaaaaaca | 1080 |
| gaagaagcag cactctgtcc tgcacctggt tcccattaac gccacctcca aggatgactc | 1140 |
| cgatgtgaca gaggtgatgt ggcaaccagc tcttaggcgt gggagaggcc tacaggccca | 1200 |
| aggatatggt gtccgaatcc aggatgctgg agtttatctg ctgtatagcc aggtcctgtt | 1260 |
| tcaagacgtg actttcacca tgggtcaggt ggtgtctcga aaggccaag gaaggcagga | 1320 |
| gactctattc cgatgtataa gaagtatgcc ctcccacccg gaccgggcct acaacagctg | 1380 |
| ctatagcgca ggtgtcttcc atttacacca aggggatatt ctgagtgtca taattccccg | 1440 |
| ggcaagggcg aaacttaacc tctctccaca tggaaccttc ctgggacttt gattttacgg | 1500 |
| atatcttgct tctgttcccc atggagctcc gaattcttgc gtgtgtgtag atgaggggcg | 1560 |
| ggggacgggc gccaggcatt gtccagacct ggtcggggcc cactggaagc atccagaaca | 1620 |
| gcaccaccat ctagcggccg ctcgagggaa gcacccgccg gttggccgaa gtccacgaag | 1680 |
| ccgccctctg ctagggaaaa cccctggttc tccatgccac acctctctcc aggtgccctc | 1740 |
| tgcctcttca ccccacaaga agccttatcc tacgtccttc tctccatcta tcggacccca | 1800 |
| gtttccatca ctatctccag agatgtagct attatgcgcc cgtctacagg gggtgcccga | 1860 |
| cgatgacggt gccttcgcag tcaaattact cttcgggtcc caaggtttgg cttttcacgcg | 1920 |
| ctccattgcc ccggcgtggc aggccattcc aagcccttcc gggctggaac tggtgtcgga | 1980 |
| ggagcctcgg gtgtatcgta cgccctggtg ttggtgttgc ctcactcctc tgagctcttc | 2040 |
| tttctgatca agccctgctt aaagttaaat aaaatagaat gaatgatacc ccggcaaaaa | 2100 |

-continued

```
aaaaaaaaaa aa                                                     2112

<210> SEQ ID NO 103
<211> LENGTH: 986
<212> TYPE: DNA
<213> ORGANISM: Homo sapiens

<400> SEQUENCE: 103
aactagggcc cggagcccgg ggtgctggag ggaggcggca ggcccgggtc aggggcctcg      60
agatcgggct tgggcccaga gcatgttcca gatcccagag tttgagccga gtgagcagga     120
agactccagc tctgcagaga ggggcctggg ccccagcccc gcaggggacg ggccctcagg     180
ctccggcaag catcatcgcc aggccccagg cctcctgtgg gacgccagtc accagcagga     240
gcagccaacc agcagcagcc atcatggagg cgctggggct gtggagatcc ggagtcgcca     300
cagctcctac cccgcgggga cggaggacga cgaagggatg ggggaggagc ccagcccctt     360
tcggggccgc tcgcgctcgg cgcccccaa cctctgggca gcacagcgct atggccgcga     420
gctccggagg atgagtgacg agtttgtgga ctcctttaag aagggacttc ctcgcccgaa     480
gagcgcgggc acagcaacgc agatgcggca aagctccagc tggacgcgag tcttccagtc     540
ctggtgggat cggaacttgg gcaggggaag ctccgccccc tcccagtgac cttcgctcca     600
catcccgaaa ctccaccecgt tcccactgcc ctgggcagcc atcttgaata tgggcggaag     660
tacttccctc aggcctatgc aaaaagagga tccgtgctgt ctcctttgga gggagggctg     720
acccagattc ccttccggtg cgtgtgaagc cacggaaggc ttggtcccat cggaagtttt     780
gggttttccg cccacagccg ccggaagtgg ctccgtggcc ccgccctcag gctccgggct     840
ttcccccagg cgcctgcgct aagtcgcgag ccaggtttaa ccgttgcgtc accgggaccc     900 gagccccgc gatgccctgg gggccgtgct cactaccaaa tgttaataaa gcccgcgtct     960
gtgccgccga aaaaaaaaaa aaaaaa                                       986
```